(12) United States Patent
Kumar et al.

(10) Patent No.: US 9,062,046 B2
(45) Date of Patent: Jun. 23, 2015

(54) SUBSTITUTED IMIDAZOQUINOLINE DERIVATIVES AS KINASE INHIBITORS

(75) Inventors: Sanjay Kumar, Mumbai (IN); Rajiv Sharma, Mumbai (IN); Robert Zahler, Pennington, NJ (US); Bichismita Sahu, Mumbai (IN); Veena R. Agarwal, Mumbai (IN); Nishigandha Naik, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 13/810,431

(22) PCT Filed: Jul. 15, 2011

(86) PCT No.: PCT/IB2011/053161
§ 371 (c)(1),
(2), (4) Date: Jan. 15, 2013

(87) PCT Pub. No.: WO2012/007926
PCT Pub. Date: Jan. 19, 2012

(65) Prior Publication Data
US 2013/0116248 A1    May 9, 2013

(51) Int. Cl.
| | | |
|---|---|---|
| A61K 31/43 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| C07D 471/04 | (2006.01) |
| A61K 31/4745 | (2006.01) |

(52) U.S. Cl.
CPC .......... *C07D 471/04* (2013.01); *A61K 31/4745* (2013.01)

(58) Field of Classification Search
None
See application file for complete search history.

(56) References Cited

U.S. PATENT DOCUMENTS 5,011,828 A * 4/1991 Goodman et al. ............. 514/45
2008/0262021 A1* 10/2008 Capraro et al. ............ 514/293

FOREIGN PATENT DOCUMENTS

| WO | 2006/029115 A2 | 3/2006 |
| WO | 2006/029155 A2 | 3/2006 |
| WO | WO 2006/029115 A1 * | 3/2006 |
| WO | WO 2006/029115 A2 * | 3/2006 |
| WO | 2006/122806 A2 | 11/2006 |
| WO | 2007/075468 A1 | 7/2007 |
| WO | 2009/029609 A1 | 3/2009 |

OTHER PUBLICATIONS

Carey, FA. Organic Chemistry 6th Ed. McGraw Hill. 2006, chapter 1, p. 9.*
Nakamura, I. et al. Transition-Metal-Catalyzed Reactions in Heterocyclic Synthesis. Chem. Rev. 2004, vol. 104, p. 2127.*
Chattopadhyay, SK. et al. Formation of medium-ring heterocycles by diene and enyne metathesis. Tetrahedron. 2007, vol. 63, p. 3919.*
Banfi L et al. Ugi Multicomponent Reaction Followed by an Intermolecular Nucleophilic Substitution: Convergent Multicomponent Synthesis of 1-sulfonyl 1,4-diazepan-5-ones and of their benzo-fuzed Derivatives. J. Org. Chem. 2007, vol. 72, p. 2151.*
Dorwold, FZ. Side Reactions in Organic Synthesis. Wiley. 2005, preface.*
International-type Search Report dated Nov. 18, 2011 for Application No. PCT/IB2011/015161.
Dagia, Nilesh M., et al., "A proteasome inhibitor reduces concurrent, sequential, and long-term IL-1β and TNF-α-induced ECAM expression and adhesion", Am J Physiol Cell Physiol 285, Jun. 4, 2003, pp. C813-C822.
Vigushin, David M., et al., "Histone deacetylase inhibitors in cancer treatment", Anti-Cancer Drugs 2002, 13, pp. 1-13.
Schabbauer, Gernot, et al., "PI3K-Akt Pathway Suppresses coagulation and Inflammation in Endotoxemic Mice", Arterioscler Thromb Vase Biol 2004;24, pp. 1963-1969.
Abdalla, S.A., et al., "Visceral manifestations in hereditary haemorrhagic telangiectasia type 2", J Med Genet 2003; 40, pp. 494-502.
Fuchikami, Kinji, et al., "A Versatile High-Throughput Screen for Inhibitors of Lipid Kinase Activity: Development of an Immobilized Phospholipid Plate Assay for Phosphoinositide 3-Kinase γ", Journal of Biomolecular Screening, 2002, vol. 7, No. 5, pp. 441-450.
Hennessy, Bryan T., et al., "Exploiting the PI3K/AKT Pathway for Cancer Drug Discovery", Nature Reviews Drug Discovery, Dec. 2005, vol. 4, pp. 988-1004.
Oh, Paul S., et al., "Activin receptor-like kinase 1 modulates transforming growth factor-β signaling in the regulation of angiogenesis", Proc. Natl. Acad. Sci., Mar. 14, 2000, vol. 97, No. 6, pp. 2626-2631.

* cited by examiner

*Primary Examiner* — Rita Desai
*Assistant Examiner* — Ben S Michelson
(74) *Attorney, Agent, or Firm* — Ladas & Parry LLP

(57) ABSTRACT

The present invention relates to substituted imidazo[4,5-c] quinoline derivatives, the compounds of formula (I), wherein $R_1$, $R_2$, $R_3$, $R_4$, $R_5$, $R_6$ and $R_7$ are as defined in the specification, processes for their preparation, pharmaceutical compositions comprising compounds of formula (I), and their use in the treatment of diseases or disorders mediated by one or more kinases, particularly proliferative diseases or disorders such as cancer. These compounds can also be used in the treatment of inflammatory diseases and angiogenesis related disorders.

14 Claims, No Drawings

SUBSTITUTED IMIDAZOQUINOLINE DERIVATIVES AS KINASE INHIBITORS

FIELD OF THE INVENTION

The present invention relates to substituted imidazo[4,5-c] quinoline derivatives (referred to herein as compounds of formula (I)), processes for their preparation, pharmaceutical compositions comprising the compounds of formula (I) and their use in the treatment of diseases or disorders mediated by one or more kinases, particularly proliferative diseases or disorders such as cancer. These compounds can also be used in the treatment of inflammatory disorder and angiogenesis related disorders.

BACKGROUND OF THE INVENTION

Cancer can be defined as abnormal growth of tissues characterized by a loss of cellular differentiation. It is caused due to a deregulation of the signaling pathways involved in cell survival, cell proliferation and cell death.

Current treatments for cancer have limited effectiveness and a number of side effects. Cancer therapy currently falls under the following categories including surgery, radiation therapy, chemotherapy, bone marrow transplantation, stem cell transplantation, hormonal therapy, immunotherapy, anti-angiogenic therapy, targeted therapy, gene therapy and others.

Angiogenesis is the process of forming new blood vessels and is critical in many normal and abnormal physiological states. Angiogenesis is normally observed in wound healing, fetal and embryonic development and formation of corpus luteum, endometrium and placenta. However angiogenesis is also the fundamental step in the transition of tumors from a dormant state to a malignant state. In diseases like cancer, the body loses the ability to maintain balanced angiogenesis. New blood vessels feed diseased tissues, destroying normal tissues and sometimes are involved in tumor metastasis. Hence, anti-angiogenic agents are a very promising class of drugs to block or slow the cancer growth.

Vascular Endothelial Growth Factor (VEGF), a signal protein, stimulates the growth of new blood vessels. It is involved in both vasculogenesis (the de novo formation of the embryonic circulatory system) and angiogenesis (the growth of blood vessels from pre-existing vasculature). Anti-VEGF therapies are important in the treatment of age-related macular degeneration and in certain cancers such as breast cancer, oesophageal cancer, melanoma, colorectal cancer and tumors of central nervous system.

Protein kinases play important roles in regulating most cellular functions such as proliferation, cell cycle, cell metabolism, survival, apoptosis, DNA damage repair, cell motility and response to the microenvironment. Protein kinases can be divided into broad groups based upon the identity of the amino acid(s) that they target (serine/threonine, tyrosine, lysine, and histidine). There are also dual-specific protein kinases that target both tyrosine and serine/threonine, such as mitogen-activated protein kinases (MAPKs). MAPKs are commonly activated in cancer cells and are known to contribute to tumorigenesis. The protein tyrosine kinases (PTKS) compose a large family of kinases that regulate cell to cell signals involved in growth, differentiation, adhesion, motility, and death. Members of the tyrosine kinase include, but are not limited to, MuSK, JAK2 and ROS. The JAKs are integral in signaling from extracellular cytokines, including the interleukins, interferons as well as numerous hormones. The importance of these kinases in cellular survival is made evident by the fact that the loss of JAKs is often accompanied by immunodeficiency and non-viability in animal models.

The family of serine/threonine kinases includes, but is not limited to, DNA-PK, ALK1, ALK2, CLK1, CLK4 and RIPK2. The DNA-PK is a nuclear serine/threonine protein kinase that is activated upon association with DNA. DNA-PK has been shown to be a crucial component of both the DNA double-strand break (DSB) repair machinery and the V(D)J recombination apparatus. DNA-PK is required for the non-homologous end joining (NHEJ) pathway of DNA repair, which rejoins double-strand breaks. Hence DNA-PK finds use in the treatment of cancers. Another kinase, activin receptor-like kinase 1 (ALK-1) is a type I cell surface receptor for transforming growth factor beta receptor type I (TGF-β1). Mutations in ALK-1 are associated with heredity hemorrhagic telangiectesia (HHT), suggesting a critical role for ALK-1 in the control of blood vessel development or repair (J. Med. Genet., 2003, 40, 494-502). Also, in-vivo experiments on ALK-1 knockout mice provide the evidence of ALK-1 involvement in angiogenesis (Proc. Natl. Acad. Sci. USA, 2000, 97, 2626-2631).

Phosphoinositide 3-kinases (PI3Ks) are attractive therapeutic targets in various diseases, such as autoimmune and inflammatory disorders and cancer.

PI3K mediated signaling pathway plays a very important role in cancer cell survival, cell proliferation, angiogenesis and metastasis. Activation of PI3K results in a disturbance of control of cell growth and survival, and hence this pathway is an attractive target for the development of novel anticancer agents (Nat. Rev. Drug Discov., 2005, 4, 988-1004). Activation of PI3K results in the recruitment and activation of protein kinase B (AKT) onto the membrane, which gets phosphorylated at Serine 473 (Ser-473).

Phosphatidylinositol-3-kinases or phosphoinositol-3-kinase (PI3-kinases or PI3Ks), are a family of lipid kinases that are capable of phosphorylating the 3 position hydroxyl group of the inositol ring of phosphatidylinositol. The PI3K family is composed of Class I, II and III. The classification is based on primary structure, regulation and in vitro lipid substrate specificity. Class III PI3K enzymes phosphorylate PI (phosphaotidylinositol) alone while, Class II PI3K enzymes phosphorylate both PI and PI 4-phosphate[PI(4)P]. Class I PI3K enzymes phosphorylate PI, PI(4)P and PI 4,5-biphosphate[PI(4,5)P$_2$]. Class I PI3Ks are further divided into two groups, class Ia and class Ib, in terms of their activation mechanism. Class Ia PI3Ks include PI3K p110α, p110β and p110δ subtypes and are generally activated in response to growth factor-stimulation of receptor tyrosine kinases. The regulatory p101 and catalytic p110γ subunits comprise the type Ib PI3K. The subtypes p110α and p110β are expressed in all cells, but p110δ is expressed primarily in leukocytes.

Akt is a serine/threonine protein kinase that plays a key role in multiple cellular processes such as glucose metabolism, cell proliferation, apoptosis, transcription and cell migration. It is known to positively regulate cell growth (accumulation of cell mass) by activating the mTOR serine threonine kinase. mTOR (mammalian target of rapamycin) serves as a molecular sensor that regulates protein synthesis on the basis of nutrients. mTOR regulates biogenesis by phosphorylating and activating p70S6 kinase (S6K1), which in turn enhances translation of mRNAs that have polypyrimidine tracts. The phosphorylation status of S6K1 is a bonafide read-out of mTOR function. Most tumors have an aberrant PI3K pathway (Nat. Rev. Drug Discov., 2005, 4, 988-1004). Since mTOR lies immediately downstream of PI3K, these tumors also have hyperactive mTOR function. Thus, most of the cancer types will potentially benefit from molecules that target PI3K and mTOR pathways.

Inhibition of PI3K-Akt pathway suppresses coagulation and inflammation (Arteriosclerosis, Thrombosis, and Vascular Biology, 2004, 24, 1963).

SF1126 (Semaphore Inc.) is in phase I clinical trials. SF1126 is a covalent conjugate of LY294002 containing a peptide-based targeting group. In vivo, it gets converted spontaneously at physiologic pH to LY294002 which is a viable version, and as a prodrug, it is able to block PI3K without affecting the normal cells. GDC-0941 (Piramed Ltd. and Genentech Inc.) is a PI3K inhibitor and is in phase I clinical trials. BEZ-235 and BGT-226 (Novartis AG), both in phase I/II clinical trials, inhibit all isoforms of PI3K and also inhibit the kinase activity of mTOR. XL-765 (Exelixis Inc.) is also a dual inhibitor of mTOR and PI3K. The compound is in phase I clinical trials as an oral treatment for solid tumors.

WO2006/122806 describes imidazoquinolines as lipid kinase inhibitors that are used alone or in combination with one or more other pharmaceutically active compounds for the treatment of an inflammatory or obstructive airway disease such as asthma or a proliferative disease such as a tumor disease.

SUMMARY OF THE INVENTION

According to one aspect of the present invention there are provided compounds of formula (I),

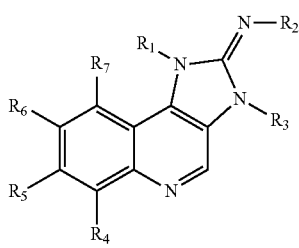

formula (I)

pharmaceutically acceptable salt, stereoisomers, tautomers and N-oxides thereof.

According to another aspect of the present invention there are provided processes for preparing compounds of formula (I).

According to another aspect of the present invention there are provided novel intermediates useful for preparing compounds of formula (I).

According to another aspect of the present invention there is provided a method for inhibiting kinase activity, such as the activity of PI3 kinase and/or mTOR, comprising contacting the kinase with an effective amount of a compound of formula (I).

According to another aspect of the present invention there is provided a method for the treatment of proliferative diseases or disorders mediated by one or more kinases, such as PI3 kinase and/or mTOR, comprising administering to a mammal in need thereof a therapeutically effective amount of a compound of formula (I). An example of such proliferative diseases or disorders includes, but is not limited to cancer.

According to yet another aspect of the present invention there is provided a method for the treatment of proliferative diseases or disorders, comprising administering to a mammal in need thereof a therapeutically effective amount of a compound of formula (I).

According to yet another aspect of the present invention there is provided a method for the treatment of angiogenesis related disorders such as cancer, age related macular degeneration or chronic inflammatory disease, comprising administering to a mammal in need thereof a therapeutically effective amount of a compound of formula (I).

According to yet another aspect of the present invention there is provided a method for the inhibition of angiogenesis, comprising administering to a mammal in need thereof a therapeutically effective amount of a compound of formula (I) for the treatment of angiogenesis related disorders.

According to yet another aspect of the present invention there is provided a method for the treatment of inflammatory diseases or disorders, comprising administering to a mammal in need thereof a therapeutically effective amount of a compound of formula (I).

According to another aspect of the present invention there is provided a pharmaceutical composition, comprising a compound of formula (I) or a pharmaceutically acceptable salt thereof in association with a pharmaceutically acceptable carrier, adjuvant, or vehicle.

These and other objectives and advantages of the present invention will be apparent to those skilled in the art from the following description.

DETAILED DESCRIPTION OF THE INVENTION

In one aspect, the present invention provides compounds of formula (I),

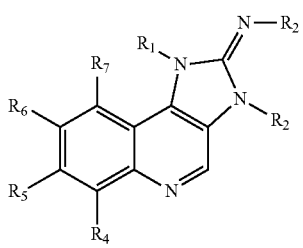

formula (I)

pharmaceutically acceptable salts, stereoisomers, tautomers and N-oxides thereof, wherein, $R_1$ is —$C_1$-$C_8$ alkyl, —$C_2$-$C_8$ alkenyl, —$C_2$-$C_8$ alkynyl, —$C_3$-$C_{10}$ cycloalkyl, —$C_6$-$C_{14}$ aryl, heterocyclyl, heteroaryl, alkylaryl, alkylheteroaryl, alkylheterocyclyl, —$CONR_xR_y$ or —$COR_x$, wherein each of —$C_1$-$C_8$ alkyl, —$C_2$-$C_8$ alkenyl, —$C_2$-$C_3$ alkynyl, —$C_3$-$C_{10}$ cycloalkyl, —$C_6$-$C_{14}$ aryl, heterocyclyl, heteroaryl, alkylaryl, alkylheteroaryl and alkylheterocyclyl is optionally substituted with one or more of $R^a$;

$R_2$ is nitro, —CN, —$CONR_xR_y$, —$COOR_x$, —$S(=O)_mR_x$, —$S(=O)_mNR_xR_y$, —$C_1$-$C_6$ alkyl or —$C_1$-$C_8$ alkoxy, wherein —$C_1$-$C_6$ alkyl is optionally substituted with —CN or —$NR_xR_y$;

$R_3$ is hydrogen, —$COR_x$, —$S(=O)_mR_x$, —$CONR_xR_y$ or —$C_1$-$C_8$ alkyl, wherein —$C_1$-$C_8$ alkyl is optionally substituted with one or more groups selected from —CN, —$CONR_xR_y$, —$COR_x$, —$COOR_x$, —$NR_xR_y$ or —$S(=O)_mR_x$;

$R_4$, $R_5$ and $R_7$ are independently hydrogen, nitro, halogen, —CN, —$OR_x$, —$CONR_xR_y$, —$NR_xCOR_y$, —$NR_xSO_2R_y$, —$NR_xCONR_xR_y$, —$COR_x$, —$C_1$-$C_8$ alkyl, $C_6$-$C_{14}$ aryl, heterocyclyl or heteroaryl, wherein each of —$C_1$-$C_8$ alkyl, —$C_6$-$C_{14}$ aryl, heterocyclyl, and heteroaryl is optionally substituted with one or more of $R^a$;

$R_6$ is hydrogen, halogen, $-NR_xR_y$, $-NR_xCOR_y$, $-OR_x$, $-SR_x$ or $R_1$;

$R^a$ at each occurrence is halogen, nitro, $-CN$, $-OR_x$, $-S(=O)_mR_x$, $-S(=O)_nNR_xR_y$, $-NR_xR_y$, $-NR_xCOR_y$, $-N(COR_y)_2$, $-NR_xCOOR_y$, $-NR_xSOR_y$, $-NR_xSO_2R_y$, $-NR_xCONR_xR_y$, $-NHCH_2O(CH_2)_2OR_x$, $-COR_x$, $-CO-OR_x$, $-CONR_xR_y$, $-(CH_2)_nNR_xCOOR_y$, -oxo-, $C_1$-$C_8$ alkyl, $C_2$-$C_8$ alkenyl, $-C_2$-$C_8$ alkynyl, $-C_6$-$C_{14}$ aryl, alkylaryl, heterocyclyl, alkylheterocyclyl, heteroaryl or alkylheteroaryl, wherein each of $-C_1$-$C_8$ alkyl, $-C_2$-$C_8$ alkenyl, $-C_2$-$C_8$ alkynyl, $-C_6$-$C_{14}$ aryl, alkylaryl, heterocyclyl, alkylheterocyclyl, heteroaryl and alkylheteroarylaryl is optionally substituted with one or more of $R^b$;

wherein $R_x$ and $R_y$ at each occurrence are independently hydrogen, $-C_1$-$C_8$ alkyl, $-C_2$-$C_8$ alkenyl, $-C_2$-$C_8$ alkynyl, $-C_3$-$C_{10}$ cycloalkyl, alkylcycloalkyl, $-C_6$-$C_{14}$ aryl, alkylaryl, heterocyclyl, alkylheterocyclyl, heteroaryl or alkylheteroaryl, wherein each of $-C_1$-$C_8$ alkyl, $-C_2$-$C_8$ alkenyl, $-C_2$-$C_8$ alkynyl, $-C_3$-$C_{10}$ cycloalkyl, alkylcycloalkyl, $-C_6$-$C_{14}$ aryl, alkylaryl, heterocyclyl, alkylheterocyclyl, heteroaryl and alkylheteroaryl are optionally substituted with $R^b$;

$R^b$ at each occurrence is halogen, nitro, $-CN$, hydroxy, $-C_1$-$C_8$ alkoxy, $-COOH$, $-NH_2$, $-C(O)O-C_1$-$C_8$ alkyl or $-C_1$-$C_8$ alkyl;

m is 0 or an integer from 1 to 2; and n is an integer from 1 to 2.

Definitions

Listed below are definitions, which apply to the terms as they are used throughout the specification and the appended claims (unless they are otherwise limited in specific instances), either individually or as part of a larger group. It will be understood that "substitution" or "substituted by" or "substituted with" includes the implicit proviso that such substitution is in accordance with the permitted valence of the substituted atom and the substituent, as well as represents a stable compound, which does not readily undergo transformation such as by rearrangement, cyclization, elimination, etc. The term "optionally substituted" is used interchangeably with the phrase "substituted or unsubstituted". Unless otherwise indicated, an optionally substituted group may have a substituent at each substitutable position of the group, and each substitution is independent of the other.

The term "halogen" as used herein refers to an atom selected from F, Cl, Br and I.

The term "alkyl" whether used alone or as part of a substituent group, refers to the radical of saturated aliphatic groups, including straight or branched-chain containing from 1 to 8 carbon atoms. Furthermore, unless stated otherwise, the term "alkyl" includes unsubstituted as well as substituted alkyl. Examples of alkyl groups include but are not limited to methyl, ethyl, propyl, butyl, isopropyl, isobutyl, 1-methylbutyl, isopentyl, neopentyl, 2,2-dimethylbutyl, 2-methylpentyl, 3-methylpentyl, sec-butyl, tert-butyl and the like. The "alkyl" group as defined above may be interrupted by oxygen or sulfur, means, any ether and thioether groups respectively containing from 1 to 8 carbon atoms are also included in the definition of "alkyl" group.

The term "alkenyl" as used herein refers to an unsaturated, branched or straight chain alkyl group having from 2 to 8 carbon atoms, suitably 2 to 6 carbon atoms, preferably 2 to 4 carbon atoms, and at least one carbon-carbon double bond (two adjacent $sp^2$ carbon atoms). Depending on the placement of double bond and substituents if any, the geometry of the double bond may be entgegen (E), or zusammen (Z), cis or trans. Furthermore, unless stated otherwise, the term "alkenyl" includes unsubstituted as well as substituted alkenyl.

Examples of alkenyl include but are not limited to ethenyl, propenyl, pent-2-enyl, 2-isopentenyl, cis-2-butenyl, trans-2-butenyl, 2-methyl-2-propenyl and the like.

The term "alkynyl" as used herein refers to an unsaturated, branched or straight chain alkyl group having from 2 to 8 carbon atoms, suitably 2 to 6 carbon atoms, preferably 2 to 4 carbon atoms, and at least one carbon-carbon triple bond (two adjacent sp carbon atoms). Furthermore, unless stated otherwise, the term "alkynyl" includes unsubstituted as well as substituted alkynyl. Examples of alkynyl include, but are not limited to, ethynyl, 1-propynyl, 3-propynyl, 3-butynyl and the like.

The term "alkoxy" as used herein refers to $-O$-alkyl, where alkyl is as defined above. Furthermore, unless stated otherwise, the term "alkoxy" includes unsubstituted as well as substituted alkoxy. Examples of alkoxy include, but are not limited to, methoxy, ethoxy, propoxy and the like.

The term "cycloalkyl" as used herein refers to a saturated or partially unsaturated cyclic hydrocarbon group including a mono-, bi- or poly-cyclic ring system and including a total of 3 to 10 ring carbon atoms. Furthermore, unless stated otherwise, the term "cycloalkyl" includes unsubstituted as well as substituted cycloalkyl. Examples of cycloalkyl include, but are not limited to, cyclopropyl, cyclobutyl, cyclopentyl, cyclohexyl, adamantyl, [3,3,0]bicyclooctanyl-, [4,4,0]bicyclodecanyl, indene and the like.

The term "aryl" as used herein refers to a monocyclic or polycyclic hydrocarbon group having up to 14 ring carbon atoms, preferably up to 10 ring carbon atoms, more preferably up to 6 ring carbon atoms in which at least one carbocyclic ring is present that has a conjugated π electron system. Accordingly, the term "aryl" refers to $-C_6$-$C_{14}$ aryl. Furthermore, unless stated otherwise, the term "aryl" includes unsubstituted as well as substituted aryl. Examples of aryl include but are not limited to phenyl, naphthyl, tetrahydronaphthyl and the like. Aryl residues can be bonded via any desired position, and in substituted aryl residues, the substituents can be located in any desired position.

The term "heterocyclyl" or "heterocycle" as used herein refers to a saturated or partially unsaturated monocyclic or polycyclic ring system containing 5 to 20 ring atoms, suitably 5 to 10 ring atoms, of which 1, 2, 3 or 4 are identical or different heteroatoms selected from N, O and S. The "heterocyclyl" or "heterocycle" may, for example, have 1 to 2 oxygen atoms and/or 1 to 2 sulfur atoms and/or 1 to 4 nitrogen atoms in the ring. The ring heteroatoms can be present in any position with respect to each other provided that the resulting "heterocyclyl" or "heterocycle" is stable. Furthermore, unless stated otherwise, the term "heterocyclyl" or "heterocycle" includes unsubstituted as well as substituted "heterocyclyl" or "heterocycle". Examples of "heterocyclyl" or "heterocycle" include but are not limited to: azocinyl, chromanyl, decahydroquinolinyl, oxadiazolidinyl, imidazolidinyl, indolinyl, isobenzofuranyl, isoindolinyl, isooxazolinyl, morpholinyl, octahydroisoquinolinyl, oxazolidinyl, piperidinyl, piperazinyl, pyranyl, dihydropyridyl, tetrahydropyrimidyl, benzopyranyl, pyrazolinyl, pyrazolidinyl, pyrrolidinyl, pyrrolinyl, 4H-quinolizinyl, tetrahydrofuranyl, benzodioxolyl, tetrahydroisoquinolinyl, tetrahydroquinolinyl, 6H-1,2,5-thiadiazinyl and xanthenyl.

The term "heteroaryl" as used herein refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. The rings may contain from 1 to 4 heteroatoms selected from N, O and S, wherein the N or S atom is optionally oxidized, or the N atom is optionally quaternized. Any suitable ring position of the heteroaryl moiety may be covalently linked to the defined chemical structure. Furthermore, unless stated otherwise, the term "heteroaryl" includes unsubstituted as well as substituted heteroaryl. Examples of heteroaryl include, but are not limited to, furan, thiophene, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzodiazolyl, carbazolyl, dibenzothienyl, acridinyl, and the like.

The term "alkylcycloalkyl" as used herein refers to a cycloalkyl group bonded through an alkyl group, wherein the terms "alkyl" and "cycloalkyl" are as defined herein above. Furthermore, unless stated otherwise, the term "alkylcycloalkyl" includes unsubstituted as well as substituted alkylcycloalkyl. Examples of alkylcycloalkyl include but not limited to cyclohexylmethyl, cyclopentylmethyl and the like.

The term "alkylaryl" as used herein refers to an aryl group bonded through an alkyl, wherein the terms "alkyl" and "aryl" are as defined herein above. Furthermore, unless stated otherwise, the term "alkylaryl" includes unsubstituted as well as substituted alkylaryl. Examples of alkylaryl include but not limited to benzyl, 1-naphthyl ethyl, 1-phenyl ethyl and the like.

The term "alkylheterocycle" as used herein refers to a heterocycle group bonded through an alkyl, wherein the terms "alkyl" and "heterocycle" are as defined herein above. Furthermore, unless stated otherwise, the term "alkylheterocycle" includes unsubstituted as well as substituted alkylheterocycle. Examples of alkylheterocycle include but not limited to piperazin-1-ylmethyl, piperidin-1-ylmethyl, pyrrolidin-2-ylmethyl, 2-morpholinoethyl and the like.

The term "alkylheteroaryl" as used herein refers to a heteroaryl group bonded through an alkyl, wherein the terms "alkyl" and "heteroaryl" are as defined herein above. Furthermore, unless stated otherwise, the term "alkylheteroaryl" includes unsubstituted as well as substituted alkylheteroaryl. Examples of alkylheteroaryl include but not limited to pyridin-4-yl-ethyl, imidazol-4-yl-ethyl and the like.

The term "compound of the present invention" and "compound of this invention" and "compounds of formula (I)" includes compounds of formula (I) and stereoisomers, tautomers, solvates, N-oxides and pharmaceutically acceptable salts thereof.

The term "stereoisomer" as used herein refers to all isomers of individual compounds that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention.

The term "tautomer" as used herein refers to the coexistence of two (or more) compounds that differ from each other only in the position of one (or more) mobile atoms and in electron distribution, for example, keto-enol and imine-enamine tautomers.

The term "solvate" as used herein refers to a compound formed by the interaction of a solute (in this invention, a compound of formula (I) or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Examples for suitable solvates are the mono- or dihydrates or alcoholates of the compounds according to the invention.

The term "pharmaceutically acceptable salts" as used herein refers to organic and inorganic salts of a compound of the invention. The compounds of the present invention represented by the general formula (I), which contain acidic groups, may be converted into salts with pharmaceutically acceptable bases. Such salts include, for example, alkali metal salts, like lithium, sodium and potassium salts; alkaline earth metal salts like calcium and magnesium salts, ammonium salts, for example, [tris(hydroxymethyl)aminomethane], trimethylamine salts and diethylamine salts; salts with amino acids such as lysine, arginine, guanidine and the like.

The compounds of the present invention represented by the general formula (I), which contain one or more basic groups, i.e. groups which can be protonated, can form an addition salt with an inorganic or organic acid. Examples of suitable acid addition salts include: acetates, alginates, ascorbates, aspartates, benzoates, benzenesulfonates, bisulfates, borates, cinnamates, citrates, ethanesulfonates, fumarates, glucuronates, glutamates, glycolates, hydrochlorides, hydrobromides, hydrofluorides, ketoglutarates, lactates, maleates, malonates, methanesulfonates, nitrates, oxalates, palmoates, perchlorates, phosphates, picrates, salicylates, succinates, sulfamate, sulfates, tartrates, toluenesulfonates and other acid addition salts known to the person skilled in the art.

The term "N-oxide" as used herein refers to the oxide of the nitrogen atom of a nitrogen-containing heteroaryl or heterocycle. N-oxide can be formed in presence of an oxidizing agent for example peroxide such as m-chloro-perbenzoic acid or hydrogen peroxide.

The present invention also includes within its scope all isotopically labeled forms of compounds of formula (I), wherein one or more atoms of compounds of formula (I) are replaced by their respective isotopes. All isotopes of any particular atom or element as specified are contemplated within the scope of the compounds of the invention. Examples of isotopes that may be incorporated into the compounds disclosed herein include, but are not limited to, isotopes of hydrogen such as $^{2}H$ and $^{3}H$, carbon such as $^{11}C$, $^{13}C$ and $^{14}C$, nitrogen such as $^{13}N$ and $^{15}N$, oxygen such as $^{15}O$, $^{17}O$ and $^{18}O$, chlorine such as $^{36}Cl$, fluorine such as $^{18}F$ and sulphur such as $^{35}S$. Substitution with heavier isotopes, for example, replacing one or more key carbon-hydrogen bonds with carbon-deuterium bond may show certain therapeutic advantages, resulting from longer metabolism cycles, (e.g., increased in-vivo half life or reduced dosage requirements), improved safety or greater effectiveness and hence may be preferred in certain circumstances.

In one embodiment, the invention provides a compound of formula (I),

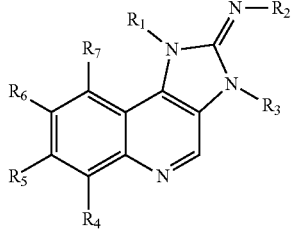

formula (I)

pharmaceutically acceptable salts, stereoisomers, tautomers and N-oxides thereof, wherein, $R_1$ is —$C_1$-$C_8$ alkyl, —$C_2$-$C_8$ alkenyl, —$C_2$-$C_8$ alkynyl, —$C_3$-$C_{10}$ cycloalkyl, —$C_6$-$C_{14}$ aryl, heterocyclyl, heteroaryl, alkylaryl, alkylheteroaryl, alkylheterocyclyl, —$CONR_xR_y$, or —$COR_x$, wherein each of —$C_1$-$C_8$ alkyl, —$C_2$-$C_8$ alkenyl, —$C_2$-$C_8$ alkynyl, —$C_3$-$C_{10}$ cycloalkyl, —$C_6$-$C_{14}$ aryl, heterocyclyl, heteroaryl, alkylaryl, alkylheteroaryl and alkylheterocyclyl is optionally substituted with one or more of $R^a$;

$R_2$ is nitro or —CN;

$R_3$ is hydrogen or —$C_1$-$C_8$ alkyl, wherein —$C_1$-$C_8$ alkyl is optionally substituted with one or more groups selected from —CN or —$NR_xR_y$;

$R_4$, $R_5$ and $R_7$ are hydrogen;

$R_6$ is hydrogen, halogen, —$NR_xR_y$, —$NR_xCOR_y$, —$OR_x$, —$SR_x$ or $R_1$;

$R^a$ at each occurrence is halogen, nitro, —CN, —$OR_x$, —$S(=O)_mR_x$, —$S(=O)_nNR_xR_y$, —$NR_xR_y$, —$NR_xCOR_y$, —$N(COR_y)_2$, —$NR_xCOOR_y$, —$NR_xSOR_y$, —$NR_xSO_2R_y$, —$NR_xCONR_xR_y$, —$COR_x$, —$COOR_x$, —$CONR_xR_y$, —$(CH_2)_nNR_xCOOR_y$, -oxo-, —$NHCH_2O(CH_2)_2OR_x$, —$C_1$-$C_8$ alkyl, —$C_2$-$C_8$ alkenyl, —$C_2$-$C_8$ alkynyl, —$C_6$-$C_{14}$ aryl, alkylaryl, heterocyclyl, alkylheterocyclyl, heteroaryl or alkylheteroaryl, wherein each of —$C_1$-$C_8$ alkyl, —$C_2$-$C_8$ alkenyl, —$C_2$-$C_8$ alkynyl, —$C_6$-$C_{14}$ aryl, alkylaryl, heterocyclyl, alkylheterocyclyl, heteroaryl and alkylheteroarylaryl is optionally substituted with one or more of $R^b$;

wherein $R_x$ and $R_y$ at each occurrence are independently hydrogen, —$C_1$-$C_8$ alkyl, —$C_2$-$C_8$ alkenyl, —$C_2$-$C_8$ alkynyl, —$C_3$-$C_{10}$ cycloalkyl, alkylcycloalkyl, —$C_6$-$C_{14}$ aryl, alkylaryl, heterocyclyl, alkylheterocyclyl, heteroaryl or alkylheteroaryl, wherein each of —$C_1$-$C_8$ alkyl, —$C_2$-$C_8$ alkenyl, —$C_2$-$C_8$ alkynyl, —$C_3$-$C_{10}$ cycloalkyl, alkylcycloalkyl, —$C_6$-$C_{14}$ aryl, alkylaryl, heterocyclyl, alkylheterocyclyl, heteroaryl and alkylheteroaryl are optionally substituted with $R^b$;

$R^b$ at each occurrence is halogen, nitro, —CN, hydroxy, —$C_1$-$C_8$ alkoxy, —COOH, —C(O)O—$C_1$-$C_8$ alkyl, —$NH_2$ or —$C_1$-$C_8$ alkyl;

m is 0 or an integer from 1 to 2; and n is an integer from 1 to 2.

In another embodiment, the invention provides a compound of formula (I),

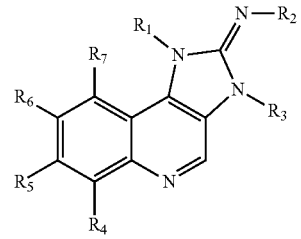

formula (I)

pharmaceutically acceptable salts, stereoisomers, tautomers and N-oxides thereof, wherein, $R_1$ is —$C_6$-$C_{14}$ aryl, heterocyclyl, heteroaryl or alkylheterocyclyl, wherein each of —$C_6$-$C_{14}$ aryl, heterocyclyl, heteroaryl and alkylheterocyclyl is optionally substituted with one or more of $R^a$;

$R_2$ is nitro or —CN;

$R_3$ is hydrogen or —$C_1$-$C_8$ alkyl, wherein —$C_1$-$C_8$ alkyl is optionally substituted with one or more groups selected from —CN or —$NR_xR_y$;

$R_4$, $R_5$ and $R_7$ are hydrogen;

$R_6$ is hydrogen, halogen, —$NR_xR_y$, —$NR_xCOR_y$, —$OR_x$, —$SR_x$ or $R_1$;

$R^a$ at each occurrence is halogen, nitro, —CN, —$OR_x$, —$S(=O)_mR_x$, —$S(=O)_nNR_xR_y$, —$NR_xR_y$, —$NR_xCOR_y$, —$N(COR_y)_2$, —$NR_xCOOR_y$, —$NR_xSOR_y$, —$NR_xSO_2R_y$, —$NR_xCONR_xR_y$, —$COR_x$, —$COOR_x$, —$CONR_xR_y$, —$(CH_2)_nNR_xCOOR_y$, -oxo-, —$NHCH_2O(CH_2)_2OR_x$, —$C_1$-$C_8$ alkyl, —$C_2$-$C_8$ alkenyl, —$C_2$-$C_8$ alkynyl, —$C_6$-$C_{14}$ aryl, alkylaryl, heterocyclyl, alkylheterocyclyl, heteroaryl or alkylheteroaryl, wherein each of —$C_1$-$C_8$ alkyl, —$C_2$-$C_8$ alkenyl, —$C_2$-$C_8$ alkynyl, —$C_6$-$C_{14}$ aryl, alkylaryl, heterocyclyl, alkylheterocyclyl, heteroaryl and alkylheteroarylaryl is optionally substituted with one or more of $R^b$;

wherein $R_x$ and $R_y$ at each occurrence are independently hydrogen, —$C_1$-$C_8$ alkyl, —$C_2$-$C_8$ alkenyl, —$C_2$-$C_8$ alkynyl, —$C_3$-$C_{10}$ cycloalkyl, alkylcycloalkyl, —$C_6$-$C_{14}$ aryl, alkylaryl, heterocyclyl, alkylheterocyclyl, heteroaryl or alkylheteroaryl, wherein each of —$C_1$-$C_8$ alkyl, —$C_2$-$C_8$ alkenyl, —$C_2$-$C_8$ alkynyl, —$C_3$-$C_{10}$ cycloalkyl, alkylcycloalkyl, —$C_6$-$C_{14}$ aryl, alkylaryl, heterocyclyl, alkylheterocyclyl, heteroaryl and alkylheteroaryl are optionally substituted with $R^b$;

$R^b$ at each occurrence is halogen, nitro, —CN, hydroxy, $C_1$-$C_8$ alkoxy, —COOH, —C(O)O—$C_1$-$C_8$ alkyl, —$NH_2$ or —$C_1$-$C_8$ alkyl;

m is 0 and n is an integer from 1 to 2.

In another embodiment, the invention provides a compound of formula (I),

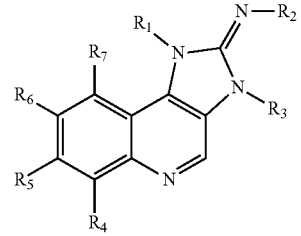

formula (I)

pharmaceutically acceptable salts, stereoisomers, tautomers and N-oxides thereof, wherein, $R_1$ is —$C_6$-$C_{14}$ aryl, heterocyclyl, heteroaryl or alkylheterocyclyl, wherein each of —$C_6$-$C_{14}$ aryl, heterocyclyl, heteroaryl and alkylheterocyclyl is optionally substituted with one or more of $R^a$;

$R_2$ is nitro or —CN;

$R_3$ is hydrogen or —$C_1$-$C_8$ alkyl, wherein —$C_1$-$C_8$ alkyl is optionally substituted with one or more groups selected from —CN or —$NR_xR_y$;

$R_4$, $R_5$ and $R_7$ are hydrogen;

$R_6$ is —$C_6$-$C_{14}$ aryl, heterocyclyl or heteroaryl, wherein each of —$C_6$-$C_{14}$ aryl, heterocyclyl and heteroaryl is optionally substituted with one or more of $R^a$;

$R^a$ at each occurrence is halogen, nitro, —CN, —$OR_x$, —$S(=O)_mR_x$, —$S(=O)_nNR_xR_y$, —$NR_xR_y$, —$NR_xCOR_y$, —$N(COR_y)_2$, —$NR_xCOOR_y$, —$NR_xSOR_y$, —$NR_xSO_2R_y$, —$NR_xCONR_xR_y$, —$COR_x$, —$COOR_x$, —$CONR_xR_y$, —$(CH_2)_nNR_xCOOR_y$, -oxo-, —$NHCH_2O(CH_2)_2OR_x$, —$C_1$-$C_8$ alkyl, —$C_2$-$C_8$ alkenyl, —$C_2$-$C_8$ alkynyl, —$C_6$-$C_{14}$ aryl, alkylaryl, heterocyclyl, alkylheterocyclyl, heteroaryl or alkylheteroaryl, wherein each of —$C_1$-$C_8$ alkyl, —$C_2$-$C_8$ alkenyl, —$C_2$-$C_8$ alkynyl, —$C_6$-$C_{14}$ aryl, alkylaryl, heterocyclyl, alkylheterocyclyl, heteroaryl and alkylheteroarylaryl is optionally substituted with one or more of $R^b$;

wherein $R_x$ and $R_y$ at each occurrence are independently hydrogen, —$C_1$-$C_8$ alkyl, —$C_2$-$C_8$ alkenyl, —$C_2$-$C_8$ alkynyl, —$C_3$-$C_{10}$ cycloalkyl, alkylcycloalkyl, —$C_6$-$C_{14}$ aryl, alkylaryl, heterocyclyl, alkylheterocyclyl, heteroaryl or alkylheteroaryl, wherein each of —$C_1$-$C_8$ alkyl, —$C_2$-$C_8$ alkenyl, —$C_2$-$C_8$ alkynyl, cycloalkyl, alkylcycloalkyl, —$C_6$-$C_{14}$ aryl, alkylaryl, heterocyclyl, alkylheterocyclyl, heteroaryl and alkylheteroaryl are optionally substituted with $R^b$;

$R^b$ at each occurrence is halogen, nitro, —CN, hydroxy, $C_1$-$C_8$ alkoxy, —COOH, —C(O)O—$C_1$-$C_8$ alkyl, —$NH_2$ or —$C_1$-$C_8$ alkyl;

m is 0 and n is an integer from 1 to 2.

In another embodiment, the invention provides a compound of formula (I),

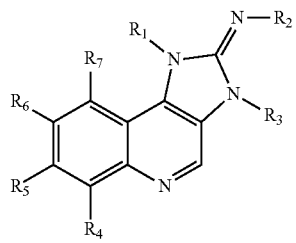

formula (I)

pharmaceutically acceptable salts, stereoisomers, tautomers and N-oxides thereof, wherein, $R_1$ is —$C_6$-$C_{14}$ aryl, heterocyclyl, heteroaryl or alkylheterocyclyl, wherein each of —$C_6$-$C_{14}$ aryl, heterocyclyl, heteroaryl and alkylheterocyclyl is optionally substituted with one or more of $R^a$;

$R_2$ is nitro or —CN;

$R_3$ is hydrogen or —$C_1$-$C_3$ alkyl, wherein —$C_1$-$C_3$ alkyl is optionally substituted with one or more groups selected from —CN or —$NR_xR_y$;

$R_4$, $R_5$ and $R_7$ are hydrogen;

$R_6$ is —$C_6$-$C_{14}$ aryl, heterocyclyl or heteroaryl, wherein each of —$C_6$-$C_{14}$ aryl, heterocyclyl and heteroaryl is optionally substituted with one or more of $R^a$;

$R^a$ at each occurrence is halogen, nitro, —CN, —$OR_x$, —$S(=O)_mR_x$, —$NR_xR_y$, —$NR_xCOR_y$, —$N(COR_y)_2$, —$NR_xCOOR_y$, —$NR_xSO_2R_y$, —$NR_xCONR_xR_y$, —$COR_x$, —$COOR_x$, —$CONR_xR_y$, —$(CH_2)_nNR_xCOOR_y$, -oxo-, —$NHCH_2O(CH_2)_2OR_x$, —$C_1$-$C_6$ alkyl, —$C_6$-$C_{14}$ aryl, alkylaryl, heterocyclyl, alkylheterocyclyl, heteroaryl or alkylheteroaryl, wherein each of —$C_1$-$C_6$ alkyl, —$C_6$-$C_{14}$ aryl, alkylaryl, heterocyclyl, alkylheterocyclyl, heteroaryl and alkylheteroarylaryl is optionally substituted with one or more of $R^b$;

wherein $R_x$ and $R_y$ at each occurrence are independently hydrogen, —$C_1$-$C_8$ alkyl, —$C_6$-$C_{14}$ aryl or alkylaryl, wherein each of —$C_1$-$C_8$ alkyl, —$C_6$-$C_{14}$ aryl and alkylaryl are optionally substituted with $R^b$;

$R^b$ at each occurrence is halogen, nitro, —CN, hydroxy, $C_1$-$C_8$ alkoxy, —COOH, —C(O)O—$C_1$-$C_8$ alkyl, —$NH_2$ or —$C_1$-$C_4$ alkyl;

m is 0 and n is an integer from 1 to 2.

In another embodiment, the invention provides a compound of formula (I), wherein $R_1$ is alkylheterocyclyl, —$C_6$-$C_{14}$ aryl or heteroaryl, wherein each of alkylheterocyclyl, —$C_6$-$C_{14}$ aryl and heteroaryl is optionally substituted with one or more of $R^a$.

In another embodiment, the invention provides a compound of formula (I), wherein $R_1$ is alkylheterocyclyl, —$C_6$-$C_{14}$ aryl or heteroaryl, wherein each of alkylheterocyclyl, —$C_6$-$C_{14}$ aryl and heteroaryl is optionally substituted with one or more of $R^a$, wherein $R^a$ at each occurrence is halogen, nitro, —CN, —$OR_x$, —$S(=O)_mR_x$, —$S(=O)_nNR_xR_y$, —$NR_xR_y$, —$NR_xCOR_y$, —$NR_xSOR_y$, —$NR_xSO_2R_y$, —$NR_xCONR_xR_y$, —$COR_x$, —$COOR_x$, —$CONR_xR_y$, —$C_1$-$C_8$ alkyl, —$C_6$-$C_{14}$ aryl, heterocyclyl or heteroaryl, wherein each of —$C_1$-$C_8$ alkyl, —$C_6$-$C_{14}$ aryl, heterocyclyl, and heteroaryl is optionally substituted with one or more of $R^b$;

wherein $R_x$ and $R_y$ at each occurrence are independently hydrogen, —$C_1$-$C_8$ alkyl, —$C_6$-$C_{14}$ aryl, heterocyclyl or heteroaryl, wherein each of —$C_1$-$C_8$ alkyl, —$C_6$-$C_{14}$ aryl, heterocyclyl and heteroaryl is optionally substituted with $R^b$;

$R^b$ at each occurrence is halogen, nitro, —CN, hydroxy, —$C_1$-$C_8$ alkoxy, —COOH, —C(O)O—$C_1$-$C_8$ alkyl, —$NH_2$ or —$C_1$-$C_8$ alkyl;

m is 0; and n is an integer from 1 to 2.

In another embodiment, the invention provides a compound of formula (I), wherein $R_1$ is —$C_6$-$C_{14}$ aryl, wherein —$C_6$-$C_{14}$ aryl is optionally substituted with one or more of $R^a$.

In another embodiment, the invention provides a compound of formula (I), wherein $R_1$ is phenyl, wherein phenyl is optionally substituted with one or more of $R^a$.

In another embodiment, the invention provides a compound of formula (I), wherein $R_1$ is phenyl substituted with —$C_1$-$C_8$ alkyl, wherein —$C_1$-$C_8$ alkyl is optionally substituted with —CN.

In another embodiment, the invention provides a compound of formula (I), wherein $R_1$ is heteroaryl, wherein heteroaryl is optionally substituted with one or more of $R^a$.

In another embodiment, the invention provides a compound of formula (I), wherein $R_1$ is pyridyl or quinolinyl, wherein pyridyl and quinolinyl are optionally substituted with one or more of $R^a$.

In another embodiment, the invention provides a compound of formula (I), wherein $R_1$ is selected from phenyl, pyridyl, quinolinyl and 2-morpholinoethyl, wherein each of phenyl, pyridyl, quinolinyl and 2-morpholinoethyl is optionally substituted with one or more of $R^a$, wherein $R^a$ at each occurrence is halogen, nitro, —CN, —$OR_x$, —$S(=O)_mR_x$, —$S(=O)_nNR_xR_y$, —$NR_xR_y$, —$NR_xCOR_y$, —$NR_xSOR_y$, —$NR_xSO_2R_y$, —$NR_xCONR_xR_y$, —$COR_x$, —$COOR_x$, —CONR$_x$R$_y$, —C$_1$-C$_8$ alkyl, —C$_6$-C$_{14}$ aryl, heterocyclyl or heteroaryl, wherein each of —C$_1$-C$_8$ alkyl, —C$_6$-C$_{14}$ aryl, heterocyclyl, and heteroaryl is optionally substituted with one or more of R$^b$;

wherein R$_x$ and R$_y$ at each occurrence are independently hydrogen, —C$_1$-C$_8$ alkyl, —C$_6$-C$_{14}$ aryl, heterocyclyl or heteroaryl, wherein each of —C$_1$-C$_8$ alkyl, —C$_6$-C$_{14}$ aryl, heterocyclyl and heteroaryl is optionally substituted with R$^b$;

R$^b$ at each occurrence is halogen, nitro, —CN, hydroxy, —C$_1$-C$_8$ alkoxy, —COOH, —C(O)O—C$_1$-C$_8$ alkyl, —NH$_2$ or —C$_1$-C$_8$ alkyl;

m is 0; and n is an integer from 1 to 2.

In another embodiment, the invention provides a compound of formula (I), wherein R$_1$ is pyridyl or quinolinyl, wherein pyridyl and quinolinyl are optionally substituted with one or more groups selected from halogen, —CN, —OR$_x$, —C$_6$-C$_{14}$ aryl and —C$_1$-C$_8$ alkyl optionally substituted with —CN or halogen, wherein R$_x$ is —C$_{1-8}$ alkyl or —C$_{1-8}$ alkyl substituted with one or more halogen.

In another embodiment, the invention provides a compound of formula (I), wherein R$_1$ is alkylheterocyclyl, wherein alkylheterocyclyl is optionally substituted with one or more of R$^a$.

In another embodiment, the invention provides a compound of formula (I), wherein R$_1$ is 2-morpholinoethyl.

In another embodiment, the invention provides a compound of formula (I), wherein R$_1$ is phenyl, pyridyl, quinolinyl or 2-morpholinoethyl, wherein each of phenyl, pyridyl, quinolinyl and 2-morpholinoethyl is optionally substituted with one or more of R$^a$.

In another embodiment, the invention provides a compound of formula (I), wherein R$_1$ is phenyl, pyridyl, quinolinyl or 2-morpholinoethyl, wherein each of phenyl, pyridyl, quinolinyl and 2-morpholinoethyl is optionally substituted with one or more groups selected from halogen, —CN, —OR$_x$, —C$_6$-C$_{14}$ aryl and —C$_1$-C$_8$ alkyl optionally substituted with —CN or halogen, wherein R$_x$ is —C$_{1-8}$ alkyl or —C$_{1-8}$ alkyl substituted with one or more halogen.

In another embodiment, the invention provides a compound of formula (I), wherein R$_2$ is —CN.

In another embodiment, the invention provides a compound of formula (I), wherein R$_3$ is —C$_{1-6}$ alkyl optionally substituted with —CN.

In another embodiment, the invention provides a compound of formula (I), wherein R$_6$ is —C$_6$-C$_{14}$ aryl, heterocyclyl or heteroaryl, wherein each of —C$_6$-C$_{14}$ aryl, heterocyclyl and heteroaryl are optionally substituted with one or more of R$^a$, wherein R$^a$ at each occurrence is halogen, nitro, —CN, —OR$_x$, —S(=O)$_m$R$_x$, —S(=O)$_n$NR$_x$R$_y$, —NR$_x$R$_y$, —NR$_x$COR$_y$, —N(COR$_y$)$_2$, —NR$_x$COOR$_y$, —NR$_x$SOR$_y$, —NR$_x$SO$_2$R$_y$, —NR$_x$CONR$_x$R$_y$, —COR$_x$, —COOR$_x$, —CONR$_x$R$_y$, —(CH$_2$)$_n$NR$_x$COOR$_y$, -oxo-, —NHCH$_2$O(CH$_2$)$_2$OR$_x$, —C$_1$-C$_8$ alkyl, —C$_2$-C$_8$ alkenyl, —C$_2$-C$_8$ alkynyl, —C$_6$-C$_{14}$ aryl, alkylaryl, heterocyclyl, alkylheterocyclyl, heteroaryl or alkylheteroaryl, wherein each of —C$_1$-C$_8$ alkyl, —C$_2$-C$_8$ alkenyl, —C$_2$-C$_8$ alkynyl, —C$_6$-C$_{14}$ aryl, alkylaryl, heterocyclyl, alkylheterocyclyl, heteroaryl and alkylheteroarylaryl is optionally substituted with one or more of R$^b$;

wherein R$_x$ and R$_y$ at each occurrence are independently hydrogen, —C$_1$-C$_8$ alkyl, —C$_2$-C$_8$ alkenyl, —C$_2$-C$_8$ alkynyl, —C$_3$-C$_{10}$ cycloalkyl, alkylcycloalkyl, —C$_6$-C$_{14}$ aryl, alkylaryl, heterocyclyl, alkylheterocyclyl, heteroaryl or alkylheteroaryl, wherein each of —C$_1$-C$_8$ alkyl, —C$_2$-C$_3$ alkenyl, —C$_2$-C$_3$ alkynyl, —C$_3$-C$_{10}$ cycloalkyl, alkylcycloalkyl, —C$_6$-C$_{14}$ aryl, alkylaryl, heterocyclyl, alkylheterocyclyl, heteroaryl and alkylheteroaryl are optionally substituted with R$^b$;

R$^b$ at each occurrence is halogen, nitro, —CN, hydroxy, —C$_1$-C$_8$ alkoxy, —COOH, —C(O)O—C$_1$-C$_3$ alkyl, —NH$_2$ or —C$_1$-C$_8$ alkyl;

m is 0; and n is an integer from 1 to 2.

In another embodiment, the invention provides a compound of formula (I), wherein R$_6$ is heteroaryl optionally substituted with one or more of R$^a$.

In another embodiment, the invention provides a compound of formula (I), wherein R$_6$ is phenyl, napthyl, pyridyl, pyrimidinyl, quinolinyl, benzodioxolyl, pyrrolopyridyl, dihydropyridyl, tetrahydropyrimidyl, indolyl or indazolyl, wherein each of pyridyl, pyrimidinyl, quinolinyl, benzodioxolyl, pyrrolopyridiyl, dihydropyridyl, tetrahydropyrimidyl, indolyl and indazolyl is optionally substituted with one or more of R$^a$, wherein R$^a$ at each occurrence is halogen, nitro, —CN, —OR$_x$, —S(=O)$_m$R$_x$, —S(=O)$_n$NR$_x$R$_y$, —NR$_x$R$_y$, —NR$_x$COR$_y$, —N(COR$_y$)$_2$, —NR$_x$COOR$_y$, —NR$_x$SOR$_y$, —NR$_x$SO$_2$R$_y$, —NR$_x$CONR$_x$R$_y$, —COR$_x$, —COOR$_x$, —CONR$_x$R$_y$, —(CH$_2$)$_n$NR$_x$COOR$_y$, -oxo-, —NHCH$_2$O(CH$_2$)$_2$OR$_x$, —C$_1$-C$_8$ alkyl, —C$_2$-C$_3$ alkenyl, —C$_2$-C$_8$ alkynyl, —C$_6$-C$_{14}$ aryl, alkylaryl, heterocyclyl, alkylheterocyclyl, heteroaryl or alkylheteroaryl, wherein each of —C$_1$-C$_8$ alkyl, —C$_2$-C$_3$ alkenyl, —C$_2$-C$_3$ alkynyl, —C$_6$-C$_{14}$ aryl, alkylaryl, heterocyclyl, alkylheterocyclyl, heteroaryl and alkylheteroarylaryl is optionally substituted with one or more of R$^b$;

wherein R$_x$ and R$_y$ at each occurrence are independently hydrogen, —C$_1$-C$_8$ alkyl, —C$_2$-C$_8$ alkenyl, —C$_2$-C$_8$ alkynyl, —C$_3$-C$_{10}$ cycloalkyl, alkylcycloalkyl, —C$_6$-C$_{14}$ aryl, alkylaryl, heterocyclyl, alkylheterocyclyl, heteroaryl or alkylheteroaryl, wherein each of —C$_1$-C$_8$ alkyl, —C$_2$-C$_8$ alkenyl, —C$_2$-C$_8$ alkynyl, —C$_3$-C$_{10}$ cycloalkyl, alkylcycloalkyl, —C$_6$-C$_{14}$ aryl, alkylaryl, heterocyclyl, alkylheterocyclyl, heteroaryl and alkylheteroaryl are optionally substituted with R$^b$;

R$^b$ at each occurrence is halogen, nitro, —CN, hydroxy, —C$_1$-C$_8$ alkoxy, —COOH, —C(O)O—C$_1$-C$_8$ alkyl, —NH$_2$ or —C$_1$-C$_8$ alkyl;

m is 0; and n is an integer from 1 to 2.

In another embodiment, the invention provides a compound of formula (I), wherein R$_6$ is phenyl, napthyl, pyridyl, pyrimidinyl, quinolinyl, benzodioxolyl, pyrrolopyridyl, dihydropyridyl, tetrahydropyrimidyl, indolyl or indazolyl, wherein each of phenyl, napthyl, pyridyl, pyrimidinyl, quinolinyl, benzodioxolyl, pyrrolopyridyl, dihydropyridyl, tetrahydropyrimidyl, indolyl and indazolyl is optionally substituted with one or more groups selected from —NR$_x$R$_y$, —NR$_x$COOR$_y$, —NR$_x$SO$_2$R$_y$, —NR$_x$COR$_y$, —OR$_x$, —COOR$_x$, —(CH$_2$)$_n$NR$_x$COOR$_y$, —N(COR$_y$)$_2$, —NHCH$_2$O(CH$_2$)$_2$OR$_x$, -oxo-, —CN, —S(=O)$_m$R$_x$, halogen, —C$_1$-C$_8$ alkyl optionally substituted with halogen or heterocyclyl optionally substituted with —C(O)O—C$_1$-C$_8$ alkyl, wherein R$_x$ and R$_y$ are independently selected from hydrogen, —C$_1$-C$_8$ alkyl, —C$_6$-C$_{14}$ aryl or alkylaryl; m is 0 and n is 1.

In another embodiment, the invention provides a compound of formula (I), wherein R$_6$ is pyridyl, optionally substituted with one or more of R$^a$.

In another embodiment, the invention provides a compound of formula (I), wherein R$_6$ is pyridyl, optionally substituted with one or more groups selected from NR$_x$R$_y$, —NR$_x$COOR$_y$, —NR$_x$SO$_2$R$_y$, —NR$_x$COR$_y$, —OR$_x$, —(CH$_2$)$_n$NR$_x$COOR$_y$, —N(COR$_y$)$_2$, —NHCH$_2$O(CH$_2$)$_2$OR$_x$, halogen, —C$_1$-C$_8$ alkyl optionally substituted with halogen and heterocyclyl optionally substituted with —C(O)

O—C$_1$-C$_8$ alkyl, wherein R$_x$ and R$_y$ are independently selected from hydrogen, —C$_1$-C$_8$ alkyl, —C$_6$-C$_{14}$ aryl and alkylaryl and n is 1.

In another embodiment, the invention provides a compound of formula (I), wherein R$_6$ is 3-pyridyl optionally substituted with one or more of R$^a$.

In another embodiment, the invention provides a compound of formula (I), wherein R$_6$ is 3-pyridyl optionally substituted by one or more groups independently selected from halogen, —O—C$_1$-C$_4$ alkyl, —NH$_2$, —NH—C$_1$-C$_4$-alkyl, —N(C$_1$-C$_4$-alkyl)$_2$ and methyl optionally substituted with one to three halogen atoms.

In another embodiment, the invention provides a compound of formula (I), wherein R$^a$ is halogen, —OR$_x$, —S(=O)$_m$R$_x$, —NR$_x$COR$_y$, —NR$_x$COOR$_y$, —NR$_x$SO$_2$R$_y$, —NR$_x$R$_y$, —N(COR$_y$)$_2$, —NHCH$_2$O(CH$_2$)$_2$OR$_x$, —(CH$_2$)$_n$NR$_x$COOR$_y$, -oxo-, —COOR$_x$, —C$_1$-C$_8$ alkyl or heterocyclyl, wherein alkyl and heterocyclyl are optionally substituted with one or more of R$^b$.

In another embodiment, the invention provides a compound of formula (I), wherein R$_x$ is hydrogen, —C$_1$-C$_8$ alkyl, C$_6$-C$_{14}$ aryl or alkylaryl.

In another embodiment, the invention provides a compound of formula (I), wherein R$_y$ is hydrogen.

In another embodiment, the invention provides a compound of formula (I), wherein R$^b$ is selected from —CN or halogen.

Representative compounds, encompassed in accordance with the present invention include:

N-(8-(6-amino-5-(trifluoromethyl)pyridin-3-yl)-1-(6-methoxypyridin-3-yl)-3-methyl-1H-imidazo[4,5-c]quinolin-2(3H)-ylidene)cyanamide, N-(8-(6-(dimethylamino)pyridin-3-yl)-1-(6-methoxypyridin-3-yl)-3-methyl-1H-imidazo[4,5-c]quinolin-2 (3H)-ylidene)cyanamide, N-(1-(6-methoxypyridin-3-yl)-3-methyl-8-(quinolin-3-yl)-1H-imidazo[4,5-c]quinolin-2(3H)-ylidene)cyanamide, N-(8-(6-amino-5-(trifluoromethyl)pyridin-3-yl)-1-(2-chloro-6-methoxypyridin-3-yl)-3-methyl-1H-imidazo[4,5-c]quinolin-2(3H)-ylidene)cyanamide, N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide, N-(8-(6-amino-5-(trifluoromethyl)pyridin-3-yl)-1-(4-(2-cyanopropan-2-yl)phenyl)-3-methyl-1H-imidazo[4,5-c]quinolin-2 (3H)-ylidene)cyanamide, N-(1-(4-(2-cyanopropan-2-yl)phenyl)-3-methyl-8-(quinolin-3-yl)-1H-imidazo[4,5-c]quinolin-2(3H)-ylidene)cyanamide, N-(8-(6-amino-5-(trifluoromethyl)pyridin-3-yl)-3-methyl-1-(2-morpholino ethyl)-1H-imidazo[4,5-c]quinolin-2 (3H)-ylidene)cyanamide, N-(8-(6-amino-5-(trifluoromethyl)pyridin-3-yl)-1-(6-methoxy-2-methylpyridin-3-yl)-3-methyl-1H-imidazo[4,5-c]quinolin-2(3H)-ylidene)cyanamide, N-(8-(6-amino-5-(trifluoromethyl)pyridin-3-yl)-1-(6-cyanopyridin-3-yl)-3-methyl-1H-imidazo[4,5-c]quinolin-2 (3H)-ylidene)cyanamide, N-(8-(6-amino-5-(trifluoromethyl)pyridin-3-yl)-3-methyl-1-(quinolin-6-yl)-1H-imidazo[4,5-c]quinolin-2(3H)-ylidene)cyanamide, N-(1-(4-(2-cyanopropan-2-yl)phenyl)-3-methyl-8-(6-(methylamino)-5-(trifluoromethyl)pyridin-3-yl)-1H-imidazo[4,5-c]quinolin-2(3H)-ylidene)cyanamide, N-(8-(5-amino-6-methoxypyridin-3-yl)-1-(2,4-dimethoxyphenyl)-3-methyl-1H-imidazo[4,5-c]quinolin-2(3H)-ylidene)cyanamide, N-(1-(6-methoxypyridin-3-yl)-3-methyl-8-(pyridin-4-yl)-1H-imidazo[4,5-c]quinolin-2(3H)-ylidene)cyanamide, N-(8-(2-fluoro-5-(trifluoromethyl)phenyl)-1-(6-methoxypyridin-3-yl)-3-methyl-1H-imidazo[4,5-c]quinolin-2(3H)-ylidene)cyanamide, N-(8-(3,5-difluorophenyl)-1-(6-methoxypyridin-3-yl)-3-methyl-1H-imidazo[4,5-c]quinolin-2(3H)-ylidene)cyanamide, N-(8-(Benzo[d][1,3]dioxol-5-yl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-(3,4,5-trimethoxyphenyl)-1H-imidazo[4,5-c]quinolin-2(3H)-ylidene)cyanamide, N-(1-(6-methoxypyridin-3-yl)-3-methyl-8-(naphthalen-2-yl)-1H-imidazo[4,5-c]quinolin-2(3H)-ylidene)cyanamide, N-(1-(6-methoxypyridin-3-yl)-8-(2-methoxypyrimidin-5-yl)-3-methyl-1H-imidazo[4,5-c]quinolin-2(3H)-ylidene)cyanamide, N-(8-(2,4-dimethoxypyrimidin-5-yl)-1-(6-methoxypyridin-3-yl)-3-methyl-1H-imidazo[4,5-c]quinolin-2(3H)-ylidene)cyanamide, N-(8-(2-fluoropyridin-3-yl)-1-(6-methoxypyridin-3-yl)-3-methyl-1H-imidazo[4,5-c]quinolin-2(3H)-ylidene)cyanamide, N-(8-(2,6-difluoropyridin-3-yl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-phenyl-1H-imidazo[4,5-c]quinolin-2(3H)-ylidene)cyanamide, N-(1-(6-methoxypyridin-3-yl)-3-methyl-8-(5-(trifluoromethyl)pyridin-3-yl)-1H-imidazo[4,5-c]quinolin-2(3H)-ylidene)cyanamide, N-(1-(6-methoxypyridin-3-yl)-3-methyl-8-(quinolin-7-yl)-1H-imidazo[4,5-c]quinolin-2(3H)-ylidene)cyanamide, N-(8-(2-isopropoxyphenyl)-1-(6-methoxypyridin-3-yl)-3-methyl-1H-imidazo[4,5-c]quinolin-2(3H)-ylidene)cyanamide, N-(8-(3-chlorophenyl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-m-tolyl-1H-imidazo[4,5-c]quinolin-2(3H)-ylidene)cyanamide, N-(8-(4-cyanophenyl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-(4-phenoxyphenyl)-1H-imidazo[4,5-c]quinolin-2(3H)-ylidene)cyanamide, N-(8-(2-chlorophenyl)-1-(6-methoxypyridin-3-yl)-3-methyl-1H-imidazo[4,5-c]quinolin-2(3H)-ylidene)cyanamide, N-(8-(3-methoxyphenyl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-o-tolyl-1H-imidazo[4,5-c]quinolin-2(3H)-ylidene)cyanamide, N-(8-(isoquinolin-4-yl)-1-(6-methoxypyridin-3-yl)-3-methyl-1H-imidazo[4,5-c]quinolin-2(3H)-ylidene)cyanamide, N-(8-(3,4-dimethoxyphenyl)-1-(6-methoxypyridin-3-yl)-3-methyl-1H-imidazo[4,5-c]quinolin-2(3H)-ylidene)cyanamide, N-(8-(4-(isopropylthio)phenyl)-1-(6-methoxypyridin-3-yl)-3-methyl-1H-imidazo[4,5-c]quinolin-2(3H)-ylidene)cyanamide, N-(8-(3-hydroxyphenyl)-1-(6-methoxypyridin-3-yl)-3-methyl-1H-imidazo[4,5-c]quinolin-2(3H)-ylidene)cyanamide,
N-(8-(4-fluoropyridin-3-yl)-1-(6-methoxypyridin-3-yl)-3-methyl-1H-imidazo[4,5-c]quinolin-2(3H)-ylidene)cyanamide,
N-(8-(3-fluorophenyl)-1-(6-methoxypyridin-3-yl)-3-methyl-1H-imidazo[4,5-c]quinolin-2(3H)-ylidene)cyanamide,
N-(1-(6-methoxypyridin-3-yl)-3-methyl-8-(3-(trifluoromethyl)phenyl)-1H-imidazo[4,5-c]quinolin-2(3H)-ylidene)cyanamide,
N-(8-(2,6-dimethylphenyl)-1-(6-methoxypyridin-3-yl)-3-methyl-1H-imidazo[4,5-c]quinolin-2(3H)-ylidene)cyanamide,
N-(1-(6-methoxypyridin-3-yl)-3-methyl-8-(4-(trifluoromethyl)phenyl)-1H-imidazo[4,5-c]quinolin-2(3H)-ylidene)cyanamide,
N-(1-(6-methoxypyridin-3-yl)-3-methyl-8-p-tolyl-1H-imidazo[4,5-c]quinolin-2(3H)-ylidene)cyanamide,
N-(1-(6-methoxypyridin-3-yl)-3-methyl-8-(2-methylpyridin-3-yl)-1H-imidazo[4,5-c]quinolin-2(3H)-ylidene)cyanamide,
N-(8-(4-hydroxyphenyl)-1-(6-methoxypyridin-3-yl)-3-methyl-1H-imidazo[4,5-c]quinolin-2(3H)-ylidene)cyanamide,
N-(8-(5-fluoro-2-methoxyphenyl)-1-(6-methoxypyridin-3-yl)-3-methyl-1H-imidazo[4,5-c]quinolin-2(3H)-ylidene)cyanamide,
N-(1,8-bis(6-methoxypyridin-3-yl)-3-methyl-1H-imidazo[4,5-c]quinolin-2(3H)-ylidene)cyanamide,
N-(8-(2-methoxyphenyl)-1-(6-methoxypyridin-3-yl)-3-methyl-1H-imidazo[4,5-c]quinolin-2(3H)-ylidene)cyanamide,
N-(1-(6-(2-cyanopropan-2-yl)pyridin-3-yl)-8-(4-hydroxyphenyl)-3-methyl-1H-imidazo[4,5-c]quinolin-2(3H)-ylidene)cyanamide,
N-(1-(6-(2-cyanopropan-2-yl)pyridin-3-yl)-8-(6-methoxypyridin-3-yl)-3-methyl-1H-imidazo[4,5-c]quinolin-2(3H)-ylidene)cyanamide,
N-(1-(6-(2-cyanopropan-2-yl)pyridin-3-yl)-8-(5-fluoro-2-methoxyphenyl)-3-methyl-1H-imidazo[4,5-c]quinolin-2(3H)-ylidene)cyanamide,
N-(1-(6-(2-cyanopropan-2-yl)pyridin-3-yl)-8-(2-methoxyphenyl)-3-methyl-1H-imidazo[4,5-c]quinolin-2(3H)-ylidene)cyanamide,
N-(8-(benzo[d][1,3]dioxol-5-yl)-1-(6-(2-cyanopropan-2-yl)pyridin-3-yl)-3-methyl-1H-imidazo[4,5-c]quinolin-2(3H)-ylidene)cyanamide,
N-(1-(6-(2-cyanopropan-2-yl)pyridin-3-yl)-8-(2,4-dimethoxy pyrimidin-5-yl)-3-methyl-1H-imidazo[4,5-c]quinolin-2(3H)-ylidene)cyanamide,
N-(1-(6-(2-cyanopropan-2-yl)pyridin-3-yl)-3-methyl-8-(quinolin-6-yl)-1H-imidazo[4,5-c]quinolin-2(3H)-ylidene)cyanamide,
N-(1-(6-(2-cyanopropan-2-yl)pyridin-3-yl)-3-methyl-8-(3,4,5-trimethoxyphenyl)-1H-imidazo[4,5-c]quinolin-2(3H)-ylidene)cyanamide,
N-(8-(benzo[d][1,3]dioxol-5-yl)-1-(6-methoxy-2-methylpyridin-3-yl)-3-methyl-1H-imidazo[4,5-c]quinolin-2(3H)-ylidene)cyanamide,
N-(1-(6-methoxy-2-methylpyridin-3-yl)-3-methyl-8-(3,4,5-trimethoxyphenyl)-1H-imidazo[4,5-c]quinolin-2(3H)-ylidene)cyanamide,
N-(1-(6-(2-cyanopropan-2-yl)pyridin-3-yl)-3-methyl-8-(1H-pyrrolo[2,3-b]pyridin-5-yl)-1H-imidazo[4,5-c]quinolin-2(3H)-ylidene)cyanamide,
N-(8-(6-aminopyridin-3-yl)-1-(6-(2-cyanopropan-2-yl)pyridin-3-yl)-3-methyl-1H-imidazo[4,5-c]quinolin-2(3H)-ylidene)cyanamide,
N-(1-(6-(2-cyanopropan-2-yl)pyridin-3-yl)-3-methyl-8-(naphthalen-2-yl)-1H-imidazo[4,5-c]quinolin-2(3H)-ylidene)cyanamide,
N-(1-(6-(2-cyanopropan-2-yl)pyridin-3-yl)-8-(3,5-difluorophenyl)-3-methyl-1H-imidazo[4,5-c]quinolin-2(3H)-ylidene)cyanamide,
N-(1-(6-(2-cyanopropan-2-yl)pyridin-3-yl)-8-(2-fluoropyridin-3-yl)-3-methyl-1H-imidazo[4,5-c]quinolin-2(3H)-ylidene)cyanamide,
N-(1-(6-(2-cyanopropan-2-yl)pyridin-3-yl)-8-(2-isopropoxyphenyl)-3-methyl-1H-imidazo[4,5-c]quinolin-2(3H)-ylidene)cyanamide,
N-(1-(6-(2-cyanopropan-2-yl)pyridin-3-yl)-8-(3,4-dimethoxyphenyl)-3-methyl-1H-imidazo[4,5-c]quinolin-2(3H)-ylidene)cyanamide,
N-(1-(6-(2-cyanopropan-2-yl)pyridin-3-yl)-3-methyl-8-p-tolyl-1H-imidazo[4,5-c]quinolin-2(3H)-ylidene)cyanamide,
N-(1-(6-(2-cyanopropan-2-yl)pyridin-3-yl)-3-methyl-8-(4-(trifluoromethyl)phenyl)-1H-imidazo[4,5-c]quinolin-2(3H)-ylidene)cyanamide,
N-(1-(6-(2-cyanopropan-2-yl)pyridin-3-yl)-3-methyl-8-(3-(trifluoromethyl)phenyl)-1H-imidazo[4,5-c]quinolin-2(3H)-ylidene)cyanamide,
N-(1-(6-(2-cyanopropan-2-yl)pyridin-3-yl)-3-methyl-8-(5-(trifluoromethyl)pyridin-3-yl)-1H-imidazo[4,5-c]quinolin-2(3H)-ylidene)cyanamide,
tert-butyl (5-(2-(cyanoimino)-1-(6-(2-cyanopropan-2-yl)pyridin-3-yl)-3-methyl-2,3-dihydro-1H-imidazo[4,5-c]quinolin-8-yl)pyridin-3-yl)methylcarbamate,
tert-butyl 4-(5-(2-(cyanoimino)-1-(6-(2-cyanopropan-2-yl)pyridin-3-yl)-3-methyl-2,3-dihydro-1H-imidazo[4,5-c]quinolin-8-yl)pyridin-2-yl)piperazine-1-carboxylate,
N-(1-(6-(2-cyanopropan-2-yl)pyridin-3-yl)-8-(1H-indol-5-yl)-3-methyl-1H-imidazo[4,5-c]quinolin-2(3H)-ylidene)cyanamide,
N-(8-(5-chloro-6-methoxypyridin-3-yl)-1-(6-(2-cyanopropan-2-yl)pyridin-3-yl)-3-methyl-1H-imidazo[4,5-c]quinolin-2(3H)-ylidene)cyanamide,
N-(8-(2-aminopyrimidin-5-yl)-1-(6-(2-cyanopropan-2-yl)pyridin-3-yl)-3-methyl-1H-imidazo[4,5-c]quinolin-2(3H)-ylidene)cyanamide,
N-(1-(6-(2-cyanopropan-2-yl)pyridin-3-yl)-3-methyl-8-(6-(piperidin-1-yl)pyridin-3-yl)-1H-imidazo[4,5-c]quinolin-2(3H)-ylidene)cyanamide,
N-(1-(6-(2-cyanopropan-2-yl)pyridin-3-yl)-8-(1H-indazol-6-yl)-3-methyl-1H-imidazo[4,5-c]quinolin-2(3H)-ylidene)cyanamide,
N-(1-(6-(2-cyanopropan-2-yl)pyridin-3-yl)-8-(6-fluoro-5-methylpyridin-3-yl)-3-methyl-1H-imidazo[4,5-c]quinolin-2(3H)-ylidene)cyanamide,
N-(1-(6-(2-cyanopropan-2-yl)pyridin-3-yl)-8-(1H-indol-6-yl)-3-methyl-1H-imidazo[4,5-c]quinolin-2(3H)-ylidene)cyanamide,
N-(1-(6-(2-cyanopropan-2-yl)pyridin-3-yl)-8-(4-fluorophenyl)-3-methyl-1H-imidazo[4,5-c]quinolin-2(3H)-ylidene)cyanamide,
N-(1-(6-(2-cyanopropan-2-yl)pyridin-3-yl)-3-methyl-8-(pyridin-4-yl)-1H-imidazo[4,5-c]quinolin-2(3H)-ylidene)cyanamide,
N-(1-(6-(2-cyanopropan-2-yl)pyridin-3-yl)-3-methyl-8-(naphthalen-1-yl)-1H-imidazo[4,5-c]quinolin-2(3H)-ylidene)cyanamide, N-(8-(6-amino-5-(trifluoromethyl)pyridin-3-yl)-1-(4-(2-cyanopropan-2-yl)phenyl)-1H-imidazo[4,5-c]quinolin-2(3H)-ylidene)cyanamide,
N-(8-(5-amino-6-methoxypyridin-3-yl)-1-(4-(2-cyanopropan-2-yl)phenyl)-3-methyl-1H-imidazo[4,5-c]quinolin-2(3H)-ylidene)cyanamide,
N-(1-(4-(2-cyanopropan-2-yl)phenyl)-8-(pyridin-3-yl)-1H-imidazo[4,5-c]quinolin-2(3H)-ylidene)cyanamide,
N-(1-(4-(2-cyanopropan-2-yl)phenyl)-3-ethyl-8-(pyridin-3-yl)-1H-imidazo[4,5-c]quinolin-2(3H)-ylidene)cyanamide,
N-(1-(4-(2-cyanopropan-2-yl)phenyl)-8-(2-fluoro-5-(trifluoromethyl)phenyl)-3-methyl-1H-imidazo[4,5-c]quinolin-2(3H)-ylidene)cyanamide,
N-(1-(4-(2-cyanopropan-2-yl)phenyl)-3-methyl-8-(3,4,5-trimethoxyphenyl)-1H-imidazo[4,5-c]quinolin-2(3H)-ylidene)cyanamide,
tert-butyl 4-(2-(cyanoimino)-1-(4-(2-cyanopropan-2-yl)phenyl)-3-methyl-2,3-dihydro-1H-imidazo[4,5-c]quinolin-8-yl)-5,6-dihydropyridine-1(2H)-carboxylate,
N-(1-(4-(2-cyanopropan-2-yl)phenyl)-3-methyl-8-(6-morpholinopyridin-3-yl)-1H-imidazo[4,5-c]quinolin-2(3H)-ylidene)cyanamide,
N-(1-(4-(2-cyanopropan-2-yl)phenyl)-8-(6-methoxypyridin-3-yl)-3-methyl-1H-imidazo[4,5-c]quinolin-2(3H)-ylidene)cyanamide,
N-(8-(6-amino-5-(trifluoromethyl)pyridin-3-yl)-3-methyl-1-(5-phenylpyridin-3-yl)-1H-imidazo[4,5-c]quinolin-2(3H)-ylidene)cyanamide,
N-(8-(5-amino-6-methoxypyridin-3-yl)-3-methyl-1-(5-phenylpyridin-3-yl)-1H-imidazo[4,5-c]quinolin-2(3H)-ylidene)cyanamide,
N-(1-(4-(2-cyanopropan-2-yl)phenyl)-8-(1H-indol-6-yl)-3-methyl-1H-imidazo[4,5-c]quinolin-2(3H)-ylidene)cyanamide,
N-(8-(5-amino-6-methoxypyridin-3-yl)-1-(6-(2-cyanopropan-2-yl)pyridin-3-yl)-3-methyl-1H-imidazo[4,5-c]quinolin-2(3H)-ylidene)cyanamide,
N-(8-(6-amino-5-(trifluoromethyl)pyridin-3-yl)-1-(6-(2-cyanopropan-2-yl)pyridin-3-yl)-1H-imidazo[4,5-c]quinolin-2(3H)-ylidene)cyanamide,
N-(8-(6-amino-5-(trifluoromethyl)pyridin-3-yl)-1-(3,5-dimethoxyphenyl)-3-methyl-1H-imidazo[4,5-c]quinolin-2(3H)-ylidene)cyanamide,
N-(8-(6-amino-5-(trifluoromethyl)pyridin-3-yl)-1-(2,6-dimethoxypyridin-3-yl)-3-methyl-1H-imidazo[4,5-c]quinolin-2(3H)-ylidene)cyanamide,
N-(8-(5-amino-6-methoxypyridin-3-yl)-1-(3,5-dimethoxyphenyl)-3-methyl-1H-imidazo[4,5-c]quinolin-2(3H)-ylidene)cyanamide,
N-(1-(2,4-dimethoxyphenyl)-3-methyl-8-(quinolin-3-yl)-1H-imidazo[4,5-c]quinolin-2(3H)-ylidene)cyanamide,
N-(1-(2,4-dimethoxyphenyl)-3-methyl-8-(pyridin-3-yl)-1H-imidazo[4,5-c]quinolin-2(3H)-ylidene)cyanamide,
N-(1-(3,5-dimethoxyphenyl)-3-methyl-8-(pyridin-3-yl)-1H-imidazo[4,5-c]quinolin-2(3H)-ylidene)cyanamide,
N-(1-(2,4-dimethoxyphenyl)-3-methyl-8-(quinolin-6-yl)-1H-imidazo[4,5-c]quinolin-2(3H)-ylidene)cyanamide,
N-(1-(2,4-dimethoxyphenyl)-3-methyl-8-(4-(trifluoromethyl)phenyl)-1H-imidazo[4,5-c]quinolin-2(3H)-ylidene)cyanamide,
N-(8-(6-amino-5-(trifluoromethyl)pyridin-3-yl)-3-methyl-1-(4-(trifluoromethoxy)phenyl)-1H-imidazo[4,5-c]quinolin-2(3H)-ylidene)cyanamide,
N-(8-(5-amino-6-methoxypyridin-3-yl)-3-methyl-1-(4-(trifluoromethoxy)phenyl)-1H-imidazo[4,5-c]quinolin-2(3H)-ylidene)cyanamide,
N-(3-methyl-8-(quinolin-3-yl)-1-(4-(trifluoromethoxy)phenyl)-1H-imidazo[4,5-c]quinolin-2(3H)-ylidene)cyanamide,
N-(3-methyl-8-(pyridin-3-yl)-1-(4-(trifluoromethoxy)phenyl)-1H-imidazo[4,5-c]quinolin-2(3H)-ylidene)cyanamide,
N-(3-methyl-8-(pyridin-4-yl)-1-(4-(trifluoromethoxy)phenyl)-1H-imidazo[4,5-c]quinolin-2(3H)-ylidene)cyanamide,
N-(8-(6-amino-5-(trifluoromethyl)pyridin-3-yl)-3-(cyanomethyl)-1-(6-(2-cyanopropan-2-yl)pyridin-3-yl)-1H-imidazo[4,5-c]quinolin-2(3H)-ylidene)cyanamide,
N-(8-(6-amino-5-(trifluoromethyl)pyridin-3-yl)-3-methyl-1-(6-(trifluoromethyl)pyridin-3-yl)-1H-imidazo[4,5-c]quinolin-2(3H)-ylidene)cyanamide,
N-(3-methyl-8-(6-morpholinopyridin-3-yl)-1-(6-(trifluoromethyl)pyridin-3-yl)-1H-imidazo[4,5-c]quinolin-2(3H)-ylidene)cyanamide,
N-(8-(6-methoxypyridin-3-yl)-3-methyl-1-(6-(trifluoromethyl)pyridin-3-yl)-1H-imidazo[4,5-c]quinolin-2(3H)-ylidene)cyanamide,
N-(8-(1H-indol-5-yl)-3-methyl-1-(6-(trifluoromethyl)pyridin-3-yl)-1H-imidazo[4,5-c]quinolin-2(3H)-ylidene)cyanamide,
N-(1-(6-(2-cyanopropan-2-yl)pyridin-3-yl)-8-(4-(isopropylthio)phenyl)-3-methyl-1H-imidazo[4,5-c]quinolin-2(3H)-ylidene)cyanamide,
N-(8-(4-(butylthio) phenyl)-1-(6-(2-cyanopropan-2-yl)pyridin-3-yl)-3-methyl-1H-imidazo[4,5-c]quinolin-2(3H)-ylidene)cyanamide,
tert-butyl 4-(2-(cyanoimino)-1-(6-(2-cyanopropan-2-yl)pyridin-3-yl)-3-methyl-2,3-dihydro-1H-imidazo[4,5-c]quinolin-8-yl)-5,6-dihydropyridine-1(2H)-carboxylate,
tert-butyl 4-(2-(cyanoimino)-3-methyl-1-(6-(trifluoromethyl)pyridin-3-yl)-2,3-dihydro-1H-imidazo[4,5-c]quinolin-8-yl)-5,6-dihydropyridine-1(2H)-carboxylate,
tert-butyl 4-(5-(2-(cyanoimino)-1-(6-(2-cyanopropan-2-yl)pyridin-3-yl)-3-methyl-2,3-dihydro-1H-imidazo[4,5-c]quinolin-8-yl)-3-methylpyridin-2-yl)piperazine-1-carboxylate,
N-(1-(6-(2-cyanopropan-2-yl)pyridin-3-yl)-8-(2,4-dioxo-1,2,3,4-tetrahydropyrimidin-5-yl)-3-methyl-1H-imidazo[4,5-c]quinolin-2(3H)-ylidene)cyanamide,
N-(8-(3-chloro-2-morpholinopyridin-4-yl)-1-(6-(2-cyanopropan-2-yl)pyridin-3-yl)-3-methyl-1H-imidazo[4,5-c]quinolin-2(3H)-ylidene)cyanamide,
tert-butyl 5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-ylcarbamate,
tert-butyl 5-(2-(cyanoimino)-1-(6-methoxypyridin-3-yl)-3-methyl-2,3-dihydro-1H-imidazo[4,5-c]quinolin-8-yl)-3-(trifluoromethyl)pyridin-2-ylcarbamate,
N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)benzenesulfonamide,
N-(5-(2-(cyanoimino)-1-(6-(2-cyanopropan-2-yl)pyridin-3-yl)-3-methyl-2,3-dihydro-1H-imidazo[4,5-c]quinolin-8-yl)-2-methoxypyridin-3-yl)benzenesulfonamide,
N-(5-(2-(cyanoimino)-1-(6-(2-cyanopropan-2-yl)pyridin-3-yl)-3-methyl-2,3-dihydro-1H-imidazo[4,5-c]quinolin-8-yl)-2-methoxypyridin-3-yl)methane sulfonamide,
N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)methanesulfonamide,
N-(5-(2-(cyanoimino)-1-(6-(2-cyanopropan-2-yl)pyridin-3-yl)-3-methyl-2,3-dihydro-1H-imidazo[4,5-c]quinolin-8-yl)-4-methylpyridin-2-yl)acetamide, N-(1-(4-(2-cyanopropan-2-yl)phenyl)-8-(6-(dimethylamino)-5-(trifluoromethyl)pyridin-3-yl)-3-methyl-1H-imidazo[4,5-c]quinolin-2(3H)-ylidene)cyanamide, N-(1-(6-(2-cyanopropan-2-yl)pyridin-3-yl)-8-(6-((2-methoxyethoxy)methylamino)-5-(trifluoromethyl)pyridin-3-yl)-3-methyl-1H-imidazo[4,5-c]quinolin-2(3H)-ylidene)cyanamide, N-acetyl-N-(5-(2-(cyanoimino)-1-(4-(2-cyanopropan-2-yl)phenyl)-3-methyl-2,3-dihydro-1H-imidazo[4,5-c]quinolin-8-yl)-3-(trifluoromethyl)pyridin-2-yl)acetamide, N-acetyl-N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-yl)acetamide, 2-(cyanoimino)-1-(4-(2-cyanopropan-2-yl)phenyl)-3-methyl-2,3-dihydro-1H-imidazo[4,5-c]quinolin-8-yl)-3-(trifluoromethyl)pyridin-2-yl)acetamide, N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-yl)acetamide, N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)-2,4-difluorobenzenesulfonamide, N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-yl)-2-propylpentanamide, Methyl 2-amino-5-(2-(cyanoimino)-1-(6-(2-cyanopropan-2-yl)pyridin-3-yl)-3-methyl-2,3-dihydro-1H-imidazo[4,5-c]quinolin-8-yl)nicotinate, N-(8-(6-(benzylamino)-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide, and pharmaceutically acceptable salts, stereoisomers, tautomers and N-oxides thereof.

Methods of Preparation

The compounds of formula (I) can be prepared using various procedures, some of which are depicted in the schemes below. Those with skill in the art will appreciate that the specific starting compounds and reagents, such as bases, solvents, coupling agents; temperature conditions etc. identified in the Schemes can be altered to prepare compounds encompassed by the present invention.

Scheme 1

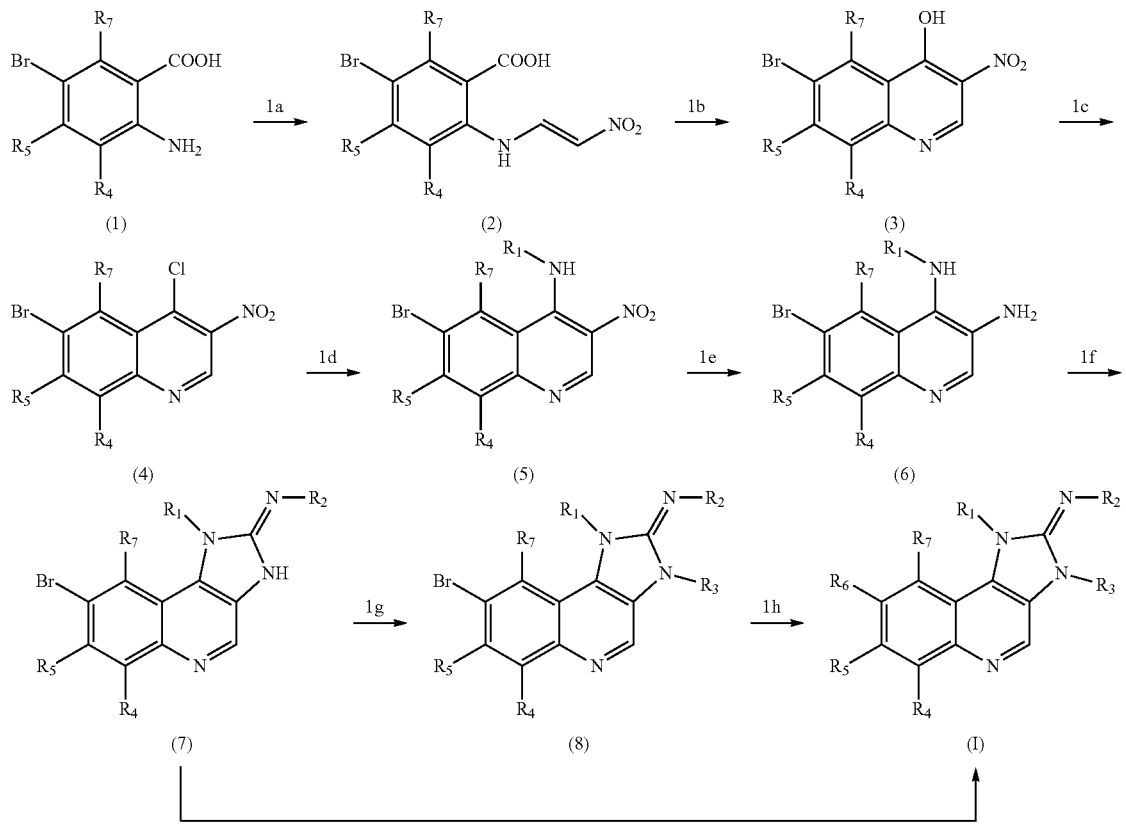

wherein $R_1$, $R_4$, $R_5$, $R_6$ and $R_7$ are as defined in any one of the embodiments of the invention for the compounds of formula (I), $R_2$ is —CN and $R_3$ is H, methyl or —CH$_2$CN.

As illustrated in scheme 1, compound of formula (2), wherein $R_4$, $R_5$ and $R_7$ are as defined for formula (I) can be prepared by reacting nitromethane in presence of a base such as NaOH at 0° C. to RT; then adding the product to concentrated HCl at 0-10° C. and adding the compound of the formula (I) in aqueous acid such as water-HCl mixture, and stirring at 0° C. to room temperature. The nitro compound of formula (2) can be reacted with an acid anhydride such as acetic anhydride in presence of an alkali metal salt such as potassium acetate or sodium acetate at 80-140° C. to form compound of formula (3). The nitro-quinolinol compound of formula (3) can be treated with halogenating agent, for example with chlorinating agent such as POCl$_3$ at 80-140° C.

to form compound of formula (4). The compound of formula (4) can be treated with an amine of formula $R_1$—$NH_2$ (wherein $R_1$ is as defined in any one of the embodiments of the invention for the compounds of formula (I)) at 0-40° C. to form a compound of formula (5). Catalytic reduction of nitro group of compound of formula (5) forms quinoline-diamine of formula (6). The quinoline-diamine of formula (6) is coupled with a reagent such as diphenylcyanocarbonimidate or dimethyl cyanocarbonimidodithioate in presence of a base such as diisopropylethylamine or cesium carbonate and in a solvent such as acetonitrile or dimethylformamide to form a compound of formula (7), wherein $R_1$, $R_4$, $R_5$ and $R_7$ are as defined above and $R_2$ is —CN. The compound of formula (7) can be treated with a methylating agent such as methyl iodide or with bromoacetonitrile in presence of a base such as sodium hydride to form a compound of formula (8), wherein $R_1$, $R_4$, $R_5$ and $R_7$ are as defined above, $R_2$ is —CN and $R_3$ is methyl or —$CH_2CN$. The compound of formula (8) or compound of formula (7) can be further treated with a compound of formula $R_6$—$B(OH)_3$ in presence of a coupling agent such as palladium dichlorobistriphenylphosphine and a base such as sodium carbonate to form a compound of formula (I), wherein $R_1$, $R_4$, $R_5$, $R_6$ and $R_7$ are as defined in any one of the embodiments of the invention for the compounds of formula (I), $R_2$ is —CN and $R_3$ is H, methyl or —$CH_2CN$.

The process of the present invention described herein comprises an optional step of forming a salt and/or a solvate of the compound of formula (I).

Isotopically labeled forms of compounds of formula (I), can be prepared by conventional techniques known to those skilled in the art or by processes analogous to those described above and in the subsequent Experimental section by using an appropriate isotopically labeled reagent instead of non-labeled reagent.

The pharmaceutically acceptable salts of the present invention can be synthesized from the compound of formula (I), which contains a basic or an acidic moiety, by conventional chemical methods. Generally the salts are prepared by contacting the free base or acid with an appropriate amount of the desired salt-forming inorganic or organic acid or base in a suitable solvent or dispersant, or from another salt by cation or anion exchange. Suitable solvents are, for example, ethyl acetate, ether, alcohols, acetone, tetrahydrofuran, dioxane or mixtures of these solvents. These salts can also be used for purification of the compounds obtained.

According to a further aspect of the present invention, there is provided a process for the preparation of a compound of formula (I) and its salt.

According to a further aspect of the present invention, there is provided a process for the preparation of a compound of formula (7), wherein $R_2$ is —CN; $R_4$, $R_5$ and $R_7$ are hydrogen and $R_1$ is as defined in any one of the embodiments of the invention for the compounds of formula (I),

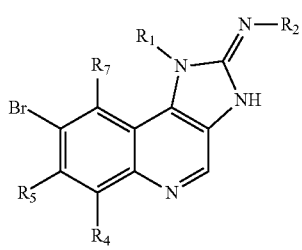

(7)

comprising,
reacting a compound of formula (6)

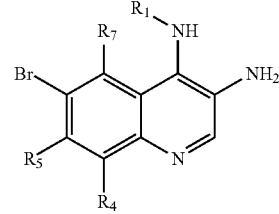

(6)

wherein, $R_4$, $R_5$ and $R_7$ are hydrogen and $R_1$ is as defined in any one of the embodiments of the invention for the compounds of formula (I), with a reagent such as diphenylcyanocarbonoimidate or dimethyl cyanocarbonimidodithioate in presence of a base such as diisopropylethylamine or cesium carbonate.

According to a further aspect of the present invention, there is provided a process for the preparation of a compound of formula (8) wherein $R_2$ is —CN; $R_3$ is methyl or —$CH_2CN$; $R_4$, $R_5$ and $R_7$ are hydrogen; and $R_1$ is as defined in any one of the embodiments of the invention for the compounds of formula (I),

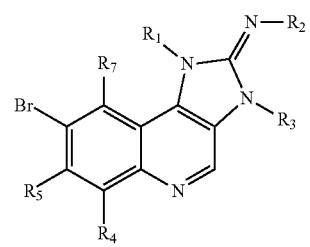

(8)

comprising,
reacting a compound of formula (7)

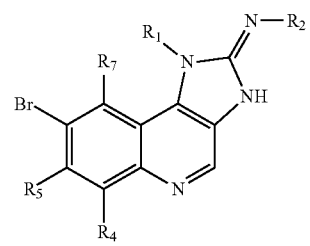

(7)

wherein, $R_2$ is —CN; $R_4$, $R_5$ and $R_7$ are hydrogen and $R_1$ is as defined in any one of the embodiments of the invention for the compounds of formula (I), with a methylating agent such as methyliodide or bromoacetonitrile in presence of base such as sodium hydride.

According to a further aspect of the present invention, there is provided a process for the preparation of a compound of formula (I), wherein, $R_2$ is —CN; $R_3$ is methyl or —$CH_2CN$; $R_4$, $R_5$ and $R_7$ are hydrogen; $R_1$ and $R_6$ are as defined in any one of the embodiments of the invention for the compounds of formula (I),

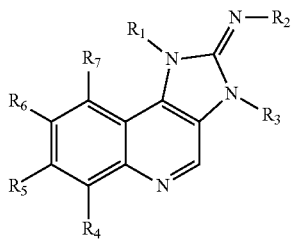

formula (I)

comprising,
reacting a compound of formula (8)

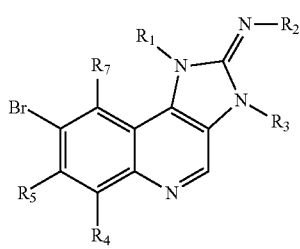

(8)

with a compound of formula $R_6$—$BOH_3$ in presence of a coupling agent such as palladium dichlorobis triphenylphosphine, in presence of a base such as sodium carbonate, wherein, $R_2$ is —CN; $R_3$ is methyl or —$CH_2CN$; $R_4$, $R_5$ and $R_7$ are hydrogen; $R_1$ and $R_6$ are as defined for formula (I).

The compounds of formula (I) can be converted to corresponding pharmaceutically acceptable salts.

Methods of Treatment

Compounds of the present invention inhibit the activity of kinases including PI3K, mTOR, DNA-PK and ALK1, and can be used in the treatment of diseases mediated by the said kinases.

Compounds of the present invention can be used to reduce, inhibit or diminish the proliferation of tumor cells, and thereby assist in reducing the size of a tumor.

Compounds of the present invention can be used for the treatment of inflammatory disorder and angiogenesis related disorders.

Proliferative disease or disorder that can be treated using compounds of formula (I) is cancer, including, but not limited to, leukemia such as acute lymphocytic leukemia; acute myeloid leukemia; adult acute myeloid leukemia; acute lymphoblastic leukemia; chronic lymphocytic leukemia; chronic myeloid leukemia; hairy cell leukemia, lung cancer including non-small-cell lung cancer and small-cell lung cancer, brain tumors such as brain stem glioma; glioblastoma; astrocytoma including cerebellar astrocytoma and cerebral astrocytoma, visual pathway and hypothalamic glioma; supratentorial primitive neuroectodermal and pineal tumors; medulloblastoma, lymphoma such as primary central nervous system lymphoma; non-Hodgkin's lymphoma particularly mantle cell lymphoma, Hodgkin's disease, liver cancer such as hepatocellular carcinoma, kidney cancer such as renal cell carcinoma and Wilms' tumor, sarcoma such as Ewing's sarcoma family of tumors; osteosarcoma; rhabdomyosarcoma; soft tissue sarcomas, mesothelioma, bladder cancer, breast cancer, endometrial cancer, head and neck cancer, melanoma, cervical cancer, thyroid cancer, gastric cancer, germ cell tumor, cholangiocarcinoma, extracranial cancer, malignant fibrous histiocytoma of bone, retinoblastoma, esophageal cancer, multiple myeloma, oral cancer, pancreatic cancer, ependymoma, neuroblastoma, skin cancer, ovarian cancer, recurrent ovarian cancer, prostate cancer, testicular cancer, colorectal cancer, lymphoproliferative disease, refractory multiple myeloma, resistant multiple myeloma and myeloproliferative disorder, or a combination of one or more of the preceding cancers.

Inflammatory diseases or disorders that can be treated using compounds of formula (I) include, but are not limited to, rheumatoid arthritis, juvenile rheumatoid arthritis, psoriatic arthritis, osteoarthritis, refractory rheumatoid arthritis, chronic non-rheumatoid arthritis, osteoporosis, bone resorption, septic shock, Crohn's disease, inflammatory bowel disease, ulcerative colitis, atherosclerosis and psoriasis.

Compounds of the present invention may also be used for the treatment of other diseases or conditions, such as contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, inflammation, septic shock, endotoxic shock, atherosclerosis, ischaemia-reperfusion injury, coronary heart disease, vasculitis, amyloidosis, multiple sclerosis, sepsis, chronic recurrent uveitis, hepatitis C virus infection, malaria, ulcerative colitis, cachexia, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, diabetes, juvenile diabetes, meningitis, ankylosing spondylitis, skin delayed type hypersensitivity disorders, Alzheimer's disease, systemic lupus erythematosus, allergic asthma and bronchitis.

Compounds of the present invention can be used for the treatment of angiogenesis related disorders.

Compounds of the present invention may also be used for the treatment of diseases in which angiogenesis is found to be important, referred to as angiogenic diseases, including but not limited to, inflammatory disorders such as immune and non-immune inflammation, chronic articular rheumatism, psoriasis, disorders associated with inappropriate or inopportune invasion of vessels such as diabetic retinopathy, neovascular glaucoma, capillary proliferation in atherosclerotic plaques and osteoporosis, and cancer associated disorders, such as solid tumors, solid tumor metastases, angiofibromas, retrolental fibroplasia, hemangiomas, Kaposi's sarcoma and the like cancers which require neovascularization to support tumor growth.

The following abbreviations and definitions are used throughout this application:

The term "tumor" as used herein refers to an abnormal growth of tissue resulting from uncontrolled, progressive multiplication of cells. A tumor can be benign or malignant.

The term "cancer" as used herein refers to malignant tumor.

ABBREVIATIONS

PI3 kinase phosphatidylinositol-3-kinase
mTOR mammalian target of rapamycin
DNA-PK DNA-dependent protein kinase
MAP4K2 mitogen-activated protein kinase kinase kinase kinase 2
ALK1 (also known as ACVRL1) activin receptor-like kinase 1
ALK2 (also known as ACVR1) activin A receptor, type I CLK1 CDC-like kinase 1
CLK4 CDC-like kinase 4
JAK2 Janus kinase 2
MAP4K5 mitogen-activated protein kinase kinase kinase kinase 5
MuSK muscle-specific receptor tyrosine kinase
RIPK2 receptor-interacting serine/threonine-protein kinase 2
ROS reactive oxygen species According to another aspect of the present invention, there is provided a method for the treatment of diseases or disorders selected from proliferative diseases, inflammatory diseases or disorders and angiogenesis related disorders.

According to another aspect of the present invention, there is provided a method for the treatment of diseases or disorders that can be treated by inhibiting one or more kinases such as PI3 kinase, mTOR or ALK-1.

According to another aspect of the present invention, there is provided a method for the treatment of proliferative diseases or disorders, inflammatory diseases or disorders or angiogenesis related disorders that can be treated by inhibiting one or more kinases such as PI3 kinase, mTOR or ALK-1.

According to another aspect of the present invention, there is provided a method for the treatment of proliferative diseases or disorders mediated by one or more kinases, such as PI3K, mTOR or ALK-1, comprising administering to a mammal in need thereof a therapeutically effective amount of a compound of formula (I) or a pharmaceutically acceptable salt, a stereoisomer, a tautomer or N-oxide thereof.

According to another aspect of the present invention, the proliferative disease mediated by one or more kinases is cancer.

According to another aspect of the present invention, the cancer is solid cancer or hematological cancer.

According to another embodiment of the present invention, the cancer is leukemia such as acute lymphocytic leukemia; acute myeloid leukemia; adult acute myeloid leukemia; acute lymphoblastic leukemia; chronic lymphocytic leukemia; chronic myeloid leukemia; hairy cell leukemia, lung cancer including non-small-cell lung cancer and small-cell lung cancer, brain tumors such as brain stem glioma; glioblastoma; astrocytoma including cerebellar astrocytoma and cerebral astrocytoma, visual pathway and hypothalamic glioma; supratentorial primitive neuroectodermal and pineal tumors; medulloblastoma, lymphoma such as primary central nervous system lymphoma; non-Hodgkin's lymphoma particularly mantle cell lymphoma, Hodgkin's disease, liver cancer such as hepatocellular carcinoma, kidney cancer such as renal cell carcinoma and Wilms' tumor, sarcoma such as Ewing's sarcoma family of tumors; osteosarcoma; rhabdomyosarcoma; soft tissue sarcomas, mesothelioma, bladder cancer, breast cancer, endometrial cancer, head and neck cancer, melanoma, cervical cancer, thyroid cancer, gastric cancer, germ cell tumor, cholangiocarcinoma, extracranial cancer, malignant fibrous histiocytoma of bone, retinoblastoma, esophageal cancer, multiple myeloma, oral cancer, pancreatic cancer, ependymoma, neuroblastoma, skin cancer, ovarian cancer, recurrent ovarian cancer, prostate cancer, testicular cancer, colorectal cancer, lymphoproliferative disease, refractory multiple myeloma, resistant multiple myeloma and myeloproliferative disorder, or a combination of one or more of the preceding cancers.

According to another embodiment of the present invention, the cancer is leukemia, lung cancer, brain tumors, Hodgkin's disease, liver cancer, kidney cancer, bladder cancer, breast cancer, head and neck cancer, endometrial cancer, lymphoma, melanoma, cervical cancer, thyroid cancer, gastric cancer, germ cell tumor, cholangiocarcinoma, extracranial cancer, sarcoma, mesothelioma, malignant fibrous histiocytoma of bone, retinoblastoma, esophageal cancer, multiple myeloma, oral cancer, pancreatic cancer, neuroblastoma, skin cancer, ovarian cancer, recurrent ovarian cancer, prostate cancer, testicular cancer, colorectal cancer, lymphoproliferative disease, refractory multiple myeloma, cancer of urinary tract, resistant multiple myeloma or myeloproliferative disorder.

According to another embodiment of the present invention, the cancer is breast cancer, prostate cancer, pancreatic cancer, lung cancer, head and neck cancer, ovarian cancer, colorectal cancer, kidney cancer, gastric cancer, non-Hodgkin's lymphoma, primary central nervous system lymphoma, endometrial cancer, brain tumors, melanoma, liver cancer, thyroid cancer, lymphoid cancer, esophageal cancer, cancer of urinary tract, cervical cancer, bladder cancer, mesothelioma, sarcoma or chronic myeloid leukemia.

According to another embodiment of the present invention, the cancer is breast cancer, prostate cancer, pancreatic cancer, lung cancer, ovarian cancer, colorectal cancer, kidney cancer, brain tumor, liver cancer, thyroid cancer, lymphoid cancer, gastric cancer, head & neck cancer, melanoma, mesothelioma, bladder cancer or chronic myeloid leukemia.

According to another aspect of the present invention, there is provided a method for the treatment of inflammatory diseases or disorders mediated by one or more kinases, including, but not limited to, PI3 kinase and mTOR, comprising administering to a mammal in need thereof a therapeutically effective amount of a compound of formula (I) or a pharmaceutically acceptable salt, a stereoisomer, a tautomer or N-oxide thereof.

According to another aspect of the present invention, the inflammatory disease or disorder is selected from rheumatoid arthritis, Crohn's disease, ulcerative colitis, inflammatory bowel disease, chronic non-rheumatoid arthritis, osteoporosis, septic shock, psoriasis or atherosclerosis.

According to another aspect of the present invention, there is provided a method for the treatment of angiogenesis related disorders mediated by one or more kinases, including but not limited to, PI3 kinase, ALK-1 and mTOR, comprising administering to a mammal in need thereof a therapeutically effective amount of a compound of formula (I) or a pharmaceutically acceptable salt, a stereoisomer, a tautomer or N-oxide thereof.

According to another aspect of the present invention, there is provided a method for the treatment of angiogenesis related disorders mediated by VEGF, comprising administering to a mammal in need thereof a therapeutically effective amount of a compound of formula (I) or a pharmaceutically acceptable salt, a stereoisomer, a tautomer or N-oxide thereof.

According to another aspect of the present invention, the angiogenesis related disorder is an inflammatory disorder.

According to another aspect of the present invention, the inflammatory disorder which is an angiogenesis related disorder is selected from immune and non-immune inflammation, chronic articular rheumatism, disorders associated with inappropriate or inopportune invasion of vessels such as diabetic retinopathy, neovascular glaucoma, capillary proliferation in atherosclerotic plaques or osteoporosis.

According to another aspect of the present invention, the angiogenesis related disorder is cancer associated disorder, such as solid tumor, solid tumor metastasis, angiofibroma, retrolental fibroplasia, hemangioma or Kaposi's sarcoma.

According to another aspect of the present invention, there is provided the use of a compound of formula (I) or a pharmaceutically acceptable salt, a stereoisomer, a tautomer or N-oxide thereof for the treatment of a proliferative disease, an inflammatory disease or angiogenesis related disorder.

According to another aspect of the present invention, there is provided the use of a compound of formula (I) or a pharmaceutically acceptable salt, a stereoisomer, a tautomer or N-oxide thereof for the treatment of proliferative disease mediated by one or more kinases such as PI3K, mTOR or ALK-1.

According to another aspect of the present invention, there is provided the use of a compound of formula (I) or a pharmaceutically acceptable salt, a stereoisomer, a tautomer or N-oxide thereof for the treatment of cancer selected from leukemia such as acute lymphocytic leukemia; acute myeloid leukemia; adult acute myeloid leukemia; acute lymphoblastic leukemia; chronic lymphocytic leukemia; chronic myeloid leukemia; hairy cell leukemia, lung cancer including non-small-cell lung cancer and small-cell lung cancer, brain tumors such as brain stem glioma; glioblastoma; astrocytoma including cerebellar astrocytoma and cerebral astrocytoma, visual pathway and hypothalamic glioma; supratentorial primitive neuroectodermal and pineal tumors; medulloblastoma, lymphoma such as primary central nervous system lymphoma; non-Hodgkin's lymphoma particularly mantle cell lymphoma, Hodgkin's disease, liver cancer such as hepatocellular carcinoma, kidney cancer such as renal cell carcinoma and Wilms' tumor, sarcoma such as Ewing's sarcoma family of tumors; osteosarcoma; rhabdomyosarcoma; soft tissue sarcomas, mesothelioma, bladder cancer, breast cancer, endometrial cancer, head and neck cancer, melanoma, cervical cancer, thyroid cancer, gastric cancer, germ cell tumor, cholangiocarcinoma, extracranial cancer, malignant fibrous histiocytoma of bone, retinoblastoma, esophageal cancer, multiple myeloma, oral cancer, pancreatic cancer, ependymoma, neuroblastoma, skin cancer, ovarian cancer, recurrent ovarian cancer, prostate cancer, testicular cancer, colorectal cancer, lymphoproliferative disease, refractory multiple myeloma, resistant multiple myeloma and myeloproliferative disorder, or a combination of one or more of the preceding cancers.

According to another aspect of the present invention, there is provided the use of a compound of formula (I) or a pharmaceutically acceptable salt, a stereoisomer, a tautomer or N-oxide thereof for the treatment of cancer selected from leukemia, lung cancer, brain tumors, Hodgkin's disease, liver cancer, kidney cancer, bladder cancer, breast cancer, endometrial cancer, head and neck cancer, lymphoma, melanoma, cervical cancer, thyroid cancer, gastric cancer, germ cell tumor, cholangiocarcinoma, extracranial cancer, sarcoma, mesothelioma, malignant fibrous histiocytoma of bone, retinoblastoma, esophageal cancer, multiple myeloma, oral cancer, pancreatic cancer, neuroblastoma, skin cancer, ovarian cancer, recurrent ovarian cancer, prostate cancer, testicular cancer, colorectal cancer, lymphoproliferative disease, refractory multiple myeloma, cancer of urinary tract, resistant multiple myeloma and myeloproliferative disorder.

According to another aspect of the present invention, there is provided the use of a compound of formula (I) or a pharmaceutically acceptable salt, a stereoisomer, a tautomer or N-oxide thereof for the treatment of cancer selected from breast cancer, prostate cancer, pancreatic cancer, lung cancer, head and neck cancer, ovarian cancer, colorectal cancer, kidney cancer, gastric cancer, non-Hodgkin's lymphoma, primary central nervous system lymphoma, endometrial cancer, brain tumor, melanoma, liver cancer, thyroid cancer, lymphoid cancer, esophageal cancer, cancer of urinary tract, cervical cancer, bladder cancer, mesothelioma, sarcoma or chronic myeloid leukemia.

According to another aspect of the present invention, there is provided the use of a compound of formula (I) or a pharmaceutically acceptable salt, a stereoisomer, a tautomer or N-oxide thereof for the treatment of cancer selected from breast cancer, prostate cancer, pancreatic cancer, lung cancer, ovarian cancer, colorectal cancer, kidney cancer, brain tumor, liver cancer, thyroid cancer, lymphoid cancer, gastric cancer, head & neck cancer, melanoma, mesothelioma, bladder cancer or chronic myeloid leukemia.

According to another aspect of the present invention, there is provided the use of a compound of formula (I) or a pharmaceutically acceptable salt, a stereoisomer, a tautomer or N-oxide thereof for the treatment of inflammatory disease selected from rheumatoid arthritis, Crohn's disease, ulcerative colitis, inflammatory bowel disease, chronic non-rheumatoid arthritis, osteoporosis, septic shock, psoriasis or atherosclerosis.

According to another aspect of the present invention, there is provided the use of a compound of formula (I) or a pharmaceutically acceptable salt, a stereoisomer, a tautomer or N-oxide thereof for the treatment of angiogenesis related disorder mediated by VEGF or ALK-1.

According to another aspect of the present invention there is provided use of a compound of formula (I) or a pharmaceutically acceptable salt, a stereoisomer, a tautomer or N-oxide thereof, for the preparation of medicament for the treatment of proliferative disease, inflammatory disease or angiogenesis related disorder.

According to another aspect of the present invention there is provided use of a compound of formula (I) or a pharmaceutically acceptable salt, a stereoisomer, a tautomer or N-oxide thereof for the preparation of medicament for the treatment of proliferative disease.

According to another aspect of the present invention there is provided use of a compound of formula (I) or a pharmaceutically acceptable salt, a stereoisomer, a tautomer or N-oxide thereof for the preparation of a medicament for the treatment of inflammatory disease.

According to another aspect of the present invention there is provided use of a compound of formula (I) or a pharmaceutically acceptable salt, a stereoisomer, a tautomer or N-oxide thereof for the peparation of a medicament for the treatment of angiogenesis related disorders.

Pharmaceutical Compositions and Methods

The pharmaceutical preparations according to the invention are prepared in a manner known per se and familiar to one skilled in the art. Pharmaceutically acceptable inert inorganic and/or organic carriers and/or additives can be used in addition to the compounds of formula (I), and/or their pharmaceutically acceptable salts. For the production of pills, tablets, coated tablets and hard gelatin capsules it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or for emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, for example, about 5 to 70%, or from about 5 to about 30% by weight of the compound of the formula (I) or pharmaceutically acceptable salt thereof. The amount of the active ingredient i.e. the compound of the formula (I) or a pharmaceutically acceptable salt thereof in the pharmaceutical preparations normally is from about 1 to 1000 mg.

The dose of the compounds of this invention, which is to be administered, can cover a wide range. The dose to be administered daily is to be selected to produce the desired effect. A suitable dosage is about 0.001 to 100 mg/kg of the compound of formula (I) or pharmaceutically acceptable salt thereof, for example, about 0.01 to 20 mg/kg of a compound of formula (I) or a pharmaceutically acceptable salt thereof. If required, higher or lower daily doses can also be administered. Actual dosage levels of the active ingredients in the pharmaceutical compositions of this invention may be varied so as to obtain an amount of the active ingredient, which is effective to achieve the desired therapeutic response for a particular patient.

The pharmaceuticals preparations can be administered orally, for example in the form of pills, tablets, coated tablets, lozenges, capsules, dispersible powders or granules, suspensions, emulsions, syrups or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or ointments or transdermally, for example in the form of transdermal patches, or in other ways, for example in the form of aerosols, nasal sprays or nasal drops.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredient i.e. the compound of formula (I) and/or its pharmaceutically acceptable salt and carrier substances, the pharmaceutical preparations can contain additives such as, for example, fillers, antioxidants, dispersants, emulsifiers, defoamers, flavors, preservatives, solubilizers or colorants. They can also contain one or more compounds of the formula (I) and/or their pharmaceutically acceptable salts.

Furthermore, in addition to at least one compound of the formula (I) and/or its pharmaceutically acceptable salt.

By "pharmaceutically acceptable" it is meant the carrier, diluent, excipients, and/or salt must be compatible with the other ingredients of the formulation, and not deleterious to the recipient thereof.

According to another aspect of the present invention there is provided a pharmaceutical composition, comprising a therapeutically effective amount of a compound of formula (I) or a pharmaceutically acceptable salt thereof in association with a pharmaceutically acceptable excipient or carrier.

According to another aspect of the present invention there is provided a method for the manufacture of a medicament useful for the treatment of proliferative disease, inflammatory disease or angiogenesis related disorder, comprising a compound of formula (I) or a pharmaceutically acceptable salt thereof in association with a pharmaceutically acceptable excipient or carrier.

It is understood that modifications that do not substantially affect the activity of the various embodiments of this invention are included within the invention disclosed herein. Accordingly, the following examples are intended to illustrate but not to limit the present invention.

Experimental

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims. For example, the synthesis of non-exemplified compounds according to the invention may be successfully performed by modifications apparent to those skilled in the art.

Nomenclature of the compounds exemplified in the present invention was derived from Chemdraw Ultra version 9.0.1 CambridgeSoft Corporation, Cambridge.

Reagents were purchased from commercial suppliers such as Sigma Aldrich Chemical company, Spectrochem Ltd., India; AK scientific Inc; CA, Thomas Baker (Chemicals) Pvt. Ltd., India; Frontier Scientific Inc; UT and Merck Chemicals and were are used as such.

Unless otherwise stated all temperatures are in degree Celsius. Also, in these examples and elsewhere, abbreviations have the following meanings:

| List of abbreviations | |
|---|---|
| ATP | Adenosine triphosphate |
| BSA | Bovine Serum Albumin |
| $CO_2$ | Carbon dioxide |
| $CHCl_3$ | Chloroform |
| cpm | Counts per minute |
| DCM | Dichloromethane |
| DMF | Dimethyl formamide |
| DMSO | Dimethyl sulfoxide |
| EDTA | Ethylene Diamine Tetraacetic Acid |
| EtOAc | Ethyl acetate |
| h | hour(s) |
| g | Gram |
| HCl | Hydrochloric acid |
| $MgCl_2$ | Magnesium chloride |
| mL | Milliliter |
| mmol | Millimolar |
| MeOH | Methanol |
| µM | micro Molar |
| MOPSO | 3-(N-Morpholino)-2-hydroxypropanesulfonic Acid |
| NaCl | Sodium Chloride |
| NaH | Sodium hydride |
| $NaHCO_3$ | Sodium bicarbonate |
| NaOH | Sodium hydroxide |
| $Na_2SO_4$ | Sodium sulphate |
| nM | nano Molar |
| psi | pound per square inch |
| $POCl_3$ | Phosphorus oxychloride |
| PBS | Phosphate buffer saline |
| RT | Room Temperature (20-30° C.) |
| THF | Tetrahydrofuran |
| TBS | Tris Buffered Saline |

Method for Preparation of Salts
Method A: General Method for Preparation of Methane Sulfonic Acid Salts
A solution of compound of formula (I) (0.106 mmol) in dry dichloromethane (5 ml) was stirred at 0° C. Methane sulfonic acid (0.01021 g, 106 mmol) dissolved in dry dichloromethane (1 ml) was added drop-wise to the solution of the compound over a period of 0.5 h. Reaction mixture was stirred at same temperature for 0.5 h, warmed to RT, and stirred further for 4 h. Solvent was removed and the methane sulfonic acid salt of the compound of formula (I) was obtained. The salt so obtained was characterized by NMR.

Method B: General Method for Preparation of 4-Methylbenzene Sulfonic Acid Salts

A solution of compound of formula (I) (0.106 mmol) in dry dichloromethane (5 ml) was stirred at 0° C. 4-methylbenzene sulfonic acid (0.01021 g, 106 mmol) dissolved in dry dichloromethane (1 ml) was added drop-wise to the solution of the compound over a period of 0.5 h. Reaction mixture was stirred at same temperature for 0.5 h, warmed to RT room temperature, and stirred further for 4 h. Solvent was removed and the mesylate salt of the compound of formula (I) was obtained. The salt so obtained was characterized by NMR.

Method C: General Method for Preparation of Hydrochloride Salts

A solution of compound of formula (I) (0.106 mmol) in dry dichloromethane (5 ml) was stirred at 0° C. Ethereal HCl was added in excess to the solution of the compound. Reaction mixture was stirred at same temperature for 0.5 h, warmed to RT and further stirred for 4 h. Solvent was removed and the hydrochloride salt of the compound of formula (I) was obtained. The salt so obtained was characterized by NMR.

EXAMPLES

Example 1

N-(8-(6-amino-5-(trifluoromethyl)pyridin-3-yl)-1-(6-methoxypyridin-3-yl)-3-methyl-1H-imidazo[4,5-c]quinolin-2(3H)-ylidene)cyanamide Step 1: 6-Bromo-4-chloro-3-nitroquinoline A: 5-Bromo-2-(2-nitrovinylamino)benzoic acid A suspension of 2-Amino-5-bromobenzoic acid (231 mmol) in water-HCl (37%) (10:1) was stirred for 8 h and was filtered (solution 1). Nitromethane (278 mmol) was added over 10 minutes to a mixture of ice (70 g) and NaOH (775 mmol) at 0° C. under stirring. After stirring for 1 h at 0° C. and 1 h at RT, this solution was added to a mixture of ice (56 g) and 84 mL of HCl (37%) at 0° C. (solution 2). Solution 1 and 2 were combined and the reaction mixture was stirred for 18 h at RT. The yellow precipitate was filtered, washed with water and dried at 40° C. to obtain the title compound. The crude product was used directly for the next step.

Yield: 38%.

B: 6-Bromo-3-nitroquinolin-4-ol

5-Bromo-2-(2-nitrovinylamino)benzoic acid (Compound A, 87 mmol) and potassium acetate (104 mmol) in acetic anhydride (1185 mmol) were stirred for 3 h at 120° C. The precipitate was filtered, and washed with acetic acid till the filtrate was colorless. It was further washed with water and dried to obtain the title compound. $^1$H NMR (CDCl$_3$, 500 MHz): δ 9.275 (s, 1H), 8.611-8.615 (d, 1H, J=2 Hz), 8.100-8.118 (d, 1H, J=9 Hz), 8.026-8.048 (dd, 1H, J=8.5 Hz, 2 Hz).

C: 6-Bromo-4-chloro-3-nitroquinoline

6-Bromo-3-nitroquinolin-4-ol (compound B, 74.3 mmol) and POCl$_3$ (1613 mmol) were stirred for 45 minutes at 120° C. The mixture was cooled to RT and poured slowly into ice-water. The precipitate was filtered, washed with ice-cold water, and dissolved in CH$_2$Cl$_2$. The organic layer was washed with cold brine, and was dried over Na$_2$SO$_4$. The solvent was evaporated to dryness to obtain the title compound. The crude product was used directly for the next step.

Step 2: 6-bromo-N-(6-methoxypyridin-3-yl)-3-nitro-quinolin-4-amine

6-Bromo-4-chloro-3-nitroquinoline (compound of step 1, 5.2 mmol) and 6-methoxypyridin-3-amine (commercially available, 5.2 mmol) was dissolved in acetic acid (5 mL) and the mixture was stirred overnight. Water was added and the yellow precipitate was filtered off. The precipitate was washed with water and dried. The solid obtained was partitioned and extracted with EtOAc and THF, washed with saturated aqueous NaHCO$_3$. The organic layer was dried over anhydrous sodium sulfate and concentrated to obtain the title compound. $^1$H NMR (DMSO-d$_6$, 300 MHz): 10.03 (s, 1H), 9.01 (s, 1H), 8.72 (d, J=1.5 Hz, 1H), 8.04-7.90 (m, 3H), 7.50 (dd, J=2.4, 8.7 Hz, 1H), 6.82 (d, J=9.0 Hz, 1H), 3.85 (s, 3H); MS (m/z): 377.0 (M+1)$^+$.

Step 3: 6-bromo-N$^4$-(6-methoxypyridin-3-yl)quinoline-3,4-diamine 6-bromo-N-(6-methoxypyridin-3-yl)-3-nitroquinolin-4-amine (compound of step 2, 13.3 mmol) was hydrogenated using Raney-Ni (1 g) in THF-MeOH [(1:1), 50 mL] under 40 psi of hydrogen for 4 h at RT. After completion of the reaction, the reaction mixture was filtered through celite and washed with methanol. The filtrate was concentrated and purified (silica gel column, MeOH/CHCl$_3$ as eluent) to obtain the title compound. $^1$H NMR (300 MHz, DMSO-d$_6$): δ 8.59 (s, 1H), 7.93 (d, J=2.1 Hz, 1H), 7.78 (d, J=8.7 Hz, 3H), 7.47 (dd, J=2.1, 9.0 Hz, 2H), 6.93 (dd, J=3.0, 8.7 Hz, 1H), 6.65 (d, J=9.0 Hz, 1H), 5.42 (s, 2H), 3.85 (s, 3H); MS (m/z): 345.0 (M+1)$^+$.

Step 4: N-(8-bromo-1-(6-methoxypyridin-3-yl)-1H-imidazo[4,5-c]quinolin-2(3H)-ylidene)cyanamide Diphenyl cyano carbonimidate (3.48 mmol) was added to a solution of 6-bromo-N$^4$-(6-methoxypyridin-3-yl)quinoline-3,4-diamine (compound of step 3, 2.90 mmol) in dry acetonitrile (10 ml), followed by the addition of di-isopropyl ethyl amine (4.35 mmol). The resulting reaction mixture was refluxed for 48 h. The reaction mixture was cooled to RT, concentrated under vacuum and purified (silica gel column, MeOH/CHCl$_3$ as eluent) to obtain the title compound. $^1$H NMR (300 MHz, DMSO-d$_6$): δ 13.81 (s, 1H), 8.96 (s, 1H), 8.53 (d, J=3 Hz, 1H), 8.10 (d, J=3 Hz, 1H), 8.06 (d, J=9 Hz, 1H), 7.80 (dd, J=9 Hz, 3 Hz, 1H), 7.20 (d, J=9 Hz, 1H), 7.13 (d, J=3 Hz, 1H), 4.00 (s, 3H); MS (m/z): 395 (M+1)$^+$.

Step 5: N-(8-bromo-1-(6-methoxypyridin-3-yl)-3-methyl-1H-imidazo[4,5-c]quinolin-2(3H)-ylidene)cyanamide To a solution of N-(8-bromo-1-(6-methoxypyridin-3-yl)-1H-imidazo[4,5-c]quinolin-2(3H)-ylidene)cyanamide (compound of step 4, 0.674 mmol) in 5 ml of dry DMF at 0° C. was added NaH (60% dispersed in mineral oil, 1.011 mmol). The reaction mixture was stirred for 15 minutes followed by addition of methyl iodide (1.011 mmol). Reaction mixture was stirred at 0° C. for another 1 h and quenched with water. The solvent was removed; aqueous layer was extracted with DCM. Organic layer was dried over anhydrous Na$_2$SO$_4$, concentrated under vacuum and purified (silica gel column, MeOH/CHCl$_3$ as eluent) to obtain the title compound. $^1$H NMR (300 MHz, DMSO-d$_6$): δ 9.27 (s, 1H), 8.62 (d, J=3 Hz, 1H), 8.37 (d, J=1.8 Hz, 1H), 8.18 (dd, J=9 Hz, 3 Hz, 1H), 8.08 (d, J=9 Hz, 1H), 7.80 (dd, J=9 Hz, 3 Hz, 1H), 7.21 (d, J=9 Hz, 1H), 7.03 (d, J=3 Hz, 1H), 4.01 (s, 3H), 3.83 (s, 3H); MS (m/z): 409 (M+1)$^+$.

Step 6:
6-amino-5-(trifluoromethyl)pyridin-3-ylboronic acid

A: 5-bromo-3-(trifluoromethyl)pyridin-2-amine 3-(trifluoromethyl)pyridin-2-amine (20 g, 123 mmol) was stirred in acetic acid (200 ml) at RT. Bromine (19.72 g, 123 mmol) was added drop wise with stirring. The reaction mixture was stirred for 2 h; followed by dilution with water. The product was extracted with ethyl acetate. Organic layer was washed with water, dried over sodium sulfate and concentrated to obtain the title product in 74% yield.

B: 6-amino-5-(trifluoromethyl)pyridin-3-ylboronic acid 5-bromo-3-(trifluoromethyl)pyridin-2-amine (9.85 mmol, commercially available), Bis(pinacolato)diboron (11.82 mmol), potassium acetate (1.4 g) and (1,1-bis(diphenylphosphino)ferrocene)-dichloropalladium (II) complex with DCM (200 mg, commercially available) was dissolved in dioxane (75 mL) under argon atmosphere. The reaction mixture was refluxed for 8 h. The reaction mixture was cooled, diluted with ethyl acetate (75 mL) and filtered. The filtrate was concentrated. The crude product was purified over silica gel using 0-10% ethyl acetate in petroleum ether to obtain the titled boronic acid derivative.

Step 7: N-(8-(6-amino-5-(trifluoromethyl)pyridin-3-yl)-1-(6-methoxypyridin-3-yl)-3-methyl-1H-imidazo[4,5-c]quinolin-2(3H)-ylidene)cyanamide 6-amino-5-(trifluoromethyl)pyridin-3-ylboronic acid (1.677 mmol) and palladium dichlorobis triphenylphosphine (10 mol %) were added to a solution of N-(8-bromo-1-(6-methoxypyridin-3-yl)-3-methyl-1H-imidazo[4,5-c]quinolin-2(3H)-ylidene)cyanamide (compound of step 5, 1.118 mmol) in dry DMF in an inert atmosphere. Saturated Na$_2$CO$_3$ (0.3 ml) was added to the reaction mixture and the resulting solution was heated at 110° C. for 3 h. The solvent was removed; the crude material was extracted in EtOAc, washed with brine and dried over anhydrous Na$_2$SO$_4$. The solvent was evaporated and the crude solid was purified (silica gel column, EtOAc/MeOH as eluent) to obtain the title compound. $^1$H NMR (300 MHz, DMSO-d$_6$): δ 9.20 (s, 1H), 8.66 (d, J=3 Hz, 1H), 8.38 (d, J=3 Hz, 1H), 8.22 (m, 2H), 8.06 (dd, J=9 Hz, 3 Hz, 1H), 7.55 (s, 1H), 7.19 (d, J=9 Hz, 1H), 7.03 (d, J=3 Hz, 1H), 6.79 (s, 2H), 3.99 (s, 3H), 3.84 (s, 3H); MS (m/z): 491.2 (M+1)$^+$.

Example 2

N-(8-(6-(dimethylamino)pyridin-3-yl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.16 (s, 1H), 8.67 (d, J=2.4 Hz, 1H), 8.22 (dd, J=8.7, 2.4 Hz, 1H), 8.14 (d, J=9.3 Hz, 2H), 7.95 (dd, J=8.7, 1.2 Hz, 1H), 7.51 (dd, J=9, 2.4 Hz, 1H), 7.23 (d, J=8.7 Hz, 1H), 6.96 (s, 1H), 6.68 (d, J=9 Hz, 1H), 4.04 (s, 3H), 3.83 (s, 3H), 3.06 (s, 6H); MS (m/z): 451 (M+1)$^+$.

Example 3

N-(1-(6-methoxypyridin-3-yl)-3-methyl-8-(quinolin-3-yl)-1H-imidazo[4,5-c]quinolin-2(3H)-ylidene) cyanamide $^1$H NMR (300 MHz, DMSO-d$_6$): δ 9.27 (s, 1H), 8.95 (d, J=1.8 Hz, 1H), 8.71 (d, J=2.7 Hz, 1H), 8.37 (d, J=1.8 Hz, 1H), 8.30 (m, 3H), 8.08 (d, J=8.4 Hz, 1H), 7.99 (d, J=7.8 Hz, 1H), 7.84 (t, J=6.9 Hz, 1H), 7.72 (t, J=7.2 Hz, 1H), 7.27 (m, 2H), 4.02 (s, 3H), 3.86 (s, 3H); MS (m/z): 458.2 (M+1)$^+$.

Example 4

N-(8-(6-amino-5-(trifluoromethyl)pyridin-3-yl)-1-(2-chloro-6-methoxypyridin-3-yl)-3-methyl-1H-imidazo[4,5-c]quinolin-2(3H)-ylidene)cyanamide The title compound was prepared by following the procedure as described for Example 1, except that 2-chloro-6-methoxypyridin-3-amine was used instead of 6-methoxypyridin-3-amine $^1$H NMR (300 MHz, DMSO-d$_6$): δ 9.27 (s, 1H), 8.44 (d, J=8.7 Hz, 1H), 8.40 (d, J=1.8 Hz, 1H), 8.18 (d, J=9.0 Hz, 1H), 8.08 (dd, J=1.8, 9.0 Hz, 1H), 7.58 (d, J=1.8 Hz, 1H), 7.25 (d, J=8.7 Hz, 1H), 7.00 (d, J=1.5 Hz, 1H), 6.83 (s, 2H), 4.03 (s, 3H), 4.00 (s, 3H); MS (m/z): 525.1 (M+1)$^+$.

Example 5

N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide Preparation of 2-(5-aminopyridin-2-yl)-2-methylpropanenitrile Step 1:
2-methyl-2-(5-nitropyridin-2-yl)propanenitrile Sodium hydride (67.44 mmol) was added to a solution of 2-(5-nitropyridine-2-yl)acetonitrile (30.65 mmol) in dry THF (250 ml) at 0° C. and the reaction mixture was stirred for 0.5 h. Methyl iodide (91.95 mmol) was added to the reaction mixture and reaction mixture was warmed to RT, stirred for another 24 h. Solvent was removed under vacuum; crude product was purified (silica gel column, EtOAc/hexane as eluent) to obtain the title compound. $^1$H NMR (300 MHz, DMSO-d$_6$): δ 9.43 (d, J=2.7 Hz, 1H), 8.55 (dd, J=8.7, 2.4 Hz, 1H), 7.86 (d, J=8.7 Hz, 1H), 1.82 (s, 6H); MS (m/z): 192 (M+1)$^+$.

Step 2:
2-(5-aminopyridin-2-yl)-2-methylpropanenitrile 2-methyl-2-(5-nitropyridin-2-yl)propanenitrile (15.70 mmol) was subjected to hydrogenation using Raney-Ni (0.6 g) at 40 psi for 4 h. Reaction mixture was filtered and washed with methanol. Filtrate was concentrated and purified (silica gel column, MeOH/CHCl$_3$ as eluent) to obtain the title compound. $^1$H NMR (300 MHz, DMSO-d$_6$): δ 8.11 (d, J=2.7 Hz, 1H), 7.37 (d, J=8.7 Hz, 1H), 7.03 (dd, J=2.7, 8.7 Hz, 1H), 3.36 (brs, 2H), 1.74 (s, 6H); MS m/z: 162 (M+1)$^+$.

The title compound of Example 5 was prepared by following the procedure as described for Example 1, except that 2-(5-aminopyridin-2-yl)-2-methylpropanenitrile was used instead of 6-methoxypyridin-3-amine. $^1$H NMR (300 MHz, DMSO-d$_6$): δ 9.23 (s, 1H), 9.07 (d, J=2.1 Hz, 1H), 8.50 (m, 1H), 8.19 (d, J=9 Hz, 2H), 8.01 (d, J=7.8 Hz, 2H), 7.75 (m, 1H), 6.90 (d, J=1.8 Hz, 1H), 6.75 (s, 2H), 3.92 (s, 3H), 1.80 (s, 6H); MS (m/z): 528.2 (M+1)$^+$.

Example 6

N-(8-(6-amino-5-(trifluoromethyl)pyridin-3-yl)-1-(4-(2-cyanopropan-2-yl)phenyl)-3-methyl-1H-imidazo[4,5-c]quinolin-2(3H)-ylidene)cyanamide The title compound was prepared by following the procedure as described for Example 1, except that 2-(4-aminophenyl)-2-methylpropanenitrile was used instead of 6-methoxypyridin-3-amine $^1$H NMR (300 MHz, DMSO-d$_6$): δ 9.19 (s, 1H), 8.16 (d, J=8.4 Hz, 2H), 7.98 (dd, J=9, 1.8 Hz, 1H), 7.87 (s, 4H), 7.64 (s, 1H), 6.90 (s, 1H), 6.73 (s, 2H), 3.91 (s, 3H), 1.79 (s, 6H); MS (m/z): 527.2 (M+1)$^+$.

Example 7

N-(1-(4-(2-cyanopropan-2-yl)phenyl)-3-methyl-8-(quinolin-3-yl)-1H-imidazo[4,5-c]quinolin-2(3H)-ylidene)cyanamide The title compound was prepared by following the procedure as described for Example 1, except that 2-(4-aminophenyl)-2-methylpropanenitrile was used instead of 6-methoxypyridin-3-amine and quinolin-3-ylboronic acid was used instead of 6-amino-5-(trifluoromethyl)pyridin-3-ylboronic acid. $^1$H NMR (300 MHz, DMSO-d$_6$): δ 9.26 (s, 1H), 8.71 (d, J=2.7 Hz, 1H), 8.41 (s, 1H), 8.28 (d, J=9 Hz, 1H), 8.19 (d, J=8.7 Hz, 1H), 8.03 (d, J=8.4 Hz, 2H), 7.92 (s, 1H), 7.82 (t, J=7.2 Hz, 1H), 7.68 (t, J=7.2 Hz, 2H) 7.09 (s, 1H), 3.89 (s, 3H), 1.82 (s, 6H); MS (m/z): 494.2 (M+1)$^+$.

Example 8

N-(8-(6-amino-5-(trifluoromethyl)pyridin-3-yl)-3-methyl-1-(2-morpholinoethyl)-1H-imidazo[4,5-c]quinolin-2(3H)-ylidene)cyanamide The title compound was prepared by following the procedure as described for Example 1, except that 2-morpholinoethanamine was used instead of 6-methoxypyridin-3-amine. $^1$H NMR (300 MHz, DMSO-d$_6$): δ 9.09 (s, 1H), 8.78 (s, 1H), 8.43 (s, 1H), 8.24 (s, 1H), 8.17 (d, J=8.7 Hz, 1H), 8.07 (d, J=10.2 Hz, 1H), 6.77 (s, 2H), 4.70-4.90 (m, 2H), 4.08=4.10 (m, 1H), 3.99 (s, 3H), 3.50-3.51 (m, 4H), 3.17 (d, J=4.5 Hz, 3H), 2.80-2.75 (m, 2H); MS (m/z): 497.2 (M+1)$^+$.

Example 9

N-(8-(6-amino-5-(trifluoromethyl)pyridin-3-yl)-1-(6-methoxy-2-methylpyridin-3-yl)-3-methyl-1H-imidazo[4,5-c]quinolin-2(3H)-ylidene)cyanamide The title compound was prepared by following the procedure as described for Example 1, except that 6-methoxy-2-methylpyridin-3-amine was used instead of 6-methoxypyridin-3-amine $^1$H NMR (300 MHz, DMSO-d$_6$): δ 9.21 (s, 1H), 8.37 (s, 1H), 8.16 (d, J=9.0 Hz, 1H), 8.08-8.03 (m, 2H), 7.56 (s, 1H), 7.00 (d, J=7.8 Hz, 1H), 6.80 (s, 2H), 3.97 (s, 3H), 3.84 (s, 3H), 2.15 (s, 3H); MS (m/z): 505 (M+1)$^+$.

Example 10

N-(8-(6-amino-5-(trifluoromethyl)pyridin-3-yl)-1-(6-cyanopyridin-3-yl)-3-methyl-1H-imidazo[4,5-c]quinolin-2(3H)-ylidene)cyanamide The title compound was prepared by following the procedure as described for Example 1, except that 5-aminopicolinonitrile was used instead of 6-methoxypyridin-3-amine. $^1$H NMR (300 MHz, DMSO-d$_6$): δ 9.31 (d, J=2.1 Hz, 1H), 9.24 (s, 1H), 8.68-8.67 (m, 1H), 8.50 (d, J=8.1 Hz, 1H), 8.38 (s, 1H), 8.20 (d, J=9.0 Hz, 1H), 8.08-8.07 (m, 1H), 7.52 (s, 1H), 6.86 (d, J=1.5 Hz, 1H), 6.81 (s, 2H), 3.91 (s, 3H); MS (m/z): 486 (M+1)$^+$.

Example 11

N-(8-(6-amino-5-(trifluoromethyl)pyridin-3-yl)-3-methyl-1-(quinolin-6-yl)-1H-imidazo[4,5-c]quinolin-2(3H)-ylidene)cyanamide The title compound was prepared by following the procedure as described for Example 1, except that quinolin-6-amine was used instead of 6-methoxypyridin-3-amine $^1$H NMR (300 MHz, DMSO-d$_6$): δ 9.28 (brs, 1H), 9.05 (brs, 1H), 8.50-7.85 (m, 6H), 7.58 (s, 1H), 7.23 (s, 1H), 6.75 (s, 2H), 6.43 (s, 1H), 3.92 (s, 3H); MS (m/z): 511(M+1)$^+$.

Example 12

N-(1-(4-(2-cyanopropan-2-yl)phenyl)-3-methyl-8-(6-(methylamino)-5-(trifluoromethyl)pyridin-3-yl)-1H-imidazo[4,5-c]quinolin-2(3H)-ylidene)cyanamide To the stirred solution of Example 6 (0.014 mmol) in dry THF was added potassium-t-butoxide (0.157 mmol) at 0° C. Reaction mixture was stirred further for 15 minutes, followed by addition of methyl iodide (0.125 mmol). Reaction mixture was warmed to RT and stirred overnight. Solvent was removed and diluted with EtOAc. Organic layer was washed with water, dried over anhydrous Na$_2$SO$_4$ and solvent was removed. Crude product was further purified (silica gel column, MeOH/CHCl$_3$ as eluent) to obtain the title compound. $^1$H NMR (300 MHz, DMSO-d$_6$): δ 9.19 (s, 1H), 8.16-8.11 (m, 2H), 8.00-7.91 (m, 1H), 7.89 (s, 3H), 7.76 (brs, 1H), 6.87 (d, J=1.8 Hz, 1H), 6.79 (q, J=4.5 Hz, 1H), 3.92 (s, 3H), 2.89 (d, J=4.2 Hz, 3H), 1.82 (s, 6H); MS (m/z): 541(M+1)$^+$.

Example 13

N-(8-(5-amino-6-methoxypyridin-3-yl)-1-(2,4-dimethoxyphenyl)-3-methyl-1H-imidazo[4,5-c]quinolin-2(3H)-ylidene)cyanamide Step 1: 6-bromo-N-(2,4-dimethoxyphenyl)-3-nitroquinolin-4-amine The title compound was prepared by following the procedure as described in step 2 for Example 1, except that 2,4-dimethoxyaniline was used instead of 6-methoxypyridin-3-amine Step 2: 6-bromo-N-(2,4-dimethoxyphenyl)quinoline-3,4-diamine 6-bromo-N-(2,4-dimethoxyphenyl)-3-nitroquinolin-4-amine (17.32 mmol) was suspended in 50 mL ethyl acetate.

Stannous chloride (69.3 mmol) was added to it. Reaction mixture stirred at RT for 1 h. Completion of reaction was monitored by TLC. Reaction mixture was diluted with ethyl acetate and reaction mixture was quenched using chilled 10 M NaOH solution (70 mL). Reaction mixture was extracted with ethyl acetate several times. Organic layer were dried over anhydrous $Na_2SO_4$ and evaporated under vacuum. Crude product was further purified on silica gel column using MeOH/CHCl$_3$ (3%) as elute to afford desired product. $^1$H NMR (300 MHz, DMSO-d$_6$): δ 8.58 (s, 1H), 7.75-7.70 (m, 2H), 7.43 (d, J=6 Hz, 1H), 6.73 (s, 1H), 6.64 (d, J=3 Hz, 1H), 6.25-6.23 (m, 1H), 5.89 (d, J=3 Hz, 1H), 5.40 (s, 1H), 3.91 (s, 3H), 3.66 (s, 3H); MS (m/z): 375 (M+1)$^+$.

Step 3: N-(8-bromo-1-(2,4-dimethoxyphenyl)-1H-imidazo[4,5-c]quinolin-2(3H)-ylidene)cyanamide To the stirred solution of 6-bromo-N4-(2,4-dimethoxyphenyl)quinoline-3,4-diamine (10.69 mmol) in DMF (10 mL) was added dimethylcyanocarbonimidodithioate (16.03 mmol) followed by cesium carbonate (32.1 mmol) and the resulting reaction mixture was heated at 80° C. for 18 h. Completion of reaction was monitored by TLC, solvent evaporated under reduced pressure. Residue was diluted with water & extracted with ethyl acetate (250 mlx 5), organic layer were dried over anhydrous $Na_2SO_4$ and evaporated under vacuum. Crude product was further purified on silica gel column using MeOH/CHCl$_3$ (8%) as elute to afford desired product as off-white solid. $^1$H NMR (300 MHz, DMSO-d$_6$): δ 13.72 (s, 1H), 8.93 (s, 1H), 8.03 (d, J=9 Hz, 1H), 7.77 (dd, J=3.9 Hz, 1H), 7.58 (d, J=9 Hz, 1H), 7.16 (d, J=3 Hz, 1H), 6.93 (d, J=3 Hz, 1H), 6.84 (dd, J=3, 9 Hz, 1H), 3.92 (s, 3H), 3.69 (s, 3H); MS (m/z): 424 (M+1)$^+$.

Step 4: N-(8-bromo-1-(2,4-dimethoxyphenyl)-3-methyl-1H-imidazo[4,5-c]quinolin-2(3H)-ylidene)cyanamide The title compound was prepared by following the procedure as described in step 5 for Example 1, except that N-(8-bromo-1-(2,4-dimethoxyphenyl)-1H-imidazo[4,5-c]quinolin-2(3H)-ylidene)cyanamide was used instead of N-(8-bromo-1-(6-methoxypyridin-3-yl)-1H-imidazo[4,5-c]quinolin-2(3H)-ylidene)cyanamide.

Step 5: N-(8-(5-amino-6-methoxypyridin-3-yl)-1-(2,4-dimethoxyphenyl)-3-methyl-1H-imidazo[4,5-c]quinolin-2(3H)-ylidene)cyanamide The title compound was prepared by following the procedure as described in step 6 for Example 1, except that 5-amino-6-methoxypyridin-3-ylboronic acid was used instead of 6-amino-5-(trifluoromethyl)pyridin-3-ylboronic acid. $^1$H NMR (300 MHz, DMSO-d$_6$): δ 9.15 (s, 1H), 8.14 (d, J=9 Hz, 1H), 7.84 (dd, J=3 Hz, J=9 Hz, 1H), 7.68 (d, J=9 Hz, 1H), 7.39 (d, J=3 Hz, 1H), 7.04 (d, J=3 Hz, 1H), 6.97 (d, J=3 Hz, 1H), 6.87 (m, 2H), 5.11 (s, 2H), 3.95 (m, 6H), 3.80 (m, 6H); MS (m/z): 482 (M+1)$^+$.

Preparation of 5-amino-6-methoxypyridin-3-ylboronic acid 5-bromo-2-methoxypyridin-3-amine (2 g, 9.85 mmol, commercially available), Bis(pinacolato)diboron (11.82 mmol), potassium acetate (1.4 g) and (1,1-bis(diphenylphosphino)ferrocene)-dichloropalladium (II) complex with DCM (200 mg, commercially available) was dissolved in dioxane (75 mL) under argon atmosphere. The reaction mixture was refluxed for 8 h. The reaction mixture was cooled, diluted with ethyl acetate (75 mL) and filtered. The filtrate was concentrated. The crude product was purified over silica gel using 0-10% ethyl acetate in petroleum ether to obtain the titled boronic acid derivative.

The compounds of Examples 14-121 were prepared by following the procedure as described for Example 13, using an appropriate amine, and an appropriate boronic acid derivative. The amine and boronic acid derivatives were commercially available except indicated otherwise.

Example 14

N-(1-(6-methoxypyridin-3-yl)-3-methyl-8-(pyridin-4-yl)-1H-imidazo[4,5-c]quinolin-2(3H)-ylidene)cyanamide $^1$H NMR (300 MHz, DMSO-d$_6$): δ 9.28 (s, 1H), 8.69 (d, J=2.4 Hz, 1H), 8.61 (d, J=6 Hz, 1H), 8.26 (s, 1H), 8.19 (m, 1H), 8.06 (dd, J=2.1, 9 Hz, 1H), 7.35 (d, J=6 Hz, 2H), 7.23 (s, 1H), 7.18 (m, 1H), 4.04 (s, 3H), 3.85 (s, 3H); MS (m/z): 408 (M+1)$^+$.

Example 15

N-(8-(2-fluoro-5-(trifluoromethyl)phenyl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.29 (s, 1H), 8.63 (s, 1H), 8.22 (d, J=9 Hz, 1H), 8.15 (d, J=6.3 Hz, 1H), 7.94 (d, J=8.7 Hz, 1H), 7.83 (s, 1H), 7.53 (m, 2H), 7.09 (m, 2H), 3.95 (s, 3H), 3.86 (s, 3H); MS (m/z): 493 (M+1)$^+$.

Example 16

N-(8-(3,5-difluorophenyl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.25 (s, 1H), 8.70 (d, J=2.7 Hz, 1H), 8.19 (d, J=8.7 Hz, 2H), 8.07 (d, J=1.5 Hz, 1H), 7.19 (m, 2H), 7.06 (m, 3H), 4.02 (s, 3H), 3.85 (s, 3H); MS (m/z): 443 (M+1)$^+$.

Example 17

N-(8-(Benzo[d][1,3]dioxol-5-yl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.19 (s, 1H), 8.68 (s, 1H), 8.12 (m, 2H), 7.92 (d, J=9 Hz, 1H), 7.18 (d, J=8.7 Hz, 1H), 6.96 (d, J=7.5 Hz, 2H), 6.87 (d, J=9 Hz, 2H), 6.08 (s, 2H), 4.03 (s, 3H), 3.84 (s, 3H); MS (m/z): 451 (M+1)$^+$.

Example 18

N-(1-(6-methoxypyridin-3-yl)-3-methyl-8-(3,4,5-trimethoxyphenyl)-1H-imidazo[4,5-c]quinolin-2(3H)-ylidene)cyanamide $^1$H NMR (300 MHz, DMSO-d$_6$): δ 9.21 (s, 2H), 8.66 (d, J=2.4 Hz, 2H), 8.31 (s, 1H), 8.23 (d, J=2.7 Hz, 1H), 8.20 (d, J=2.7 Hz, 2H), 8.17 (s, 1H), 3.97 (s, 3H), 3.85 (s, 3H), 3.80 (s, 6H), 3.68 (s, 3H); MS (m/z): 497 (M+1)+.

Example 19

N-(1-(6-methoxypyridin-3-yl)-3-methyl-8-(naphthalen-2-yl)-1H-imidazo[4,5-c]quinolin-2(3H)-ylidene)cyanamide $^1$H NMR (300 MHz, DMSO-d$_6$): δ 9.24 (s, 1H), 8.71 (s, 1H), 8.15 (m, 3H), 7.89 (m, 4H), 7.51 (m, 3H), 7.25 (d, J=9 Hz, 2H), 4.03 (s, 3H), 3.86 (s, 3H); MS (m/z): 457 (M+1)+.

Example 20

N-(1-(6-methoxypyridin-3-yl)-8-(2-methoxypyrimidin-5-yl)-3-methyl-1H-imidazo[4,5-c]quinolin-2(3H)-ylidene)cyanamide $^1$H NMR (300 MHz, DMSO-d$_6$): δ 9.25 (s, 1H), 8.66 (d, J=2.4 Hz, 1H), 8.62 (s, 2H), 8.18 (m, 2H), 8.02 (m, 1H), 7.19 (d, J=8.7 Hz, 1H), 7.06 (s, 1H), 4.01 (s, 6H), 3.96 (s, 3H); MS (m/z): 439 (M+1)+.

Example 21

N-(8-(2,4-dimethoxypyrimidin-5-yl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.23 (s, 1H), 8.62 (d, J=2.7 Hz, 1H), 8.35 (s, 1H), 8.12 (m, 2H), 7.83 (dd, J=1.8, 8.7 Hz, 1H), 7.30 (d, J=1.5 Hz, 1H), 7.15 (d, J=8.7 Hz, 1H), 3.93 (m, 6H), 3.82 (m, 6H); MS (m/z): 469 (M+1)+.

Example 22

N-(8-(2-fluoropyridin-3-yl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.25 (s, 1H), 8.62 (d, J=2.4 Hz, 1H), 8.22 (m, 2H), 8.14 (dd, J=2.7, 9 Hz, 1H), 7.99 (m, 1H), 7.92 (m, 1H), 7.45 (m, 1H), 7.23 (s, 1H), 7.13 (d, J=8.7 Hz, 1H), 3.98 (s, 3H), 3.85 (s, 3H); MS (m/z): 426 (M+1)+.

Example 23

N-(8-(2,6-difluoropyridin-3-yl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.28 (s, 1H), 8.61 (d, J=2.4 Hz, 1H), 8.22 (m, 2H), 8.13 (dd, J=2.7, 9 Hz, 1H), 7.93 (s, 1H), 7.30 (dd, J=2.7, 8.4 Hz, 1H), 7.22 (s, 1H), 7.13 (d, J=7.8 Hz, 1H), 3.99 (s, 3H), 3.85 (s, 3H); MS (m/z): 444 (M+1)+.

Example 24

N-(1-(6-methoxypyridin-3-yl)-3-methyl-8-phenyl-1H-imidazo[4,5-c]quinolin-2(3H)-ylidene)cyanamide $^1$H NMR (300 MHz, DMSO-d$_6$): δ 9.22 (s, 1H), 8.68 (d, J=2.4 Hz, 1H), 8.18 (m, 2H), 7.97 (dd, J=1.8, 9 Hz, 1H), 7.37 (m, 5H), 7.18 (d, J=9 Hz, 1H), 7.08 (s, 1H), 4.02 (s, 3H), 3.84 (s, 3H); MS (m/z): 407 (M+1)+.

Example 25

N-(1-(6-methoxypyridin-3-yl)-3-methyl-8-(5-(trifluoromethyl)pyridin-3-yl)-1H-imidazo[4,5-c]quinolin-2(3H)-ylidene)cyanamide $^1$H NMR (300 MHz, DMSO-d$_6$): δ 9.29 (s, 1H), 9.00 (s, 2H), 8.67 (d, J=2.4 Hz, 1H), 8.22 (d, J=8.7 Hz, 1H), 8.18 (m, 2H), 8.01 (s, 1H), 7.15 (m, 2H), 3.98 (s, 3H), 3.85 (s, 3H); MS (m/z): 476 (M+1)+.

Example 26

N-(1-(6-methoxypyridin-3-yl)-3-methyl-8-(quinolin-7-yl)-1H-imidazo[4,5-c]quinolin-2(3H)-ylidene)cyanamide $^1$H NMR (300 MHz, DMSO-d$_6$): δ 9.25 (s, 1H), 8.93 (d, J=2.7 Hz, 1H), 8.71 (d, J=2.4 Hz, 1H), 8.30 (m, 1H), 8.23 (m, 2H), 8.15 (d, J=8.7 Hz, 1H), 7.99 (m, 2H), 7.72 (d, J=8.7 Hz, 1H), 7.60 (dd, J=4.2, 8.4 Hz, 1H), 7.22 (m, 2H), 4.02 (s, 3H), 3.86 (s, 3H); MS (m/z): 458 (M+1)+.

Example 27

N-(8-(2-isopropoxyphenyl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.21 (s, 1H), 8.62 (d, J=2.4 Hz, 1H), 8.10 (m, 2H), 7.82 (dd, J=1.8, 9 Hz, 1H), 7.28 (m, 1H), 7.04 (m, 3H), 6.98 (m, 2H), 4.49 (m, 1H), 3.95 (s, 3H), 3.85 (s, 3H); MS (m/z): 465 (M+1)+.

Example 28

N-(8-(3-chlorophenyl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.24 (s, 1H), 8.69 (d, J=2.4 Hz, 1H), 8.19 (m, 2H), 8.04 (d, J=2.1 Hz, 1H), 7.45 (m, 3H), 7.30 (s, 1H), 7.18 (d, J=8.7 Hz, 1H), 7.09 (d, J=1.8 Hz, 1H), 4.03 (s, 3H), 3.85 (s, 3H); MS (m/z): 441 (M+1)+.

Example 29

N-(1-(6-methoxypyridin-3-yl)-3-methyl-8-m-tolyl-1H-imidazo[4,5-c]quinolin-2(3H)-ylidene)cyanamide $^1$H NMR (300 MHz, DMSO-d$_6$): δ 9.21 (s, 1H), 8.68 (d, J=2.4 Hz, 1H), 8.16 (m, 2H), 7.98 (dd, J=1.8, 8.7 Hz, 1H), 7.28 (m, 2H), 7.19 (m, 2H), 7.08 (m, 2H), 4.02 (s, 3H), 3.84 (s, 3H), 2.33 (s, 3H); MS (m/z): 421 (M+1)+.

Example 30

N-(8-(4-cyanophenyl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.26 (s, 1H), 8.68 (d, J=2.4 Hz, 1H), 8.18 (m, 2H), 8.01 (m, 1H), 7.91 (d, J=8.1 Hz, 2H), 7.54 (d, J=8.1 Hz, 2H), 7.14 (m, 2H), 4.03 (s, 3H), 3.85 (s, 3H); MS (m/z): 432 (M+1)⁺.

Example 31

N-(1-(6-methoxypyridin-3-yl)-3-methyl-8-(4-phenoxyphenyl)-1H-imidazo[4,5-c]quinolin-2(3H)-ylidene)cyanamide ¹H NMR (300 MHz, DMSO-d₆): δ 9.21 (s, 1H), 8.67 (d, J=2.4 Hz, 1H), 8.16 (m, 2H), 7.88 (m, 1H), 7.37 (m, 4H), 7.19 (m, 2H), 7.10 (s, 1H), 7.07 (s, 1H), 7.02 (m, 3H), 3.98 (s, 3H), 3.85 (s, 3H). MS (m/z): 499 (M+1)⁺.

Example 32

N-(8-(2-chlorophenyl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.27 (s, 1H), 8.60 (d, J=2.4 Hz, 1H), 8.19 (d, J=8.7 Hz, 1H), 8.13 (dd, J=2.4, 8.7 Hz, 1H), 7.77 (d, J=1.8 Hz, 1H), 7.08 (m, 2H), 7.10 (s, 1H), 7.07 (s, 1H), 7.02 (m, 2H), 3.94 (s, 3H), 3.34 (s, 3H); MS (m/z): 441(M+1)⁺.

Example 33

N-(8-(3-methoxyphenyl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.22 (s, 1H), 8.68 (d, J=2.7 Hz, 1H), 8.17 (m, 2H), 7.99 (dd, J=1.8, 9 Hz, 1H), 7.15 (m, 3H), 7.02 (d, J=7.8 Hz, 1H), 6.94 (dd, J=2.1, 8.1 Hz, 1H), 7.07 (s, 1H), 7.02 (m, 3H), 4.02 (s, 3H), 3.85 (s, 3H), 3.78 (s, 3H); MS (m/z): 437 (M+1)⁺.

Example 34

N-(1-(6-methoxypyridin-3-yl)-3-methyl-8-o-tolyl-1H-imidazo[4,5-c]quinolin-2(3H)-ylidene)cyanamide ¹H NMR (300 MHz, DMSO-d₆): δ 9.18 (s, 1H), 8.65 (d, J=2.4 Hz, 1H), 8.13 (m, 2H), 7.95 (d, J=1.8 Hz, 1H), 7.19 (m, 4H), 7.03 (m, 2H), 4.01 (s, 3H), 3.81 (s, 3H), 2.31 (s, 3H); MS (m/z): 421 (M+1)⁺.

Example 35

N-(8-(isoquinolin-4-yl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.26 (s, 1H), 9.10 (d, J=2.1 Hz, 1H), 8.89 (m, 1H), 8.44 (dd, J=2.4, 8.4 Hz, 1H), 8.36 (d, J=7.8 Hz, 1H), 8.24 (d, J=9 Hz, 1H), 8.13 (dd, J=1.5, 8.7 Hz, 1H), 7.97 (m, 3H), 7.51 (m, 2H), 7.07 (d, J=1.5 Hz, 1H), 4.02 (s, 3H), 3.85 (s, 3H); MS (m/z): 458 (M+1)⁺.

Example 36

N-(8-(3,4-dimethoxyphenyl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.19 (s, 1H), 8.66 (d, J=2.7 Hz, 1H), 8.20 (dd, J=2.7, 8.7 Hz, 1H), 8.15 (d, J=8.7 Hz, 1H), 7.98 (dd, J=1.8, 9 Hz, 1H), 7.19 (d, J=8.7 Hz, 1H), 7.15 (d, J=1.5 Hz, 1H), 6.99 (m, 2H), 6.77 (d, J=1.8 Hz, 1H), 3.99 (s, 3H), 3.85 (s, 3H), 3.79 (s, 3H), 3.76 (s, 3H); MS (m/z): 467 (M+1)⁺.

Example 37

N-(8-(4-(isopropylthio)phenyl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.22 (s, 1H), 8.67 (d, J=2.4 Hz, 1H), 8.18 (dd, J=2.7, 8.7 Hz, 1H), 8.17 (s, 1H), 7.99 (d, J=2.1 Hz, 1H), 7.31 (m, 4H), 7.19 (d, J=9 Hz, 1H), 7.04 (d, J=1.8 Hz, 1H), 4.03 (s, 3H), 1.26 (s, 6H); MS (m/z): 481 (M+1)⁺.

Example 38

N-(8-(3-hydroxyphenyl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.61 (s, 1H), 9.21 (s, 1H), 8.67 (d, J=2.7 Hz, 1H), 8.17 (dd, J=2.7 Hz, 1H), 8.16 (s, 1H), 7.89 (dd, J=1.8, 9 Hz, 1H), 7.17 (m, 2H), 7.06 (d, J=1.8 Hz, 1H), 6.75 (m, 3H), 4.03 (s, 3H), 3.85 (s, 3H); MS (m/z): 423 (M+1)⁺.

Example 39

N-(8-(4-fluoropyridin-3-yl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.26 (s, 1H), 8.67 (d, J=2.4 Hz, 1H), 8.18 (m, 3H), 8.01 (m, 2H), 7.32 (d, J=2.7 Hz, 1H), 7.17 (d, J=8.7 Hz, 1H), 7.07 (d, J=1.8 Hz, 1H), 4.02 (s, 3H), 3.85 (s, 3H), 1.34 (s, 6H); MS (m/z): 426 (M+1)⁺.

Example 40

N-(8-(3-fluorophenyl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.21 (s, 1H), 8.67 (d, J=2.4 Hz, 1H), 8.16 (m, 2H), 7.98 (dd, J=1.5, 8.7 Hz, 1H), 7.42 (m, 1H), 7.16 (m, 3H), 7.10 (d, J=10.5 Hz, 1H), 7.05 (s, 1H), 4.00 (s, 3H), 3.82 (s, 3H); MS (m/z): 425 (M+1)⁺.

Example 41

N-(1-(6-methoxypyridin-3-yl)-3-methyl-8-(3-(trifluoromethyl)phenyl)-1H-imidazo[4,5-c]quinolin-2(3H)-ylidene)cyanamide ¹H NMR (300 MHz, DMSO-d₆): δ 9.23 (s, 1H), 8.64 (d, J=2.4 Hz, 1H), 8.16 (m, 2H), 8.08 (s, 1H), 7.81 (s, 1H), 7.67 (m, 2H), 7.47 (s, 1H), 7.13 (s, 2H), 3.96 (s, 3H), 3.82 (s, 3H); MS (m/z): 475 (M+1)⁺.

Example 42

N-(8-(2,6-dimethylphenyl)-1-(6-methoxypyridin-3-yl)-3-methyl-1H-imidazo[4,5-c]quinolin-2(3H)-ylidene)cyanamide ¹H NMR (300 MHz, DMSO-d₆): δ 9.23 (s, 1H), 8.53 (d, J=2.4 Hz, 1H), 8.14 (d, J=8.7 Hz, 1H), 8.08 (dd, J=2.7, 9 Hz 1H), 7.43 (d, J=1.5, 8.7 Hz, 1H), 7.01 (m, 4H), 6.66 (s, 1H), 3.83 (m, 6H), 1.84 (m, 6H); MS (m/z): 435 (M+1)$^+$.

Example 43

N-(1-(6-methoxypyridin-3-yl)-3-methyl-8-(4-(trifluoromethyl)phenyl)-1H-imidazo[4,5-c]quinolin-2(3H)-ylidene)cyanamide $^1$H NMR (300 MHz, DMSO-d$_6$): δ 9.24 (s, 1H), 8.65 (d, J=2.4 Hz, 1H), 8.17 (m, 2H), 8.02 (d, J=1.8 Hz, 1H), 7.76 (d, J=8.4 Hz, 2H), 7.55 (d, J=8.1 Hz, 2H), 7.11 (m, 2H), 3.99 (s, 3H), 3.83 (s, 3H); MS (m/z): 421 (M+1)$^+$.

Example 44

N-(1-(6-methoxypyridin-3-yl)-3-methyl-8-p-tolyl-1H-imidazo[4,5-c]quinolin-2(3H)-ylidene)cyanamide $^1$H NMR (300 MHz, DMSO-d$_6$): δ 9.18 (s, 1H), 8.65 (d, J=2.4 Hz, 1H), 8.13 (m, 2H), 7.95 (d, J=1.8 Hz, 1H), 7.19 (m, 4H), 7.03 (m, 2H), 4.01 (s, 3H), 3.81 (s, 3H), 2.31 (s, 3H); MS (m/z): 421 (M+1)$^+$.

Example 45

N-(1-(6-methoxypyridin-3-yl)-3-methyl-8-(2-methylpyridin-3-yl)-1H-imidazo[4,5-c]quinolin-2(3H)-ylidene)cyanamide $^1$H NMR (300 MHz, DMSO-d$_6$): δ 9.24 (s, 1H), 8.59 (d, J=2.4 Hz, 1H), 8.43 (d, J=3.6 Hz, 1H), 8.12 (m, 2H), 7.70 (d, J=7.2 Hz, 1H), 7.48 (d, J=6.9 Hz, 1H), 7.25 (m, 1H), 7.07 (m, 1H), 6.90 (s, 1H), 3.99 (s, 3H), 3.91 (s, 3H), 2.22 (s, 3H); MS (m/z): 422 (M+1)$^+$.

Example 46

N-(8-(4-hydroxyphenyl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.72 (s, 1H), 9.14 (s, 1H), 8.64 (d, J=2.4 Hz, 1H), 8.15 (dd, J=2.7, 8.7 Hz, 1H), 8.08 (d, J=8.7 Hz, 1H), 7.87 (dd, J=1.8, 9 Hz, 1H), 7.15 (m, 3H), 6.94 (s, 1H), 6.75 (s, 2H), 4.01 (s, 3H), 3.80 (s, 3H); MS (m/z): 423 (M+1)$^+$.

Example 47

N-(8-(5-fluoro-2-methoxyphenyl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.20 (s, 1H), 8.59 (d, J=2.4 Hz, 1H), 8.10 (d, J=8.7 Hz, 2H), 7.77 (dd, J=1.8, 8.7 Hz, 1H), 7.23 (d, J=1.8 Hz, 1H), 7.00 (m, 4H), 3.94 (s, 3H), 3.82 (s, 3H), 3.62 (s, 3H); MS (m/z): 455 (M+1)$^+$.

Example 48

N-(1,8-bis(6-methoxypyridin-3-yl)-3-methyl-1H-imidazo[4,5-c]quinolin-2(3H)-ylidene)cyanamide $^1$H NMR (300 MHz, DMSO-d$_6$): δ 9.19 (s, 1H), 8.65 (d, J=2.4 Hz, 1H), 8.15 (m, 3H), 7.97 (d, J=1.8 Hz, 1H), 7.64 (dd, J=2.4, 8.7 Hz, 1H), 7.16 (d, J=8.7 Hz, 1H), 6.99 (s, 1H), 6.85 (s, 1H), 4.00 (s, 3H), 3.87 (s, 3H), 3.82 (s, 3H); MS (m/z): 438 (M+1)$^+$.

Example 49

N-(8-(2-methoxyphenyl)-1-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.18 (s, 1H), 8.59 (d, J=2.4 Hz 1H), 8.10 (m, 2H), 7.78 (d, J=1.8 Hz, 1H), 7.10 (m, 3H), 6.98 (m, 3H), 3.93 (s, 3H), 3.82 (s, 3H), 3.63 (s, 3H); MS (m/z): 437 (M+1)$^+$.

Example 50

N-(1-(6-(2-cyanopropan-2-yl)pyridin-3-yl)-8-(4-hydroxyphenyl)-3-methyl-1H-imidazo[4,5-c]quinolin-2(3H)-ylidene)cyanamide $^1$H NMR (300 MHz, DMSO-d$_6$): δ 9.72 (s, 1H), 9.17 (s, 1H), 9.06 (d, J=2.1 Hz, 1H), 8.39 (dd, J=2.4, 8.4 Hz, 1H), 8.00 (m, 2H), 7.90 (m, 1H), 7.10 (d, J=8.4 Hz, 2H), 6.74 (m, 3H), 3.89 (s, 3H), 1.82 (s, 6H); MS (m/z): 460 (M+1)$^+$.

Example 51

N-(1-(6-(2-cyanopropan-2-yl)pyridin-3-yl)-8-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.22 (s, 1H), 9.06 (d, J=2.4 Hz, 1H), 8.39 (dd, J=2.4, 8.4 Hz, 1H), 8.16 (d, J=9 Hz, 1H), 8.08 (d, J=2.4 Hz, 1H), 7.96 (m, 2H), 7.61 (dd, J=2.4, 8.7 Hz, 1H), 6.79 (m, 2H), 3.90 (s, 3H), 3.84 (s, 3H), 1.82 (s, 6H); MS (m/z): 475 (M+1)$^+$.

Example 52

N-(1-(6-(2-cyanopropan-2-yl)pyridin-3-yl)-8-(5-fluoro-2-methoxyphenyl)-3-methyl-1H-imidazo[4,5-c]quinolin-2(3H)-ylidene)cyanamide $^1$H NMR (300 MHz, DMSO-d$_6$): δ 9.23 (s, 1H), 9.01 (s, 1H), 8.34 (dd, J=3.9, 8.4 Hz, 1H), 8.11 (d, J=9 Hz, 1H), 7.94 (d, J=8.4 Hz, 1H), 7.78 (d, J=8.7 Hz, 1H), 7.77 (m, 1H), 7.02 (m, 1H), 6.95 (s, 2H), 3.89 (s, 3H), 3.63 (s, 3H), 1.71 (s, 6H); MS (m/z): 492 (M+1)$^+$.

Example 53

N-(1-(6-(2-cyanopropan-2-yl)pyridin-3-yl)-8-(2-methoxyphenyl)-3-methyl-1H-imidazo[4,5-c]quinolin-2(3H)-ylidene)cyanamide $^1$H NMR (300 MHz, DMSO-d$_6$): δ 9.21 (s, 1H), 9.01 (d, J=2.4 Hz, 1H), 8.35 (dd, J=2.4, 8.4 Hz, 1H), 8.10 (d, J=8.7 Hz, 1H), 7.93 (d, J=8.4 Hz, 1H), 7.77 (dd, J=1.8, 9 Hz, 1H), 7.28 (m, 2H), 7.02 (m, 2H), 6.93 (m, 1H), 3.89 (s, 3H), 3.66 (s, 3H), 1.71 (s, 6H); MS (m/z): 474 (M+1)$^+$.

Example 54

N-(8-(benzo[d][1,3]dioxol-5-yl)-1-(6-(2-cyanopropan-2-yl)pyridin-3-yl)-3-methyl-1H-imidazo[4,5-c]quinolin-2(3H)-ylidene)cyanamide $^1$H NMR (300 MHz, DMSO-d$_6$): δ 9.20 (s, 1H), 9.07 (s, 1H), 8.39 (dd, J=2.4, 8.4 Hz, 1H), 8.12 (d, J=9 Hz, 1H), 8.00

(d, J=8.4 Hz, 1H), 7.90 (dd, J=2.1, 9 Hz, 1H), 6.89 (d, J=8.1 Hz, 1H), 6.80 (m, 3H), 6.03 (s, 2H), 3.90 (m, 1H), 1.81 (s, 6H); MS (m/z): 488 (M+1)+.

Example 55

N-(1-(6-(2-cyanopropan-2-yl)pyridin-3-yl)-8-(2,4-dimethoxy pyrimidin-5-yl)-3-methyl-1H-imidazo[4,5-c]quinolin-2(3H)-ylidene)cyanamide $^1$H NMR (300 MHz, DMSO-$d_6$): δ 9.24 (s, 1H), 9.02 (d, J=2.1 Hz, 1H), 8.35 (dd, J=2.4, 8.4 Hz, 1H), 8.14 (d, J=6.9 Hz, 2H), 7.96 (d, J=8.4 Hz, 1H), 7.82 (dd, J=1.8, 9 Hz, 1H), 6.93 (d, J=1.5 Hz, 1H), 3.89 (s, 6H), 3.84 (s, 3H), 1.75 (s, 6H); MS (m/z): 506 (M+1)+.

Example 56

N-(1-(6-(2-cyanopropan-2-yl)pyridin-3-yl)-3-methyl-8-(quinolin-6-yl)-1H-imidazo[4,5-c]quinolin-2(3H)-ylidene)cyanamide $^1$H NMR (300 MHz, DMSO-$d_6$): δ 9.26 (s, 1H), 9.10 (d, J=2.1 Hz, 1H), 8.89 (m, 1H), 8.44 (dd, J=2.4, 8.4 Hz, 1H), 8.36 (d, J=7.8 Hz, 1H), 8.24 (d, J=9 Hz, 1H), 8.13 (dd, J=1.5, 8.7 Hz, 1H), 7.97 (m, 3H), 7.51 (m, 2H), 7.07 (d, J=1.5 Hz, 1H), 3.93 (s, 1H), 1.77 (s, 6H); MS (m/z): 495 (M+1)+.

Example 57

N-(1-(6-(2-cyanopropan-2-yl)pyridin-3-yl)-3-methyl-8-(3,4,5-trimethoxyphenyl)-1H-imidazo[4,5-c]quinolin-2(3H)-ylidene)cyanamide $^1$H NMR (300 MHz, DMSO-$d_6$): δ 9.23 (s, 1H), 9.07 (d, J=1.8 Hz, 1H), 8.40 (dd, J=2.1, 8.1 Hz, 1H), 8.16 (d, J=8.7 Hz, 1H), 7.95 (m, 2H), 6.98 (s, 1H), 6.59 (s, 2H), 3.90 (s, 3H), 3.79 (s, 6H), 3.64 (s, 3H), 1.71 (s, 6H); MS (m/z): 534 (M+1)+.

Example 58

N-(8-(benzo[d][1,3]dioxol-5-yl)-1-(6-methoxy-2-methylpyridin-3-yl)-3-methyl-1H-imidazo[4,5-c]quinolin-2(3H)-ylidene)cyanamide $^1$H NMR (300 MHz, DMSO-$d_6$): δ 9.19 (s, 1H), 8.11 (d, J=9 Hz, 1H), 8.02 (d, J=8.7 Hz, 1H), 7.94 (d, J=1.8 Hz, 1H), 6.86 (m, 4H), 6.84 (s, 1H), 6.06 (d, J=3 Hz, 2H), 4.00 (s, 3H), 3.82 (s, 3H), 2.25 (s, 3H); MS (m/z): 465 (M+1)+.

Example 59

N-(1-(6-methoxy-2-methylpyridin-3-yl)-3-methyl-8-(3,4,5-trimethoxyphenyl)-1H-imidazo[4,5-c]quinolin-2(3H)-ylidene)cyanamide $^1$H NMR (300 MHz, DMSO-$d_6$): δ 9.21 (s, 1H), 8.16 (d, J=9 Hz, 1H), 7.99 (m, 2H), 7.15 (d, J=1.5 Hz, 1H), 6.98 (d, J=8.7 Hz, 1H), 6.63 (s, 2H), 3.93 (s, 3H), 3.83 (s, 3H), 3.79 (s, 6H), 3.75 (s, 3H), 2.26 (s, 3H); MS (m/z): 511 (M+1)+.

Example 60

N-(1-(6-(2-cyanopropan-2-yl)pyridin-3-yl)-3-methyl-8-(1H-pyrrolo[2,3-b]pyridin-5-yl)-1H-imidazo[4,5-c]quinolin-2(3H)-ylidene)cyanamide $^1$H NMR (300 MHz, DMSO-$d_6$): δ 11.85 (s, 1H), 9.24 (s, 1H), 9.11 (s, 1H), 8.45 (d, J=4.8 Hz, 1H), 8.21 (d, J=5.4 Hz, 1H), 8.16 (s, 1H), 8.04 (m, 2H), 7.90 (s, 1H), 7.53 (s, 1H), 3.93 (s, 3H), 1.81 (s, 6H); MS (m/z): 484 (M+1)+.

Example 61

N-(8-(6-aminopyridin-3-yl)-1-(6-(2-cyanopropan-2-yl)pyridin-3-yl)-3-methyl-1H-imidazo[4,5-c]quinolin-2(3H)-ylidene)cyanamide $^1$H NMR (300 MHz, DMSO-$d_6$): δ 9.26 (s, 1H), 9.18 (s, 1H), 8.42 (dd, J=1.5, 5.1 Hz, 1H), 8.11 (d, J=5.4 Hz, 1H), 7.92 (m, 3H), 7.22 (m, 1H), 6.77 (s, 1H), 6.43 (d, J=5.4 Hz, 1H), 6.24 (s, 2H), 3.91 (s, 3H), 1.86 (s, 6H); MS (m/z): 460 (M+1)+.

Example 62

N-(1-(6-(2-cyanopropan-2-yl)pyridin-3-yl)-3-methyl-8-(naphthalen-2-yl)-1H-imidazo[4,5-c]quinolin-2(3H)-ylidene)cyanamide $^1$H NMR (300 MHz, DMSO-$d_6$): δ 9.26 (s, 1H), 9.00 (d, J=1.5 Hz, 1H), 8.46 (dd, J=1.2, 4.8 Hz, 1H), 8.24 (d, J=5.4 Hz, 1H), 8.14 (d, J=5.1 Hz, 1H), 8.05 (d, J=4.8 Hz, 1H), 7.95 (s, 1H), 7.90 (m, 3H), 7.53 (m, 2H), 7.33 (d, J=5.1 Hz, 1H), 7.09 (s, 1H), 3.93 (s, 3H), 1.78 (s, 6H); MS (m/z): 494 (M+1)+.

Example 63

N-(1-(6-(2-cyanopropan-2-yl)pyridin-3-yl)-8-(3,5-difluorophenyl)-3-methyl-1H-imidazo[4,5-c]quinolin-2(3H)-ylidene)cyanamide $^1$H NMR (300 MHz, DMSO-$d_6$): δ 9.28 (s, 1H), 9.08 (s, 1H), 8.42 (dd, J=1.5, 5.1 Hz, 1H), 8.20 (d, J=5.1 Hz, 1H), 8.02 (d, J=5.1 Hz, 2H), 7.26 (m, 1H), 7.03 (s, 2H), 6.96 (s, 1H), 3.93 (s, 3H), 1.80 (s, 6H); MS (m/z): 480 (M+1)+.

Example 64

N-(1-(6-(2-cyanopropan-2-yl)pyridin-3-yl)-8-(2-fluoropyridin-3-yl)-3-methyl-1H-imidazo[4,5-c]quinolin-2(3H)-ylidene)cyanamide $^1$H NMR (300 MHz, DMSO-$d_6$): δ 9.30 (s, 1H), 9.04 (d, J=1.2 Hz, 1H), 8.37 (dd, J=1.5, 5.1 Hz, 1H), 8.23 (d, J=5.4 Hz, 2H), 7.93 (m, 3H), 7.41 (m, 1H), 7.01 (s, 1H), (s, 1H), 3.92 (s, 3H), 1.80 (s, 6H); MS (m/z): 463 (M+1)+.

Example 65

N-(1-(6-(2-cyanopropan-2-yl)pyridin-3-yl)-8-(2-isopropoxyphenyl)-3-methyl-1H-imidazo[4,5-c]quinolin-2(3H)-ylidene)cyanamide $^1$H NMR (300 MHz, DMSO-$d_6$): δ 9.23 (s, 1H), 9.03 (s, 1H), 8.36 (dd, J=1.5, 5.1 Hz, 1H), 8.01 (d, J=5.4 Hz, 1H), 7.93 (d, J=4.8 Hz, 1H), 7.85 (d, J=5.4 Hz, 1H), 7.27 (m, 1H), 7.04 (d, J=4.8 Hz, 1H), 6.91 (s, 2H), 6.77 (s, 1H), 4.44 (m, 1H), 3.92 (s, 3H), 1.71 (s, 6H), 1.11 (m, 6H); MS (m/z): 502 (M+1)+.

Example 66

N-(1-(6-(2-cyanopropan-2-yl)pyridin-3-yl)-8-(3,4-dimethoxyphenyl)-3-methyl-1H-imidazo[4,5-c]quinolin-2(3H)-ylidene)cyanamide $^1$H NMR (300 MHz, DMSO-$d_6$): 9.22 (s, 1H), 9.09 (d, J=2.1 Hz, 1H), 8.42 (dd, J=2.4, 8.4 Hz, 1H), 8.16 (d, J=8.7 Hz, 1H), 8.01 (m, 2H), 7.02 (d, J=2.1 Hz, 1H), 6.95 (s, 1H), 6.92 (m, 1H), 6.74 (d, J=2.1 Hz, 1H), 3.92 (s, 3H), 3.76 (m, 6H), 1.80 (s, 6H); MS (m/z): 504 (M+1)$^+$.

Example 67

N-(1-(6-(2-cyanopropan-2-yl)pyridin-3-yl)-3-methyl-8-p-tolyl-1H-imidazo[4,5-c]quinolin-2(3H)-ylidene)cyanamide $^1$H NMR (300 MHz, DMSO-d$_6$): δ 9.23 (s, 1H), 9.09 (d, J=2.1 Hz, 1H), 8.41 (d, J=2.4 Hz, 1H), 8.17 (d, J=9 Hz, 1H), 8.00 (m, 2H), 7.21 (s, 4H), 6.92 (d, J=1.5 Hz, 1H), 3.93 (s, 3H), 2.31 (s, 3H), 1.84 (s, 6H); MS (m/z): 458 (M+1)$^+$.

Example 68

N-(1-(6-(2-cyanopropan-2-yl)pyridin-3-yl)-3-methyl-8-(4-(trifluoromethyl)phenyl)-1H-imidazo[4,5-c]quinolin-2(3H)-ylidene)cyanamide $^1$H NMR (300 MHz, DMSO-d$_6$): δ 9.29 (s, 1H), 9.09 (d, J=2.1 Hz, 1H), 8.42 (dd, J=2.4, 10.8 Hz, 1H), 8.24 (d, J=8.7 Hz, 1H), 8.01 (m, 2H), 7.74 (d, J=8.4 Hz, 2H), 7.52 (d, J=8.1 Hz, 2H), 6.95 (d, J=1.8 Hz, 1H), 3.94 (s, 3H), 1.81 (s, 6H); MS (m/z): 512 (M+1)$^+$.

Example 69

N-(1-(6-(2-cyanopropan-2-yl)pyridin-3-yl)-3-methyl-8-(3-(trifluoromethyl)phenyl)-1H-imidazo[4,5-c]quinolin-2(3H)-ylidene)cyanamide $^1$H NMR (300 MHz, DMSO-d$_6$): δ 9.29 (s, 1H), 9.08 (d, J=2.4 Hz, 1H), 8.44 (dd, J=2.4, 8.4 Hz, 1H), 8.23 (d, J=9 Hz, 1H), 8.05 (dd, J=1.8, 9 Hz, 1H), 7.99 (d, J=8.4 Hz, 1H), 7.72 (m, 2H), 7.56 (m, 2H), 3.94 (s, 3H), 1.78 (s, 6H); MS (m/z): 512 (M+1)$^+$.

Example 70

N-(1-(6-(2-cyanopropan-2-yl)pyridin-3-yl)-3-methyl-8-(5-(trifluoromethyl)pyridin-3-yl)-1H-imidazo[4,5-cquinolin-2(3H)-ylidene)cyanamide $^1$H NMR (300 MHz, DMSO-d$_6$): δ 9.32 (s, 1H), 9.08 (d, J=2.4 Hz, 1H), 8.99 (s, 1H), 8.73 (s, 1H), 8.43 (dd, J=2.4, 8.4 Hz, 1H), 8.25 (m, 2H), 8.14 (dd, J=1.8, 8.7 Hz, 1H), 7.99 (d, J=8.4 Hz, 1H), 3.94 (s, 3H), 1.79 (s, 6H); MS (m/z): 513 (M+1)$^+$.

Example 71 tert-butyl (5-(2-(cyanoimino)-1-(6-(2-cyanopropan-2-yl)pyridin-3-yl)-3-methyl-2,3-dihydro-1H-imidazo[4,5-c]quinolin-8-yl)pyridin-3-yl)methylcarbamate $^1$H NMR (300 MHz, DMSO-d$_6$): δ 9.29 (s, 1H), 9.08 (d, J=2.4 Hz, 1H), 8.42 (m, 2H), 8.25 (m, 1H), 8.20 (d, J=1.8 Hz, 1H), 8.02 (d, J=8.4 Hz, 1H), 7.96 (dd, J=2.1, 9 Hz, 1H), 7.79 (s, 1H), 7.47 (s, 2H), 6.97 (s, 1H), 3.93 (s, 3H), 1.82 (s, 6H), 1.38 (s, 9H); MS (m/z): 574 (M+1)$^+$.

Example 72 tert-butyl 4-(5-(2-(cyanoimino)-1-(6-(2-cyanopropan-2-yl)pyridin-3-yl)-3-methyl-2,3-dihydro-1H-imidazo[4,5-c]quinolin-8-yl)pyridin-2-yl)piperazine-1-carboxylate $^1$H NMR (300 MHz, DMSO-d$_6$): δ 9.20 (s, 1H), 9.08 (d, J=2.4 Hz, 1H), 8.41 (dd, J=2.4, 8.4 Hz, 1H), 8.14 (d, J=9 Hz, 1H), 7.95 (m, 3H), 7.54 (dd, J=2.7, 9 Hz, 1H), 6.83 (d, J=9 Hz, 1H), 6.78 (d, J=1.8 Hz, 1H), 3.91 (s, 3H), 3.51 (m, 4H), 3.42 (m, 4H), 1.86 (s, 6H), 1.43 (s, 9H); MS (m/z): 629 (M+1)$^+$.

Example 73

N-(1-(6-(2-cyanopropan-2-yl)pyridin-3-yl)-8-(1H-indol-5-yl)-3-methyl-1H-imidazo[4,5-c]quinolin-2(3H)-ylidene)cyanamide $^1$H NMR (300 MHz, DMSO-d$_6$): δ 11.23 (s, 1H), 9.21 (s, 1H), 9.11 (d, J=2.1 Hz, 1H), 8.44 (dd, J=2.4, 8.4 Hz, 1H), 8.16 (d, J=9 Hz, 1H), 8.02 (m, 2H), 7.57 (s, 1H), 7.39 (m, 2H), 6.97 (m, 2H), 6.46 (s, 1H), 3.93 (s, 3H), 1.82 (s, 6H); MS (m/z): 483 (M+1)$^+$.

Example 74

N-(8-(5-chloro-6-methoxypyridin-3-yl)-1-(6-(2-cyanopropan-2-yl)pyridin-3-yl)-3-methyl-1H-imidazo[4,5-c]quinolin-2(3H)-ylidene)cyanamide $^1$H NMR (300 MHz, DMSO-d$_6$): δ 9.28 (s, 1H), 9.04 (d, J=2.1 Hz, 1H), 8.38 (dd, J=2.4, 8.4 Hz, 1H), 8.17 (m, 2H), 7.97 (d, J=7.2 Hz, 1H), 7.86 (d, J=9 Hz, 1H), 7.72 (d, J=2.4 Hz, 1H), 7.07 (s, 1H), 3.93 (s, 3H), 3.79 (s, 3H), 1.74 (s, 6H); MS (m/z): 509 (M+1)$^+$.

Example 75

N-(8-(2-aminopyrimidin-5-yl)-1-(6-(2-cyanopropan-2-yl)pyridin-3-yl)-3-methyl-1H-imidazo[4,5-c]quinolin-2(3H)-ylidene)cyanamide $^1$H NMR (300 MHz, DMSO-d$_6$): δ 9.22 (s, 1H), 9.07 (d, J=2.1 Hz, 1H), 8.40 (dd, J=2.7, 8.7 Hz, 1H), 8.20 (s, 2H), 8.15 (d, J=9 Hz, 1H), 8.02 (d, J=8.1 Hz, 1H), 7.98 (d, J=3 Hz, 1H), 6.95 (s, 2H), 6.77 (d, J=1.8 Hz, 1H), 3.92 (s, 3H), 1.84 (s, 6H); MS (m/z): 461 (M+1)$^+$.

Example 76

N-(1-(6-(2-cyanopropan-2-yl)pyridin-3-yl)-3-methyl-8-(6-(piperidin-1-yl)pyridin-3-yl)-1H-imidazo[4,5-c]quinolin-2(3H)-ylidene)cyanamide $^1$H NMR (300 MHz, DMSO-d$_6$): δ 9.19 (s, 1H), 9.08 (d, J=1.8 Hz, 1H), 8.41 (dd, J=2.7 Hz, 8.4 Hz, 1H), 8.13 (d, J=8.7 Hz, 1H), 8.03 (d, J=8.4 Hz, 1H), 7.94 (dd, J=1.8, 9 Hz, 2H), 7.47 (dd, J=2.7, 9 Hz, 1H), 6.76 (m, 2H), 3.92 (s, 3H), 3.54 (m, 4H), 1.87 (s, 6H), 1.52 (m, 6H); MS (m/z): 528 (M+1)+.

Example 77

N-(1-(6-(2-cyanopropan-2-yl)pyridin-3-yl)-8-(1H-indazol-6-yl)-3-methyl-1H-imidazo[4,5-c]quinolin-2(3H)-ylidene)cyanamide $^1$H NMR (300 MHz, DMSO-d$_6$): δ 13.18 (s, 1H), 9.26 (s, 1H), 9.11 (d, J=2.4 Hz, 1H), 8.45 (dd, J=2.7, 8.4 Hz, 1H), 8.22 (d, J=8.7 Hz, 1H), 8.06 (m, 2H), 8.01 (m, 1H), 7.74 (d, J=8.4 Hz, 1H), 7.61 (s, 1H), 7.02 (s, 1H), 6.88 (d, J=8.4 Hz, 1H), 3.94 (s, 3H), 1.79 (s, 6H); MS (m/z): 484 (M+1)+.

Example 78

N-(1-(6-(2-cyanopropan-2-yl)pyridin-3-yl)-8-(6-fluoro-5-methylpyridin-3-yl)-3-methyl-1H-imidazo[4,5-c]quinolin-2(3H)-ylidene)cyanamide $^1$H NMR (300 MHz, DMSO-d$_6$): δ 9.28 (s, 1H), 9.08 (d, J=1.8 Hz, 1H), 8.42 (dd, J=2.7, 8.4 Hz, 1H), 8.23 (d, J=9 Hz, 1H), 8.02 (m, 2H), 7.90 (m, 2H), 6.91 (d, J=1.8 Hz, 1H), 3.94 (s, 3H), 2.28 (s, 3H), 1.81 (s, 6H); MS (m/z): 477 (M+1)+.

Example 79

N-(1-(6-(2-cyanopropan-2-yl)pyridin-3-yl)-8-(1H-indol-6-yl)-3-methyl-1H-imidazo[4,5-c]quinolin-2(3H)-ylidene)cyanamide $^1$H NMR (300 MHz, DMSO-d$_6$): δ 9.22 (s, 1H), 9.10 (d, J=1.8 Hz, 1H), 8.44 (dd, J=2.4, 8.4 Hz, 1H), 8.32 (s, 1H), 8.19 (d, J=8.7 Hz, 1H), 8.01 (m, 2H), 7.50 (d, J=9 Hz, 2H), 7.40 (m, 1H), 6.98 (d, J=1.8 Hz, 1H), 6.76 (m, 1H), 6.45 (s, 1H), 3.94 (s, 3H), 1.82 (m, 6H); MS (m/z): 483 (M+1)+.

Example 80

N-(1-(6-(2-cyanopropan-2-yl)pyridin-3-yl)-8-(4-fluorophenyl)-3-methyl-1H-imidazo[4,5-c]quinolin-2(3H)-ylidene)cyanamide $^1$H NMR (300 MHz, DMSO-d$_6$): δ 9.26 (s, 1H), 9.09 (d, J=2.1 Hz, 1H), 8.42 (dd, J=2.7, 8.7 Hz, 1H), 8.19 (d, J=9 Hz, 1H), 7.97 (m, 2H), 7.35 (m, 2H), 7.21 (m, 2H), 6.89 (d, J=1.8 Hz, 1H), 3.94 (s, 3H), 1.83 (s, 6H); MS (m/z): 462 (M+1)+.

Example 81

N-(1-(6-(2-cyanopropan-2-yl)pyridin-3-yl)-3-methyl-8-(pyridin-4-yl)-1H-imidazo[4,5-c]quinolin-2(3H)-ylidene)cyanamide $^1$H NMR (300 MHz, DMSO-d$_6$): δ 9.31 (s, 1H), 9.11 (d, J=2.4 Hz, 1H), 8.58 (d, J=6 Hz, 2H), 8.43 (dd, J=2.4, 8.4 Hz, 1H), 8.25 (d, J=8.7 Hz, 1H), 8.04 (m, 2H), 7.31 (m, 2H), 7.05 (d, J=1.8 Hz, 1H), 3.94 (s, 3H), 1.85 (s, 6H); MS (m/z): 445 (M+1)+.

Example 82

N-(1-(6-(2-cyanopropan-2-yl)pyridin-3-yl)-3-methyl-8-(naphthalen-1-yl)-1H-imidazo[4,5-c]quinolin-2(3H)-ylidene)cyanamide $^1$H NMR (300 MHz, DMSO-d$_6$): δ 9.32 (s, 1H), 9.01 (d, J=2.1 Hz, 1H), 8.45 (dd, J=2.4, 8.4 Hz, 1H), 8.28 (d, J=8.7 Hz, 1H), 7.86 (m, 2H), 7.80 (m, 2H), 7.62 (s, 1H), 7.53 (m, 1H), 7.33 (m, 3H), 6.82 (d, J=1.2 Hz, 1H), 3.95 (s, 3H), 1.41 (s, 6H); MS (m/z): 494 (M+1)+.

Example 83

N-(8-(6-amino-5-(trifluoromethyl)pyridin-3-yl)-1-(4-(2-cyanopropan-2-yl)phenyl)-1H-imidazo[4,5-c]quinolin-2(3H)-ylidene)cyanamide $^1$H NMR (300 MHz, DMSO-d$_6$): δ 13.81 (s, 1H), 8.90 (s, 1H), 8.16 (s, 1H), 8.12 (d, J=8.7 Hz, 1H), 7.96 (s, 1H), 7.86 (d, J=8.4 Hz, 2H), 7.79 (d, J=8.4 Hz, 2H), 7.61 (s, 1H), 6.99 (s, 1H), 6.70 (s, 2H), 1.74 (s, 6H); MS (m/z): 513 (M+1)+.

Example 84

N-(8-(5-amino-6-methoxypyridin-3-yl)-1-(4-(2-cyanopropan-2-yl)phenyl)-3-methyl-1H-imidazo[4,5-c]quinolin-2(3H)-ylidene)cyanamide $^1$H NMR (300 MHz, DMSO-d$_6$): δ 9.17 (s, 1H), 8.14 (d, J=9 Hz, 1H), 7.90 (m, 4H), 7.79 (d, J=7.5 Hz, 1H), 7.12 d, J=1.8 Hz, 1H), 6.90 (d, J=1.8 Hz, 1H), 6.79 (s, 1H), 5.07 (s, 2H), 3.89 (s, 3H), 3.84 (s, 3H), 1.81 (s, 6H); MS (m/z): 489 (M+1)+.

Example 85

N-(1-(4-(2-cyanopropan-2-yl)phenyl)-8-(pyridin-3-yl)-1H-imidazo[4,5-c]quinolin-2(3H)-ylidene)cyanamide $^1$H NMR (300 MHz, DMSO-d$_6$): δ 13.81 (s, 1H). 8.96 (d, J=3 Hz, 1H), 8.57 (d, J=3 Hz, 1H), 8.51 (d, J=1.2 Hz, 1H), 8.20 (d, J=8.4 Hz, 1H), 8.06 (d, J=5.4 Hz, 1H), 7.91 (d, J=5.1 Hz, 2H), 7.82 (d, J=5.1 Hz, 2H), 7.74 (d, J=6.4 Hz, 2H) 7.43 (m, 1H), 1.83 (s, 6H); MS (m/z): 430 (M+1)+.

Example 86

N-(1-(4-(2-cyanopropan-2-yl)phenyl)-3-ethyl-8-(pyridin-3-yl)-1H-imidazo[4,5-c]quinolin-2(3H)-ylidene)cyanamide $^1$H NMR (300 MHz, CDCl$_3$): δ 8.97 (s, 1H), 8.59 (bs, 2H), 8.31 (d, J=9 Hz, 1H), 7.91 (m, 2H), 7.72 (d, J=8.4 Hz, 2H), 7.57 (d, J=8.4 Hz, 2H), 7.34 (s, 1H), 7.04 (s, 1H), 4.53 (m, 2H), 1.89 (s, 6H), 1.68 (m, 3H); MS (m/z): 458 (M+1)+.

Example 87

N-(1-(4-(2-cyanopropan-2-yl)phenyl)-8-(2-fluoro-5-(trifluoromethyl)phenyl)-3-methyl-1H-imidazo[4,5-c]quinolin-2(3H)-ylidene)cyanamide $^1$H NMR (300 MHz, CDCl$_3$): δ 8.98 (s, 1H), 8.31 (d, J=8.7 Hz, 1H), 7.83 (d, J=8.7 Hz, 3H), 7.67 (m, 4H), 7.21 (s, 2H), 4.01 (s, 3H), 1.83 (s, 6H); MS (m/z): 529 (M+1)+.

Example 88

N-(1-(4-(2-cyanopropan-2-yl)phenyl)-3-methyl-8-(3,4,5-trimethoxyphenyl)-1H-imidazo[4,5-c]quinolin-2(3H)-ylidene)cyanamide $^1$H NMR (300 MHz, DMSO-d$_6$): δ 9.21 (s, 1H), 8.19 (d, J=8.7 Hz, 1H), 7.97 (m, 1H), 7.87 (m, 4H), 6.99 (s, 1H), 6.57 (s, 2H), 3.92 (s, 3H), 3.80 (s, 6H), 3.65 (s, 3H), 1.71 (s, 6H); MS (m/z): 533 (M+1)+.

Example 89 tert-butyl 4-(2-(cyanoimino)-1-(4-(2-cyanopropan-2-yl)phenyl)-3-methyl-2,3-dihydro-1H-imidazo[4,5-c]quinolin-8-yl)-5,6-dihydropyridine-1(2H)-carboxylate $^1$H NMR (300 MHz, DMSO-d$_6$): δ 9.15 (s, 1H), 8.05 (d, J=9 Hz, 1H), 7.92 (m, 5H), 6.69 (s, 1H), 6.32 (bs, 1H), 3.97 (s, 3H), 3.90 (s, 2H), 3.44 (s, 2H), 1.84 (s, 6H), 1.42 (s, 9H), 1.23 (s, 2H); MS (m/z): 548 (M+1)$^+$.

Example 90

N-(1-(4-(2-cyanopropan-2-yl)phenyl)-3-methyl-8-(6-morpholinopyridin-3-yl)-1H-imidazo[4,5-c]quinolin-2(3H)-ylidene)cyanamide $^1$H NMR (300 MHz, DMSO-d$_6$): δ 9.17 (s, 1H), 8.14 (d, J=8.7 Hz, 1H), 7.99 (m, 6H), 7.58 (d, J=8.7 Hz, 1H), 6.84 (s, 1H), 6.81 (s, 1H), 3.91 (s, 3H), 3.70 (bs, 4H), 3.48 (bs, 4H), 1.86 (s, 6H); MS (m/z): 529 (M+1)$^+$.

Example 91

N-(1-(4-(2-cyanopropan-2-yl)phenyl)-8-(6-methoxypyridin-3-yl)-3-methyl-1H-imidazo[4,5-c]quinolin-2(3H)-ylidene)cyanamide $^1$H NMR (300 MHz, DMSO-d$_6$): δ 9.21 (s, 1H), 8.19 (d, J=9 Hz, 1H), 8.08 (s, 1H), 8.00 (d, J=8.1 Hz, 1H), 7.91 (s, 4H), 7.67 (d, J=8.1 Hz, 1H), 6.84 (bs, 2H), 3.92 (s, 3H), 3.84 (s, 3H), 1.85 (s, 6H); MS (m/z): 474 (M+1)$^+$.

Example 92

N-(8-(6-amino-5-(trifluoromethyl)pyridin-3-yl)-3-methyl-1-(5-phenylpyridin-3-yl)-1H-imidazo[4,5-c]quinolin-2(3H)-ylidene)cyanamide $^1$H NMR (300 MHz, DMSO-d$_6$): δ 9.31 (d, J=1.8 Hz, 1H), 9.24 (s, 1H), 9.06 (d, J=2.4 Hz, 1H), 8.76 (m, 1H), 8.26 (s, 1H), 8.19 (d, J=9 Hz, 1H), 8.06 (dd, J=9 Hz, 2.1 Hz, 1H), 7.82 (d, J=6.9 Hz, 2H), 7.56 (m, 4H), 6.98 (d, J=1.5 Hz, 1H), 6.75 (s, 2H), 3.90 (s, 3H);
MS (m/z): 537 (M+1)$^+$.

Example 93

N-(8-(5-amino-6-methoxypyridin-3-yl)-3-methyl-1-(5-phenylpyridin-3-yl)-1H-imidazo[4,5-c]quinolin-2(3H)-ylidene)cyanamide $^1$H NMR (300 MHz, DMSO-d$_6$): δ 9.35 (d, J=1.8 Hz, 1H), 9.24 (s, 1H), 9.05 (d, J=2.1 Hz, 1H), 8.73 (s, 1H), 8.19 (d, J=9 Hz, 1H), 7.83 (d, J=7.2 Hz, 3H), 7.53 (m, 3H), 7.19 (d, J=2.1 Hz, 1H), 7.01 (d, J=1.8 Hz, 1H), 6.86 (d, J=2.1 Hz, 1H), 5.02 (s, 2H), 3.90 (s, 3H), 3.86 (s, 3H); MS (m/z): 499 (M+1)$^+$.

Example 94

N-(1-(4-(2-cyanopropan-2-yl)phenyl)-8-(1H-indol-6-yl)-3-methyl-1H-imidazo[4,5-c]quinolin-2(3H)-ylidene)cyanamide $^1$H NMR (300 MHz, DMSO-d$_6$): δ 11.20 (s, 1H), 9.18 (s, 1H), 8.32 (s, 1H), 8.18 (d, J=8.7 Hz, 1H), 8.02 (d, J=9 Hz, 1H), 7.90 (m, 4H), 7.53 (s, 1H), 7.50 (d, J=8.1 Hz, 1H), 7.41 (m, 1H), 7.03 (s, 1H), 6.77 (d, J=8.1 Hz, 1H), 6.44 (s, 1H), 3.93 (s, 3H), 1.79 (s, 6H); MS (m/z): 482 (M+1)$^+$.

Example 95

N-(8-(5-amino-6-methoxypyridin-3-yl)-1-(6-(2-cyanopropan-2-yl)pyridin-3-yl)-3-methyl-1H-imidazo[4,5-c]quinolin-2(3H)-ylidene)cyanamide $^1$H NMR (300 MHz, DMSO-d$_6$): δ 9.20 (s, 1H), 9.04 (d, J=2.1 Hz, 1H), 8.41 (dd, J=8.4, 2.4 Hz, 1H), 8.15 (d, J=8.7 Hz, 1H), 8.03 (d, J=8.4 Hz, 1H), 7.80 (d, J=9 Hz, 1H), 7.14 (d, J=1.8 Hz, 1H), 6.88 (s, 1H), 6.75 (s, 1H), 5.08 (s, 2H), 3.89 (s, 3H), 3.84 (s, 3H), 1.80 (s, 6H); MS (m/z): 490 (M+1)$^+$.

Example 96

N-(8-(6-amino-5-(trifluoromethyl)pyridin-3-yl)-1-(6-(2-cyanopropan-2-yl)pyridin-3-yl)-1H-imidazo[4,5-c]quinolin-2(3H)-ylidene)cyanamide $^1$H NMR (300 MHz, DMSO-d$_6$): δ 8.96 (m, 2H), 8.33 (dd, J=8.4, 2.1 Hz, 1H), 8.22 (bs, 8.14 (d, J=9.0 Hz, 2H), 7.98 (m, 2H), 7.64 (d, J=1.8 Hz, 1H), 6.98 (bs, 1H), 6.74 (s, 2H), 1.79 (s, 6H); MS (m/z): 514 (M+1)$^+$.

Example 97

N-(8-(6-amino-5-(trifluoromethyl)pyridin-3-yl)-1-(3,5-dimethoxyphenyl)-3-methyl-1H-imidazo[4,5-c]quinolin-2(3H)-ylidene)cyanamide $^1$H NMR (300 MHz, DMSO-d$_6$): δ 9.17 (s, 1H), 8.34 (s, 1H), 8.15 (d, J=9 Hz, 1H), 8.04 (dd, J=3 Hz, J=9 Hz, 1H), 7.58 (s, 1H), 7.11 (d, J=3 Hz, 1H), 7.06-7.05 (m, 2H), 6.86 (s, 1H), 6.80 (s, 2H), 3.84 (s, 3H), 3.79 (s, 6H); MS (m/z): 520 (M+1)$^+$.

Example 98

N-(8-(6-amino-5-(trifluoromethyl)pyridin-3-yl)-1-(2,6-dimethoxypyridin-3-yl)-3-methyl-1H-imidazo[4,5-c]quinolin-2(3H)-ylidene)cyanamide $^1$H NMR (300 MHz, DMSO-d$_6$): δ 9.17 (s, 1H), 8.40 (s, 1H), 8.17 (d, J=9 Hz, 2H), 8.06 (d, J=3 Hz, 1H), 7.61 (d, J=3 Hz, 1H), 7.18 (d, J=3 Hz, 1H), 6.18 (s, 2H), 6.72 (d, J=3 Hz, 1H), 4.00 (s, 3H), 3.86 (s, 3H), 3.80 (s, 3H); MS (m/z): 521 (M+1)$^+$.

Example 99

N-(8-(5-amino-6-methoxypyridin-3-yl)-1-(3,5-dimethoxyphenyl)-3-methyl-1H-imidazo[4,5-c]quinolin-2(3H)-ylidene)cyanamide $^1$H NMR (300 MHz, DMSO-d$_6$): δ 9.17 (s, 1H), 8.16 (d, J=9 Hz, 1H), 7.83 (dd, J=3 Hz, J=9 Hz, 1H), 7.29 (d, J=3 Hz, 1H), 7.17 (d, J=3 Hz, 1H), 7.06 (d, J=3 Hz, 2H), 6.95 (m, 2H), 5.04 (s, 2H), 3.90 (s, 3H), 3.85 (m, 3H), 3.81 (s, 6H); MS (m/z): 482 (M+1)$^+$.

Example 100

N-(1-(2,4-dimethoxyphenyl)-3-methyl-8-(quinolin-3-yl)-1H-imidazo[4,5-c]quinolin-2(3H)-ylidene)cyanamide $^1$H NMR (300 MHz, DMSO-d$_6$): δ 9.22 (s, 1H), 8.97 (d, J=3 Hz, 1H), 8.34 (d, J=3 Hz, 1H), 8.28 (m, 2H), 8.09 (d, J=9 Hz, 1H), 8.03 (d, J=9 Hz, 1H), 7.85 (m, 1H), 7.75 (m, 2H), 7.33 (d, J=3 Hz, 1H), 7.00 (d, J=3 Hz, 1H), 6.91 (m, 1H), 3.95 (s, 3H), 3.83 (s, 3H), 3.75 (s, 3H); MS (m/z): 487 (M+1)$^+$.

Example 101

N-(1-(2,4-dimethoxyphenyl)-3-methyl-8-(pyridin-3-yl)-1H-imidazo[4,5-c]quinolin-2(3H)-ylidene)cyanamide $^1$H NMR (300 MHz, DMSO-d$_6$): δ 9.21 (s, 1H), 8.60 (m, 2H), 8.23 (d, J=9 Hz, 1H), 8.06 (dd, J=3 Hz, J=9 Hz, 1H), 7.84 (d, J=9 Hz, 1H), 7.72 (d, J=9 Hz, 1H), 7.49 (m, 1H), 7.17 (d, J=3 Hz, 1H), 6.96 (d, J=3 Hz, 1H), 6.87 (dd, J=3 Hz, J=9 Hz, 1H), 3.95 (s, 3H), 3.82 (s, 3H), 3.74 (s, 3H); MS (m/z): 437 (M+1)$^+$.

Example 102

N-(1-(3,5-dimethoxyphenyl)-3-methyl-8-(pyridin-3-yl)-1H-imidazo[4,5-c]quinolin-2(3H)-ylidene)cyanamide $^1$H NMR (300 MHz, DMSO-d$_6$): δ 9.23 (s, 1H), 8.59 (m, 2H), 8.23 (d, J=9 Hz, 1H), 8.06 (dd, J=3 Hz, J=9 Hz, 1H), 7.84 (d, J=9 Hz, 1H), 7.51 (m, 1H), 7.25 (d, J=3 Hz, 1H), 7.08 (d, J=3 Hz, 2H), 6.92 (m, 1H), 3.86 (s, 3H), 3.80 (s, 6H); MS (m/z): 437 (M+1)$^+$.

Example 103

N-(1-(2,4-dimethoxyphenyl)-3-methyl-8-(quinolin-6-yl)-1H-imidazo[4,5-c]quinolin-2(3H)-ylidene)cyanamide $^1$HNMR (300 MHz, DMSO-d$_6$): δ 9.21 (s, 1H), 8.95 (d, J=3 Hz, 1H), 8.38 (d, J=6 Hz, 1H), 8.25 (m, 2H), 8.06 (d, J=6 Hz, 1H), 7.99 (s, 1H), 7.81 (d, J=6 Hz, 1H), 7.75 (d, J=9 Hz, 1H), 7.65 (m, 1H), 7.30 (s, 1H), 7.01 (d, J=3 Hz, 1H), 6.92 (m, 1H), 3.95 (s, 3H), 3.82 (s, 3H), 3.72 (s, 3H); MS (m/z): 487 (M+1)$^+$.

Example 104

N-(1-(2,4-dimethoxyphenyl)-3-methyl-8-(4-(trifluoromethyl)phenyl)-1H-imidazo[4,5-c]quinolin-2(3H)-ylidene)cyanamide $^1$H NMR (300 MHz, DMSO-d$_6$): δ 9.22 (s, 1H), 8.23 (d, J=9 Hz, 1H), 8.05 (dd, J=3 Hz, J=9 Hz, 1H), 7.80 (m, 3H), 7.72 (d, J=9 Hz, 1H), 7.63 (m, 2H), 7.21 (d, J=3 Hz, 1H), 6.96 (d, J=3 Hz, 1H), 6.87 (dd, J=3 Hz, J=6 Hz, 1H), 3.95 (s, 3H), 3.82 (s, 3H), 3.74 (s, 3H); MS (m/z): 504 (M+1)$^+$.

Example 105

N-(8-(6-amino-5-(trifluoromethyl)pyridin-3-yl)-3-methyl-1-(4-(trifluoromethoxy)phenyl)-1H-imidazo[4,5-c]quinolin-2(3H)-ylidene)cyanamide $^1$H NMR (300 MHz, DMSO-d$_6$): δ 9.20 (s, 1H), 8.34 (s, 1H), 8.14 (s, 1H), 8.03 (m, 3H), 7.73 (d, J=9 Hz, 2H), 7.52 (s, 1H), 6.88 (d, J=3 Hz, 1H), 6.75 (s, 2H), 3.80 (s, 3H); MS (m/z): 544 (M+1)$^+$.

Example 106

N-(8-(5-amino-6-methoxypyridin-3-yl)-3-methyl-1-(4-(trifluoromethoxy)phenyl)-1H-imidazo[4,5-c]quinolin-2(3H)-ylidene)cyanamide $^1$H NMR (300 MHz, DMSO-d$_6$): δ 9.20 (s, 1H), 8.18 (d, J=9 Hz, 1H), 8.03 (d, J=9 Hz, 2H), 7.83 (m, 3H), 7.25 (d, J=3 Hz, 1H), 6.92 (m, 2H), 5.08 (s, 2H), 3.88 (s, 6H); MS (m/z): 506 (M+1)$^+$.

Example 107

N-(3-methyl-8-(quinolin-3-yl)-1-(4-(trifluoromethoxy)phenyl)-1H-imidazo[4,5-c]quinolin-2(3H)-ylidene)cyanamide $^1$H NMR (300 MHz, DMSO-d$_6$): δ 9.28 (s, 1H), 8.76 (d, J=3 Hz, 1H), 8.33 (m, 2H), 8.21 (dd, J=3 Hz, J=6 Hz, 1H), 8.08 (m, 3H), 7.99 (d, J=6 Hz, 1H), 7.83 (m, 3H), 7.70 (m, 1H), 7.18 (d, J=3 Hz, 1H), 3.90 (s, 3H); MS (m/z): 511 (M+1)$^+$.

Example 108

N-(3-methyl-8-(pyridin-3-yl)-1-(4-(trifluoromethoxy)phenyl)-1H-imidazo[4,5-c]quinolin-2(3H)-ylidene)cyanamide $^1$H NMR (300 MHz, DMSO-d$_6$): δ 9.26 (s, 1H), 8.59 (m, 2H), 8.25 (d, J=9 Hz, 1H), 8.06 (m, 3H), 7.79 (d, J=3 Hz, 2H), 7.70 (m, 1H), 7.42 (m, 1H), 7.02 (d, J=3 Hz, 1H), 3.90 (s, 3H); MS (m/z): 461 (M+1)$^+$.

Example 109

N-(3-methyl-8-(pyridin-4-yl)-1-(4-(trifluoromethoxy)phenyl)-1H-imidazo[4,5-c]quinolin-2(3H)-ylidene)cyanamide $^1$H NMR (300 MHz, DMSO-d$_6$): δ 9.29 (s, 1H), 8.56 (m, 2H), 8.27 (d, J=9 Hz, 1H), 8.09 (m, 3H), 7.82 (d, J=9 Hz, 2H), 7.32 (m, 2H), 7.10 (d, J=3 Hz, 1H), 3.88 (s, 3H); MS (m/z): 461 (M+1)$^+$.

Example 110

N-(8-(6-amino-5-(trifluoromethyl)pyridin-3-yl)-3-(cyanomethyl)-1-(6-(2-cyanopropan-2-yl)pyridin-3-yl)-1H-imidazo[4,5-c]quinolin-2(3H)-ylidene)cyanamide $^1$HNMR (300 MHz, DMSO-d$_6$): δ 9.15 (m, 2H), 8.47 (dd, J=2.7, 11.1 Hz, 1H), 8.36 (s, 1H), 8.23 (d, J=8.7 Hz, 1H), 8.08

(m, 1H), 8.02 (d, J=8.4 Hz, 1H), 7.70 (s, 1H), 7.36 (s, 1H), 6.75 (m, 4H), 1.82 (s, 6H); MS (m/z): 553.2 (M+1)$^+$.

Example 111

N-(8-(6-amino-5-(trifluoromethyl)pyridin-3-yl)-3-methyl-1-(6-(trifluoromethyl)pyridin-3-yl)-1H-imidazo[4,5-c]quinolin-2(3H)-ylidene)cyanamide $^1$H NMR (300 MHz, DMSO-d$_6$): δ 9.31 (d, J=1.8 Hz, 1H), 9.25 (s, 1H), 8.71 (dd, J=2.1, 8.4 Hz, 1H), 8.37 (m, 2H), 8.20 (d, J=8.7 Hz, 1H), 8.02 (dd, J=2.1, 9.0 hz, 1H), 7.48 (s, 1H), 6.82 (d, J=1.5 Hz, 1H), 6.77 (s, 2H), 3.92 (s, 2H); MS (m/z): 529.1 (M+1)$^+$.

Example 112

N-(3-methyl-8-(6-mo rp holinopyridin-3-yl)-1-(6-(trifluoromethyl)pyridin-3-yl)-1H-imidazo[4,5-c]quinolin-2(3H)-ylidene)cyanamide $^1$HNMR (300 MHz, DMSO-d$_6$): δ 9.12 (d, J=2.1 Hz, 1H), 9.00 (s, 1H), 8.44 (dd, J=8.1, 2.1 Hz, 1H), 8.20-8.16 (m, 3H), 7.91 (dd, J=8.7, 2.7 Hz, 1H), 6.86 (d, J=1.8 Hz, 1H), 6.73 (d, J=9.0, 1H), 3.9 (s, 3H), 3.76 (t, J=4.8 Hz, 4H), 3.51 (t, J=5.1 Hz, 4H); MS (m/z): 531.1 (M+1)$^+$.

Example 113

N-(8-(6-methoxypyridin-3-yl)-3-methyl-1-(6-(trifluoromethyl)pyridin-3-yl)-1H-imidazo[4,5-c]quinolin-2(3H)-ylidene)cyanamide $^1$H NMR (300 MHz, CD$_3$CN): δ 9.13 (s, 1H), 9.06 (s, 1H), 8.45-8.43 (m, 1H), 8.25-8.16 (m, 3H), 7.94 (dd, J=7.8 Hz, 1.8 Hz, 1H), 7.58 (dd, J=8.7 Hz, 2.7 Hz, 1H), 6.91 (d, J=1.8 Hz, 1H), 6.80 (d, J=8.4 Hz, 1H), 3.93 (s, 6H); MS (m/z): 476 (M+1)$^+$.

Example 114

N-(8-(1H-indol-5-yl)-3-methyl-1-(6-(trifluoromethyl)pyridin-3-yl)-1H-imidazo[4,5-c]quinolin-2 (3H)-ylidene)cyanamide $^1$H NMR (300 MHz, DMSO-d$_6$): δ 9.38 (s, 1H), 9.23 (s, 1H), 8.77-8.75 (m, 1H), 8.46 (d, J=8.4 Hz, 1H) 8.20 (d, J=9.0 Hz, 1H), 8.08-8.05 (m, 1H), 7.50 (s, 1H), 7.41-7.40 (m, 1H), 7.04 (d, J=8.4 Hz, 1H), 6.86 (s, 1H), 6.40 (s, 1H), 3.92 (s, 1H); MS (m/z): 484.2 (M+1)$^+$.

Example 115

N-(1-(6-(2-cyanopropan-2-yl)pyridin-3-yl)-8-(4-(isopropylthio) phenyl)-3-methyl-1H-imidazo[4,5-c]quinolin-2(3H)-ylidene)cyanamide $^1$H NMR (300 MHz, DMSO-d$_6$): δ 8.84 (m, 2H), 8.20 (d, J=9 Hz, 1H), 7.99 (dd, J=2.4, 8.4 Hz, 1H), 7.91 (m, 1H), 7.83 (dd, J=1.8, 8.7 Hz, 1H), 7.37 (m, 2H), 7.30 (s, 1H), 7.24 (d, J=1.8 Hz, 1H), 3.69 (m, 3H), 3.41 (m, 1H), 1.85 (s, 6H), 1.34 (m, 6H); MS (m/z): 518 (M+1)$^+$.

Example 116

N-(8-(4-(butylthio)phenyl)-1-(6-(2-cyanopropan-2-yl)pyridin-3-yl)-3-methyl-1H-imidazo[4,5-c]quinolin-2(3H)-ylidene)cyanamide $^1$H NMR (300 MHz, DMSO-d$_6$): 8.85 (d, J=2.4 Hz, 1H), 8.82 (s, 1H), 8.18 (d, J=9 Hz, 1H), 7.98 (dd, J=2.4, 8.4 Hz, 1H), 7.90 (d, J=8.4 Hz, 1H), 7.82 (dd, J=2.1, 9 Hz, 1H), 7.28 (m, 4H), 4.76 (s, 2H), 3.72 (s, 3H), 2.95 (m, 2H), 2.92 (m, 2H), 1.89 (s, 6H), 1.54 (s, 3H); MS (m/z): 533 (M+1)$^+$.

Example 117 tert-butyl 4-(2-(cyanoimino)-1-(6-(2-cyanopropan-2-yl)pyridin-3-yl)-3-methyl-2,3-dihydro-1H-imidazo[4,5-c]quinolin-8-yl)-5,6-dihydropyridine-1(2H)-carboxylate $^1$H NMR (300 MHz, DMSO-d$_6$): δ 9.18 (s, 1H), 9.05 (d, J=2.4 Hz, 1H), 8.38 (dd, J=2.4, 8.4 Hz, 1H), 8.02 (m, 2H), 7.89 (s, 1H), 6.66 (s, 1H), 7.72 (m, 2H), 7.56 (m, 2H), 3.94 (s, 3H), 1.78 (s, 6H); MS (m/z): 549 (M+1)$^+$.

Example 118 tert-butyl 4-(2-(cyanoimino)-3-methyl-1-(6-(trifluoromethyl)pyridin-3-yl)-2,3-dihydro-1H-imidazo[4,5-c]quinolin-8-yl)-5,6-dihydropyridine-1(2H)-carboxylate $^1$H NMR (300 MHz, CD$_3$CN): δ 9.11 (s, 1H), 8.96 (s, 1H), 8.41 (m, 1H), 8.21 (d, J=8.4 Hz, 1H), 8.08 (d, J=9.3 Hz, 1H), 7.83 (m, 1H), 6.63 (s, 1H), 6.19 (br s, 1H), 4.01 (m, 2H), 3.88 (s, 3H), 3.51-3.48 (m, 2H), 1.98-1.95 (m, 2H), 1.47 (s, 9H); MS (m/z): 550.2 (M+1)$^+$.

Example 119 tert-butyl 4-(5-(2-(cyanoimino)-1-(6-(2-cyanopropan-2-yl)pyridin-3-yl)-3-methyl-2,3-dihydro-1H-imidazo[4,5-c]quinolin-8-yl)-3-methylpyridin-2-yl) piperazine-1-carboxylate $^1$H NMR (300 MHz, DMSO-d$_6$): δ 9.24 (s, 1H), 9.08 (d, J=2.4 Hz, 1H), 8.41 (dd, J=2.4, 8.4 Hz, 1H), 8.18 (d, J=2.4, 8.4 Hz, 1H), 8.03 (d, J=8.7 Hz, 1H), 7.95 (m, 2H), 7.57 (s, 1H), 6.85 (s, 1H), 3.92 (s, 3H), 3.47 (s, 4H), 3.05 (s, 4H), 2.27 (s, 3H), 1.84 (s, 6H), 1.44 (s, 9H); MS (m/z): 643 (M+1)$^+$.

Example 120

N-(1-(6-(2-cyanopropan-2-yl)pyridin-3-yl)-8-(2,4-dioxo-1,2,3,4-tetrahydropyrimidin-5-yl)-3-methyl-1H-imidazo[4,5-c]quinolin-2(3H)-ylidene) cyanamide $^1$H NMR (300 MHz, DMSO-d$_6$): δ 9.18 (s, 1H), 8.95 (d, J=2.4 Hz, 1H), 8.29 (dd, J=2.4, 8.4 Hz, 1H), 8.05 (d, J=8.7 Hz, 1H), 7.89 (d, J=8.4 Hz, 1H), 7.78 (dd, J=1.8, 9 Hz, 1H), 7.62 (d, J=4.5 Hz, 1H), 7.33 (d, J=1.8 Hz, 1H), 3.90 (s, 3H), 1.82 (s, 6H); MS (m/z): 478 (M+1)$^+$.

Example 121

N-(8-(3-chloro-2-morpholinopyridin-4-yl)-1-(6-(2-cyanopropan-2-yl)pyridin-3-yl)-3-methyl-1H-imidazo[4,5-c]quinolin-2(3H)-ylidene)cyanamide $^1$H NMR (300 MHz, DMSO-$d_6$): δ 9.32 (s, 1H), 9.02 (d, J=2.1 Hz, 1H), 8.36 (dd, J=2.4, 8.4 Hz, 1H), 8.22 (m, 2H), 7.93 (d, J=8.7 Hz, 1H), 7.75 (dd, J=1.8, 8.7 Hz, 1H), 6.92 (m, 2H), 3.92 (s, 3H), 3.75 (s, 4H), 3.20 (s, 4H), 1.73 (s, 6H); MS (m/z): 565 (M+1)$^+$.

Example 122 tert-butyl 5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-ylcarbamate Sodium hydride (0.255 mmol) was added to a solution of N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (Example 5, 0.102 mmol) in DMF and the solution was stirred for 30 minutes. Di-tert-butyl dicarbonate (0.255 mmol) was added and the reaction mixture was stirred for another 6 h. After completion of the reaction, the solvent was evaporated. The residue was dissolved in ethyl acetate and partitioned with water. The ethyl acetate layer was separated and dried over sodium sulfate. The solvent was evaporated and the crude solid was purified (silica gel column, CHCl$_3$/MeOH as eluent) to obtain the title compound. $^1$H NMR (300 MHz, DMSO-$d_6$): δ 9.47 (s, 3H), 9.29 (s, 1H), 9.05 (d, J=2.1 Hz, 1H), 8.59 (s, 1H), 8.40 (dd, J=2.1, 8.4 Hz, 1H), 8.24 (d, J=9 Hz, 1H), 8.11 (d, J=8.4 Hz, 2H), 7.04 (s, 1H), 3.91 (s, 3H), 3.06 (s, 6H), 1.65 (s, 9H); MS (m/z): 628 (M+1)$^+$.

Example 123 tert-butyl 5-(2-(cyanoimino)-1-(6-methoxypyridin-3-yl)-3-methyl-2,3-dihydro-1H-imidazo[4,5-c]quinolin-8-yl)-3-(trifluoromethyl)pyridin-2-ylcarbamate The title compound was prepared by following the procedure as described for Example 122, using N-(8-(6-amino-5-(trifluoromethyl)pyridin-3-yl)-1-(6-methoxypyridin-3-yl)-3-methyl-1H-imidazo[4,5-c]quinolin-2(3H)-ylidene)cyanamide (Example 1) instead of N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide. $^1$H NMR (300 MHz, DMSO-$d_6$): δ 9.54 (s, 1H), 9.26 (s, 1H), 8.84 (s, 1H), 8.64 (d, J=2.7 Hz, 1H), 8.14 (m, 3H), 7.91 (s, 1H), 7.13 (m, 2H), 4.19 (s, 3H), 3.82 (s, 3H), 1.41 (s, 9H); MS (m/z): 591 (M+1)$^+$.

Example 124

N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)benzenesulfonamide Step 1: N-(5-bromo-2-methoxypyridin-3-yl)benzenesulfonamide 5-bromo-2-methoxypyridin-3-amine (1.231 mmol) was dissolved in pyridine (3 ml) at 0° C. Benzene sulfonyl chloride (1.847 mmol) was added drop wise and the reaction mixture was stirred at RT for 2 h. The reaction mixture was evaporated to dryness and the residue was dissolved in ethyl acetate (100 mL). The ethyl acetate layer was washed with water, separated and dried over sodium sulfate. The organic layer was evaporated to dryness. The crude material obtained was purified by (silica column, EtOAc/Hexane as eluent) to obtain the title compound. $^1$HNMR (300 MHz, DMSO-$d_6$): δ 10.16 (s, 1H), 8.05 (d, J=2.4 Hz, 1H), 7.77 (m, 2H), 7.68 (d, J=2.4 Hz, 1H), 7.64 (m, 1H), 7.55 (m, 1H), 3.61 (s, 3H); MS (m/z): 343 (M)$^+$.

Step 2: (2-(cyanoimino)-1-(4-(2-cyanopropan-2-yl)phenyl)-3-methyl-2,3-dihydro-1H-imidazo[4,5-c]quinolin-8-yl)boronic acid N-(8-bromo-1-(4-(2-cyanopropan-2-yl)phenyl)-3-methyl-1H-imidazo[4,5-c]quinolin-2(3H)-ylidene)cyanamide (2.463 mmol), bis(pinacolato)diboron (1.347 mmol), potassium acetate (2.246 mmol) and (1,1-bis(diphenylphosphino)ferrocene)-dichloropalladium (II) complex with DCM (50 mg) was dissolved in dioxane under argon atmosphere. The reaction mixture was refluxed for 8 h. The reaction mixture was cooled, diluted with ethyl acetate (15 mL) and filtered. The filtrate was concentrated. The crude product was purified (silica gel column ethyl acetate/petroleum ether) to obtain the title compound. $^1$HNMR (300 MHz, DMSO-$d_6$): δ 9.17 (s, 1H), 8.05 (m, 4H), 7.86 (m, 6H), 7.26 (s, 1H), 3.88 (s, 3H), 1.78 (s, 6H); MS (m/z): 411(M+1)$^+$.

Step 3: N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)benzenesulfonamide To the stirred solution (2-(cyanoimino)-1-(4-(2-cyanopropan-2-yl)phenyl)-3-methyl-2,3-dihydro-1H-imidazo[4,5-c]quinolin-8-yl)boronic acid (0.390 mmol) in dry DMF (5 ml) was added N-(5-bromo-2-methoxypyridin-3-yl)benzenesulfonamide (0.39 mmol) followed by catalyst palladium dichlorobis triphenylphosphine (0.039 mmol). Saturated solution of sodium carbonate (0.780 mmol) was added to it and the resulting solution was heated at 111° C. for 8 minutes in microwave. Solvent was removed and the crude material was extracted with EtOAc, washed with brine several times and dried over anhydrous Na$_2$SO$_4$. The solvent was evaporated and the crude solid was purified (silica gel column, CHCl$_3$/MeOH as eluent) to obtain the title compound. $^1$H NMR (300 MHz, DMSO-$d_6$): δ 10.01 (s, 1H), 9.23 (s, 1H), 8.20 (d, J=8.7 Hz, 1H), 7.88 (s, 4H), 7.84 (m, 1H), 7.70 (m, 4H), 7.56 (m, 3H), 6.83 (s, 1H), 3.92 (s, 3H), 3.58 (s, 3H), 1.81 (s, 6H); MS (m/z): 629 (M+1)$^+$.

Example 125

N-(5-(2-(cyanoimino)-1-(6-(2-cyanopropan-2-yl)pyridin-3-yl)-3-methyl-2,3-dihydro-1H-imidazo[4,5-c]quinolin-8-yl)-2-methoxypyridin-3-yl)benzenesulfonamide The title compound was prepared by following the procedure as described for Example 124, using N-(8-bromo-1-(6-(2-cyanopropan-2-yl)pyridin-3-yl)-3-methyl-1H-imidazo[4,5-c]quinolin-2(3H)-ylidene)cyanamide instead of N-(8-bromo-1-(4-(2-cyanopropan-2-yl)phenyl)-3-methyl-1H-imidazo[4,5-c]quinolin-2(3H)-ylidene)cyanamide in step 2. $^1$H NMR (300 MHz, DMSO-$d_6$): δ 10.02 (s, 1H), 9.27 (s, 1H), 9.07 (d, J=2.1 Hz, 1H), 8.43 (dd, J=2.7, 8.7 Hz, 1H), 8.21 (d, J=8.4 Hz, 1H), 8.00 (d, J=8.4 Hz, 1H), 7.85 (dd, J=1.8, 9 Hz, 1H), 7.76 (d, J=2.4 Hz, 1H), 7.60 (m, 4H), 7.51 (m, 2H), 6.85 (s, 1H), 3.93 (s, 3H), 3.58 (s, 3H), 1.82 (s, 6H); MS (m/z): 630 (M+1)$^+$.

Example 126

N-(5-(2-(cyanoimino)-1-(6-(2-cyanopropan-2-yl)pyridin-3-yl)-3-methyl-2,3-dihydro-1H-imidazo[4,5-c]quinolin-8-yl)-2-methoxypyridin-3-yl)methane sulfonamide The title compound was prepared by following the procedure as described for Example 124, using methanesulfonyl chloride instead of benzene sulfonyl chloride in step 1 and N-(8-bromo-1-(6-(2-cyanopropan-2-yl)pyridin-3-yl)-3-methyl-1H-imidazo[4,5-c]quinolin-2(3H)-ylidene)cyanamide instead of N-(8-bromo-1-(4-(2-cyanopropan-2-yl)phenyl)-3-methyl-1H-imidazo[4,5-c]quinolin-2(3H)-ylidene)cyanamide in step 2. $^1$H NMR (300 MHz, DMSO-d$_6$): δ 9.36 (s, 1H), 9.24 (s, 1H), 9.05 (d, J=2.1 Hz, 1H), 8.39 (dd, J=2.4, 8.4 Hz, 1H), 8.29 (s, 1H), 8.19 (d, J=8.7 Hz, 1H), 7.97 (d, J=9 Hz, 1H), 7.90 (dd, J=1.5, 8.7 Hz, 1H), 7.75 (d, J=2.4 Hz, 1H), 7.68 (d, J=2.1 Hz, 1H), 3.91 (s, 6H), 3.02 (s, 3H), 1.82 (s, 6H); MS (m/z): 568 (M+1)$^+$.

Example 127

N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)methanesulfonamide The title compound was prepared by following the procedure as described for Example 124, using methanesulfonyl chloride instead of benzene sulfonyl chloride in step 1. $^1$HNMR (300 MHz, DMSO-d6): δ 9.34 (s, 1H), 9.20 (s, 1H), 8.18 (d, J=8.7 Hz, 1H), 7.90 (m, 5H), 7.71 (d, J=2.1 Hz, 1H), 7.66 (d, J=2.1 Hz, 1H), 6.85 (s, 1H), 3.90 (s, 3H), 3.02 (s, 3H), 1.82 (s, 6H);
MS (m/z): 567 (M+1)$^+$.

Example 128

N-(5-(2-(cyanoimino)-1-(6-(2-cyanopropan-2-yl)pyridin-3-yl)-3-methyl-2,3-dihydro-1H-imidazo[4,5-c]quinolin-8-yl)-4-methylpyridin-2-yl)acetamide Step 1: N-(5-bromo-4-methylpyridin-2-yl)acetamide 5-bromo-4-methylpyridin-2-amine (0.578 mmol) was dissolved in acetic anhydride (5.78 mmol) and heated at 110° C. for 30 minutes. The reaction was quenched with ice. The aqueous reaction mixture neutralized with sodium hydroxide solution was extracted with ethyl acetate. The ethyl acetate layer was separated and dried over sodium sulfate. The organic layer was evaporated to dryness. The crude material was purified (silica column, MeOH/CHCl$_3$). $^1$HNMR (300 MHz, DMSO-d$_6$): 10.53 (s, 1H), 8.34 (s, 1H), 8.06 (s, 1H), 2.30 (s, 3H), 2.05 (s, 3H); MS (m/z): 231 (M+2)$^+$.

Step 2: 2-(cyanoimino)-1-(6-(2-cyanopropan-2-yl)pyridin-3-yl)-3-methyl-2,3-dihydro-1H-imidazo[4,5-c]quinolin-8-ylboronic acid N-(8-bromo-1-(6-(2-cyanopropan-2-yl)pyridin-3-yl)-3-methyl-1H-imidazo[4,5-c]quinolin-2(3H)-ylidene)cyanamide (2.463 mmol) was dissolved in 15 mL of dioxane under argon atmosphere. Bis(pinacolato)diboron (1.347 mmol), potassium acetate (2.246 mmol) and (1,1-bis(diphenylphosphino)ferrocene)-dichloropalladium (II) complex with DCM (50 mg) while stirring. The reaction mixture was refluxed for 8 h. After completion of the reaction, the reaction mixture was cooled and diluted with 15 mL ethyl acetate and filtered through celite. The filtrate was concentrated and the crude product was purified (silica gel column, ethyl acetate/petroleum ether as eluent) to obtain the title compound.

Step 3: N-(5-(2-(cyanoimino)-1-(6-(2-cyanopropan-2-yl)pyridin-3-yl)-3-methyl-2,3-dihydro-1H-imidazo[4,5-c]quinolin-8-yl)-4-methylpyridin-2-yl)acetamide To the stirred solution 2-(cyanoimino)-1-(6-(2-cyanopropan-2-yl)pyridin-3-yl)-3-methyl-2,3-dihydro-1H-imidazo[4,5-c]quinolin-8-ylboronic acid (0.390 mmol) in dry DMF (5 mL) was added N-(5-bromo-4-methylpyridin-2-yl)acetamide (0.390 mmol) followed by catalyst palladium dichlorobis triphenylphosphine (0.039 mmol). Saturated solution of sodium carbonate (0.780 mmol) was added to it and the resulting solution was heated to 111° C. for 8 minutes in microwave. Solvent was evaporated and the crude material was extracted in EtOAc, washed with brine several times and dried over anhydrous Na$_2$SO$_4$. The solvent was evaporated and the crude solid was purified (silica gel column, CHCl$_3$/MeOH as eluent) to obtain the title compound. $^1$H NMR (300 MHz, DMSO-d$_6$): δ 10.46 (s, 1H), 9.26 (s, 1H), 9.02 (d, J=2.4 Hz, 1H), 8.35 (dd, J=2.4, 8.4 Hz, 1H), 8.17 (d, J=8.7 Hz, 1H), 7.91 (m, 3H), 7.70 (dd, J=1.8, 8.7 Hz, 1H), 6.60 (s, 1H), 3.90 (s, 3H), 2.08 (s, 3H), 2.00 (s, 3H), 1.70 (s, 6H); MS (m/z): 516 (M+1)$^+$.

Example 129

N-(1-(4-(2-cyanopropan-2-yl)phenyl)-8-(6-(dimethylamino)-5-(trifluoromethyl)pyridin-3-yl)-3-methyl-1H-imidazo[4,5-c]quinolin-2(3H)-ylidene) cyanamide N-(8-(6-amino-5-(trifluoromethyl)pyridin-3-yl)-1-(4-(2-cyanopropan-2-yl)phenyl)-3-methyl-1H-imidazo[4,5-c]quinolin-2(3H)-ylidene)cyanamide (Example 6, 0.268 mmol) was suspended in DMF, followed by addition of potassium tert-butoxide (0.402 mmol). The reaction mixture was stirred for 15 minutes. Methyl iodide (0.402 mmol) was added to the above mixture and stirred at RT for 3 h. The reaction mixture was concentrated under vacuum and purified on silica gel column using MeOH/CHCl$_3$ (2%) as elute to obtain the title compound. $^1$H NMR (300 MHz, CDCl$_3$): δ 8.90 (s, 1H), 8.24 (d, J=8.7 Hz, 1H), 8.08 (s, 1H), 7.86 (m, 4, H), 7.68 (d, J=8.7 Hz, 2H), 7.17 (s, 1H), 3.97 (s, 3H), 3.06 (s, 6H), 1.88 (s, 6H);
MS (m/z): 555 (M+1)$^+$.

Example 130

N-(1-(6-(2-cyanopropan-2-yl)pyridin-3-yl)-8-(6-((2-methoxyethoxy)methylamino)-5-(trifluoromethyl)pyridin-3-yl)-3-methyl-1H-imidazo[4,5-c]quinolin-2(3H)-ylidene)cyanamide The title compound was prepared by following the procedure as described for Example 129, using methoxyethoxymethyl chloride instead of methyl iodide and N-Methyl-2-pyrrolidone instead of DMF. $^1$H NMR (300 MHz, CDCl$_3$): δ 8.96 (s, 1H), 8.88 (s, 1H), 8.28 (d, J=5.1 Hz, 1H), 8.22 (s, 1H), 8.52-8.00 (m, 2H), 8.84 (d, J=4.8 Hz, 1H), 7.69 (s, 1H), 7.02 (s, 1H), 6.07 (s, 1H), 5.17 (d, J=3 Hz), 4.05 (s, 3H), 3.76 (t, J=2.4 Hz, 2H), 3.57 (t, J=2.7 Hz, 2H), 3.42 (s, 3H), 1.91 (s, 6H); MS (m/z): 616.2 (M+1)$^+$.

Example 131

N-acetyl-N-(5-(2-(cyanoimino)-1-(4-(2-cyanopropan-2-yl)phenyl)-3-methyl-2,3-dihydro-1H-imidazo[4,5-c]quinolin-8-yl)-3-(trifluoromethyl)pyridin-2-yl)acetamide N-(8-(6-amino-5-(trifluoromethyl)pyridin-3-yl)-1-(4-(2-cyanopropan-2-yl)phenyl)-3-methyl-1H-imidazo[4,5-c]quinolin-2(3H)-ylidene)cyanamide (Example 6, 0.076 mmol) and potassium accetate (0.114 mmol) were suspended in acetic anhydride (2 mL) and heated at 80° C. for 30 minutes. The reaction was quenched with ice. The aqueous reaction mixture was neutralized with sodium hydroxide solution and extracted with ethyl acetate. The ethyl acetate layer was separated and dried over sodium sulfate. The organic layer was evaporated to dryness. The crude material obtained was purified (silica gel column, MeOH/CHCl$_3$ as eluent) to obtain the title compound. $^1$H NMR (300 MHz, DMSO-d$_6$): δ 9.28 (s, 1H), 8.70 (s, 1H), 8.36 (s, 1H), 8.2 (d, J=8.4 Hz, 1H), 8.18 (d, J=8.7 Hz, 1H), 7.88 (bs, 4H), 7.05 (s, 1H), 3.92 (s, 3H), 2.19 (s, 6H), 1.72 (s, 6H); MS (m/z): 611(M+1)$^+$.

Example 132

N-acetyl-N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-yl)acetamide The title compound was prepared by following the procedure as described for Example 131, using N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (compound of Example 5) instead of N-(8-(6-amino-5-(trifluoromethyl)pyridin-3-yl)-1-(4-(2-cyanopropan-2-yl)phenyl)-3-methyl-1H-imidazo[4,5-c]quinolin-2(3H)-ylidene)cyanamide. $^1$H NMR (300 MHz, DMSO-d$_6$): δ 9.32 (s, 1H), 9.07 (d, J=2.1 Hz, 1H), 8.78 (d, J=1.5 Hz, 1H), 8.43 (dd, J=8.4 Hz, 2.4 Hz, 1H), 8.37 (d, J=1.5 Hz, 1H), 8.29 (d, J=9 Hz, 1H), 8.20 (dd, J=8.4 Hz, 1.5 Hz, 1H), 7.98 (d, J=8.7 Hz, 1H), 7.08 (d, J=1.8 Hz, 1H), 3.93 (s, 3H), 2.19 (s, 6H), 1.74 (s, 6H); MS (m/z): 612.2 (M+1)$^+$.

Example 133

2-(cyanoimino)-1-(4-(2-cyanopropan-2-yl)phenyl)-3-methyl-2,3-dihydro-1H-imidazo[4,5-c]quinolin-8-yl)-3-(trifluoromethyl)pyridin-2-yl)acetamide N-(8-(6-amino-5-(trifluoromethyl)pyridin-3-yl)-1-(4-(2-cyanopropan-2-yl)phenyl)-3-methyl-1H-imidazo[4,5-c]quinolin-2(3H)-ylidene)cyanamide (Example 6, 0.076 mmol), and potassium accetate (0.114 mmol) were suspended in acetic anhydride (2 mL) and heated at 80° C. for 15 minutes. The reaction was quenched with ice. The aqueous reaction mixture was neutralized with sodium hydroxide solution and extracted with ethyl acetate. The ethyl acetate layer was separated and dried over sodium sulfate. The organic layer was evaporated to dryness. The crude material obtained was purified (silica gel column, MeOH/CHCl$_3$ as eluent) to obtain the title compound. $^1$H NMR (300 MHz, DMSO-d$_6$): δ 10.22 (s, 1H), 9.26 (s, 1H), 8.57 (s, 1H), 8.25 (d, J=9 Hz, 1H), 8.11 (bs, 2H), 7.87 (s, 4H), 7.04 (s, 1H), 3.91 (s, 3H), 2.04 (s, 3H), 1.75 (s, 6H); MS (m/z): 569 (M+1)$^+$.

Example 134

N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-yl)acetamide The title compound was prepared by following the procedure as described for Example 133, using N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (compound of Example 5) instead of N-(8-(6-amino-5-(trifluoromethyl)pyridin-3-yl)-1-(4-(2-cyanopropan-2-yl)phenyl)-3-methyl-1H-imidazo[4,5-c]quinolin-2(3H)-ylidene)cyanamide. $^1$H NMR (300 MHz, DMSO-d$_6$): δ 10.24 (s, 1H), 9.29 (s, 1H), 9.05 (d, J=2.4 Hz, 1H), 8.64 (d, J=2.1, 1H), 8.40 (dd, J=8.7 Hz, 2.7 Hz, 1H), 8.30 (s, 1H), 8.26 (d, J=9 Hz, 1H), 8.13 (dd, J=6.3 Hz, 2.4 Hz, 1H), 7.98 (d, J=8.4 Hz, 1H), 7.05 (d, J=1.8 Hz, 1H), 3.89 (s, 3H), 2.03 (s, 3H), 1.74 (s, 6H); MS (m/z): 570.2 (M+1)$^+$.

Example 135

N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)-2,4-difluorobenzenesulfonamide Step 1: 2,4-difluoro-N-(2-methoxy-5-(4,4,5,5-tetramethyl-1,3,2-dioxaborolan-2-yl)pyridin-3-yl)benzenesulfonamide To a stirred solution of 5-bromo-2-methoxypyridin-3-amine (1.231 mmol) in pyridine (3 mL) at 0° C., benzene sulfonyl chloride (1.847 mmol) was added drop wise and stirred at RT for 2 h. The reaction mixture was evaporated to dryness. The residue was dissolved in ethyl acetate (100 mL) and partitioned with water. The ethyl acetate layer was separated and dried over sodium sulfate. The organic layer was evaporated to dryness. The compound was used as crude for further step.

Step 2: N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)-2,4-difluorobenzenesulfonamide To the stirred solution N-(8-bromo-1-(4-(2-cyanopropan-2-yl)phenyl)-3-methyl-1H-imidazo[4,5-c]quinolin-2(3H)-ylidene)cyanamide (0.211 mmol) in dry DMF (5 ml) was added 2,4-difluoro-N-(2-methoxy-5-(4,4,5,5-tetramethyl-1,3,2-dioxaborolan-2-yl)pyridin-3-yl)benzenesulfonamide (0.390 mmol) followed by catalyst palladium dichlorobis triphenylphosphine (0.021 mmol). Saturated solution of sodium carbonate (0.780 mmol) was added to it and the resulting solution was heated to 111° C. for 8 minutes in microwave. Solvent was removed and the crude material was extracted in EtOAc, washed with brine several times and dried over anhydrous Na$_2$SO$_4$. The solvent was evaporated and the crude solid was purified (silica gel column, CHCl$_3$/MeOH as eluent) to obtain the title compound.

¹H NMR (300 MHz, DMSO-d₆): δ 10.33 (s, 1H), 9.23 (s, 1H), 8.21 (d, J=9 Hz, 1H), 7.91 (bs, 5H), 7.73 (m, 3H), 7.59 (m, 1H), 7.19 (m, 1H), 6.85 (d, J=1.5 Hz, 1H), 3.92 (s, 3H), 3.60 (s, 3H), 1.81 (s, 6H); MS (m/z): 665 (M+1)⁺.

Example 136

N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-yl)-2-propylpentanamide N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (Example 5, 0.379 mmol) was stirred in valproic anhydride (5 mL). Potassium acetate (0.379 mmol) was added to it and the reaction was carried out at 110-115° C. for 2 h. The reaction mixture was cooled, diluted with water and extracted with ethyl acetate. Organic layer was concentrated, dried using anhydrous sodium sulfate and purified on silica gel column to obtain the title compound. ¹H NMR (300 MHz, DMSO-d₆): δ 10.21 (s, 1H), 9.32 (s, 1H), 9.08 (s, 1H), 8.63 (s, 1H), 8.44 (d, J=5.1 Hz, 1H), 8.28 (d, J=5.1 Hz, 1H), 8.18-8.15 (m, 1H), 8.01 (d, J=5.1 Hz, 1H), 7.06 (s, 1H), 3.94 (s, 3H), 1.77 (s, 3H), 1.56 (m, 2H), 1.35 (s, 6H), 1.23 (s, 1H), 0.91 (s, 6H); MS (m/z): 654.4 (M+1)⁺.

Example 137

Methyl 2-amino-5-(2-(cyanoimino)-1-(6-(2-cyanopropan-2-yl)pyridin-3-yl)-3-methyl-2,3-dihydro-1H-imidazo[4,5-c]quinolin-8-yl)nicotinate 2-(5-(8-bromo-3-(methyl)-2-oxo-2,3-dihydro-1H-imidazo[4,5-c]quinolin-1-yl)pyridin-2-yl)-2-methylpropanenitrile (0.224 mmol) and methyl 2-amino-5-(4,4,5,5-tetramethyl-1,3,2-dioxaborolan-2-yl)nicotinate (0.224 mmol) was stirred in DMF. Dichlorobis(triphenylphosphine)Pd(II) (0.0224 mmol) was added under nitrogen atmosphere. Saturated solution of sodium carbonate (0.560 mmol) was added and reaction mixture was stirred at 110-115° C. for 6 h. The reaction mixture was cooled and extracted with ethyl acetate. Organic layer was filtered, dried over sodium sulfate, concentrated and purified (silica gel column CHCl₃/MeOH as eluent) to obtain the title compound. ¹H NMR (300 MHz, CDCl₃+Drop of TFA): δ 9.04 (s, 1H), 8.76 (d, J=2.1 Hz, 1H), 8.32 (d, J=2.4 Hz, 1H), 8.22 (d, J=9.0 Hz, 1H), 7.99 (dd, J=8.4, 2.4 Hz, 1H), 7.90 (d, J=2.4 Hz, 1H), 7.81 (d, J=8.4 Hz, 1H), 7.68 (dd, J=9.0, 2.1 Hz, 1H), 6.85 (d, J=1.8 Hz, 1H), 3.87 (s, 3H), 3.86 (s, 3H), 1.70 (s, 3H), 1.66 (s, 3H); MS (m/z): 518.2 (M+1)⁺.

Example 138

N-(8-(6-(benzylamino)-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide Sodium hydride (0.521 mmol) was added to a solution of N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (Example 5, 0.474 mmol) in dry THF. The reaction mixture was stirred for 20 minutes, followed by the addition of dibenzylchloro phosphate (0.474 mmol). The reaction mixture was further stirred at RT for 24 h. The crude product was filtered and purified (silica gel column, MeOH/CHCl₃ as eluent) to obtain the title compound. ¹H NMR (300 MHz, DMSO-d₆): δ 9.22 (s, 1H), 9.06 (d, J=2.4 Hz, 1H), 8.41 (dd, J=8.4, 2.4 Hz, 1H), 8.16 (d, J=9.0 Hz, 1H), 8.08 (bs, 1H), 8.01-7.97 (m, 2H), 7.81 (bs, 1H), 7.46 (m, 1H), 7.34-7.21 (m, 5H), 6.86 (d, J=1.8 Hz, 1H), 4.67 (d, 2H), 3.91 (s, 3H), 1.74 (s, 3H), 1.73 (s, 3H); MS (m/z): 618.3 (M+1)⁺.

Pharmacology

The efficacy of the present compounds can be determined by a number of pharmacological assays well known in the art, such as described below. The exemplified pharmacological assays, which follow herein, have been carried out with the compounds of the present invention.

Example 139

Protocol for Kinase Assay (PI3Kα)

p110α Radioactive Lipid Kinase Assay

The assay was designed as in the reference, Journal of Biomolecular Screening, 2002, Vol. 7, No. 5, 441-450, the disclosure of which is incorporated by reference for the teaching of the assay.

The p110α biochemical assay was performed using a radioactive assay measuring the incorporation of $^{32}P$ into the p110α substrate, phosphatidylinositol (PI). For the generation of IC₅₀ curves, the reaction was performed in a 96-well MaxiSorp plates. Plates were pre-coated with 4 μg/well of a 1:1 ratio of phosphatidylinositol (PI: Avanti #840042C) and phosphatidylserine (PS: Avanti #840032C) diluted in CHCl₃. Equal amount of p110α (Upstate Millipore) protein was added to each well, containing reaction buffer (50 mM MOPSO pH7.0, 100 mM NaCl, 4 mM MgCl₂, 0.1% (w/v) BSA) whereas, for negative control, only reaction buffer was added. Test compounds (referred to by example nos. in the following table 1) dissolved in DMSO were treated at nine-point dose responses. Reactions were initiated by the addition of 25 μM ATP solution containing 50 μCi/ml [γ-$^{32}$P]-ATP and incubated at RT for 2 h with gentle shaking. Reactions were finally terminated by the addition of 50 mM EDTA stock solution. Plates were washed 3 times with TBS buffer. The plates were air dried, Microscint 0 (Perkin Elmer) was added to each well and the plates were sealed. The radioactivity incorporated into the immobilized PI substrate was determined with Top Count (Perkin Elmer). Inhibition was calculated using the following equation:

% inhibition=$(D_{cpm}-T_{cpm})/(D_{cpm})\times100$ $T_{cpm}=^{32}$P-cpm in presence of test compounds
$D_{cpm}=^{32}$P-cpm in DMSO control (enzyme control deducted)
Results: IC₅₀ values of test compounds for PI3 kinase activity is indicated in Table 1.

TABLE 1

| Example No. | IC₅₀ in μM | Example No. | IC₅₀ (μM) | Example No. | IC₅₀ in μM |
|---|---|---|---|---|---|
| 5 | ++ | 76 | + | 95 | + |
| 70 | ++ | 77 | + | 121 | + |
| 73 | ++ | 78 | + | 125 | ++ |
| 75 | + | 79 | ++ | | |

| Symbol | IC₅₀ range class |
|---|---|
| ++ | ≤0.01 μM |
| + | >0.01 μM upto 1 μM |

Example 140

Cytotoxicity Assay

Propidium Iodide Assay

The assay was designed as in the reference, Anticancer Drugs, 2002, 13, 1-8, the disclosure of which is incorporated by reference for the teaching of the assay.

Cells from cell lines A2780 (ovarian cell line) and PC3 (prostate cell line) (both from ATCC) were seeded at a density of 3000 cells/well in a white opaque 96-well plate. Following incubation at 37° C./5% $CO_2$ for a period of 18-24 h, the cells were treated with various concentrations (stock solution was prepared in DMSO and subsequent dilutions were made in media as per ATCC guidelines) of the test compounds for a period of 48 h. At the end of treatment, the culture medium was discarded, the cells were washed with 1×PBS and 200 µl of 7 µg/ml propidium iodide was added to each well. The plates were frozen at −70° C. overnight. For analysis, the plates were warmed to RT, allowed to thaw and were read in PoleStar fluorimeter with the fluorescence setting. The percentage of viable cells in the non-treated set of wells was considered to be 100 and the percentage viability following treatment was calculated accordingly. $IC_{50}$ values were calculated from graphs plotted using these percentages. Results for test compounds in individual cell lines are shown in Table 2a.

Results: $IC_{50}$ values for test compounds (referred to by the example numbers) are indicated in Table 2a.

% Inhibition values for test compounds at 1 µM are indicated in Table 2b.

TABLE 2a

| Example No. | Cell Lines ($IC_{50}$ in µM) | |
|---|---|---|
| | A2780 | PC3 |
| 1 | ++ | ++ |
| 2 | ++ | ++ |
| 3 | ++ | ++ |
| 4 | ++ | ++ |
| 5 | ++ | ++ |
| 6 | ++ | ++ |
| 7 | ++ | ++ |
| 9 | ++ | ++ |
| 10 | ++ | ++ |
| 11 | ++ | ++ |
| 12 | ++ | ++ |
| 70 | ++ | ++ |
| 73 | ++ | ++ |
| 75 | ++ | ++ |
| 76 | ++ | + |
| 77 | ++ | ++ |
| 78 | ++ | ++ |
| 79 | ++ | ++ |
| 81 | ++ | ++ |
| 91 | ++ | ++ |
| 92 | ++ | ++ |
| 93 | + | + |
| 94 | ++ | ++ |
| 95 | ++ | ++ |
| 99 | ++ | + |
| 100 | ++ | ++ |
| 101 | ++ | ++ |
| 103 | ++ | ++ |
| 105 | ++ | ++ |
| 106 | ++ | ++ |
| 108 | ++ | + |
| 109 | ++ | + |
| 123 | ++ | ++ |
| 125 | ++ | ++ |
| 126 | ++ | ++ |
| 137 | ++ | ++ |
| 138 | ++ | ++ |

| Symbol | $IC_{50}$ range class |
|---|---|
| ++ | ≤0.5 µM |
| + | >0.5 µM upto 2 µM |

TABLE 2b

| Example No. | Cell Lines (% Inhibition at 1 µM) | |
|---|---|---|
| | A2780 | PC3 |
| 13 | +++ | +++ |
| 14 | +++ | ++ |
| 25 | +++ | ++ |
| 26 | +++ | ++ |
| 27 | + | + |
| 28 | ++ | + |
| 29 | ++ | + |
| 30 | + | + |
| 34 | + | + |
| 35 | +++ | ++ |
| 36 | +++ | +++ |
| 37 | ++ | + |
| 38 | +++ | ++ |
| 39 | ++ | ++ |
| 40 | ++ | + |
| 41 | ++ | ++ |
| 43 | + | + |
| 44 | ++ | + |
| 45 | ++ | + |
| 46 | +++ | ++ |
| 47 | + | + |
| 48 | +++ | ++ |
| 49 | ++ | + |
| 50 | +++ | ++ |
| 51 | +++ | ++ |
| 52 | + | + |
| 53 | ++ | + |
| 54 | ++ | + |
| 55 | +++ | ++ |
| 56 | +++ | ++ |
| 57 | +++ | ++ |
| 62 | ++ | ++ |
| 63 | ++ | + |
| 64 | ++ | + |
| 65 | + | + |
| 66 | +++ | +++ |
| 67 | ++ | ++ |
| 68 | ++ | + |
| 69 | +++ | ++ |
| 71 | + | + |
| 72 | + | + |
| 80 | +++ | ++ |
| 82 | ++ | + |
| 83 | +++ | ++ |
| 84 | +++ | +++ |
| 85 | + | + |
| 86 | +++ | ++ |
| 87 | ++ | + |
| 88 | +++ | ++ |
| 89 | ++ | + |
| 90 | +++ | ++ |
| 97 | +++ | +++ |
| 98 | +++ | +++ |
| 102 | +++ | + |
| 119 | +++ | +++ |
| 121 | + | + |
| 122 | +++ | ++ |
| 124 | +++ | +++ |
| 127 | +++ | ++ |
| 128 | ++ | + |
| 129 | +++ | ++ |
| 131 | ++ | ++ |
| 132 | + | + |

TABLE 2b-continued

| | | |
|---|---|---|
| 135 | +++ | +++ |
| 136 | +++ | ++ |

| Symbol | Inhibition range |
|---|---|
| +++ | ≥70% |
| ++ | ≥30% upto 70% |
| + | <30% |

Representative compounds of the present invention are tested in other cell lines as mentioned in the table below in the same manner as tested in the cell lines A2780 and PC3.

| Type of Cancer | Cell Lines | Type of Cancer | Cell Lines |
|---|---|---|---|
| Breast | MDA MB 231 | Bladder | BXF 1218 |
| | MDA MB 468 | | BXF 1228 |
| | BT 549 | Colon | CXF 1103 |
| | MCF7 | | CXF 1729 |
| Pancreatic | Panc1 | | CXF 1783 |
| | AsPc1 | | CXF 243 |
| | BxPC3 | | CXF 280 |
| Renal | 786-O | | CXF 676 |
| Liver | HuH-7 | | CXF 975 |
| | HEPG2 | Gastric | GXF 1172 |
| Colorectal | HCT116 | | GXF 209 |
| | HCT-15 | | GXF 97 |
| | SW480 | Head and neck | HNXF 536 |
| Lung | H-460 | | HNXF 908 |
| | A-549 | Mesothelioma | PXF 1752 |
| | A431 | | PXF 541 |
| Blood Stem cells | AHS NSB023 | | |
| | AHS NSB024 | | |
| | AHS NSB027 | | |

Example 141

CCK8 Assay Protocol

Cells from the various cell lines (as described in following table) were seeded at a density of 3000 cells/well in a 96 well transparent plate (Nunclon Cat. No. 167008) and after 24 h incubation at 37° C. and 5% $CO_2$, test compounds were added to the wells in different concentrations. Plates were incubated at 37° C. and 5% $CO_2$ for 48 h. Cytotoxicity was assayed by addition of CCK8 reagent (5 μL/well). Plates were further incubated for 2 h to allow for the development of formazan dye and the plates were read in spectramax spectrophotometer (OD at 490 nM). Percent cytotoxicity was calculated with respect to control.

| | |
|---|---|
| Glioblastoma | LN229 |
| | LN18 |
| | U 87 MG |
| | HNGC-2 |
| Chronic Myeloid Leukemia (CML) | K562 |
| | T315I |
| | KU812/SR |
| | KU812 |
| | KCL22/SR |
| | KCL22 |

Results: The test compounds showed $IC_{50} \leq 0.1$ μM

Example 142

Anti-CD3 mAb and Anti-CD28 mAb-Induced Cytokine Production Assay

Preparation of Anti-CD3/Anti-CD28 Coated Plates:

96 well plates were coated with goat anti-mouse IgG, Fc (Millipore) at a concentration of 16.5 μg/ml in coating buffer (8.4 g/ml $NaHCO_3$, 3.56 g $Na_2CO_3$, pH 9.5). Following overnight incubation at 4° C., the plates were washed and then incubated with anti-CD3 (3.5 μg/ml; R&D Systems) and anti-CD28 (35 ng/ml; R&D Systems) cocktail for 3 hours. Subsequently, the plates were washed, and used for hPBMC stimulation.

hPBMC Stimulation:

Peripheral blood was collected from normal healthy volunteers after informed consent. Peripheral blood mononuclear cells (hPBMC) were harvested using Ficoll-Hypaque density gradient centrifugation (1.077 g/ml; Sigma Aldrich). hPBMCs were resuspended in RPMI 1640 culture medium (Gibco BRL, Pasley, UK) containing 10% FCS, 100 U/ml penicillin (Sigma Chemical Co. St Louis, Mo.) and 100 mg/ml streptomycin (Sigma Chemical Co. St Louis, Mo.) at $1.25 \times 10^6$ cells/ml of assay medium. $2.5 \times 10^5$ hPBMCs were added per well of 96-well plate coated with or without anti-CD3/anti-CD28 mAbs. Simultaneously, varying concentrations of test compounds or 0.5% DMSO (vehicle control) were added to appropriate wells. The cells were then incubated for 18 hrs at 37° C., 5% $CO_2$ following which supernatants were collected, stored at −70° C. and assayed later for TNF-α, IL-6 and IL-1β by ELISA (OptiEIA ELISA sets; BD Biosciences). In every experiment, each condition was run in triplicate wells. In all experiments, the toxicity of test compounds was ascertained, in parallel, using the MTS (3-(4,5-dimethylthiazol-2-yl)-5-(3-carboxymethoxyphenyl)-2-(4-sulfonyl)-2H-tetrazolium) assay as described in Am. J. Physiol. Cell Physiol., 2003, 285, C813-C822.

Results: The test compound showed significant inhibition of TNF-α, IL-6 and IL-1β. The $IC_{50}$ values for the test compound for TNF-α, IL-6 and IL-1β inhibition was ≤0.01μM.

Example 143

Angiogenesis Assay

Tube Formation Assay

Human umbilical vein endothelial cells (HUVECs) are grown in endothelial medium (Promocell), supplemented with 20% fetal bovine serum (FBS), 100 units/ml penicillin, 100 μg/ml streptomycin, 3 ng/ml basic fibroblast growth factor, and 5 units/ml heparin at 37° C. under a humidified 95%-5% (v/v) mixture of air and $CO_2$.

For the assay, 250 μl of growth factor-reduced Matrigel (BD Biosciences) is pipetted into a 24 well tissue culture plate and polymerized for 30 min at 37° C. HUVECs incubated in endothelial media containing 1% FBS for 6 h are harvested after trypsin treatment and suspended in endothelial medium containing 1% FBS. Cells are plated onto matrigel layer at a density of $2 \times 10^4$ cells/well. These cells are treated with test compounds for 30 min at RT followed by the addition of 40 ng/ml VEGF. After 18 h, the cultures are photographed and inhibition is recorded.

Example 144

PI3K α, β, γ and δ Isoform Kinase Assays

The assay is performed in 96 well Maxisorp plates (cat no 437796). 50 μl/well of 1:1 mixture of PtdIns and PtdSer dissolved in chloroform is pipetted into 96 well white Maxisorp plates. The solvents are evaporated overnight at RT yielding a lipid precoated plate with 4 μg/well lipid. The reaction is set up by mixing 10 μl/well of assay buffer (40 mM TRIS pH 7.57, 20 mM $MgCl_2$, 0.1 mg/ml BSA). PI3K enzyme isoforms contained in 10 μl of assay buffer at appropriate concentration (β isoform-50 ng/well, γ isoform-150 nM/well and δ isoform-40 ng/well) are added to each well. 1 μL of test compound in DMSO at various concentrations is added to each well followed by addition of 5 μL of ATP (10 μM stock prepared in kinase buffer) to each well. The plate is incubated at RT for 2 h with constant shaking. The reaction is terminated with 25 μl/well of ADP Glo reagent (cat no Promega V9101) for 40 minutes. 50 μl Kinase Detection Buffer (cat no Promega V9101) is added to each well and incubated for 30 minutes. The plate is read for Luminescence on Polar star Luminiscence counter.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A compound of formula (I)

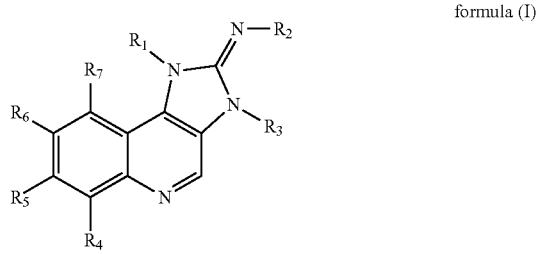

formula (I)

wherein, $R_1$ is $(C_1-C_8)$alkyl, $(C_2-C_8)$alkenyl, $(C_2-C_8)$alkynyl, $(C_3-C_{10})$cycloalkyl, $(C_6-C_{14})$aryl, heterocyclyl, heteroaryl, $(C_1-C_8)$alkyl$(C_6-C_{14})$aryl, $(C_1-C_8)$alkylheteroaryl, $(C_1-C_8)$alkylheterocyclyl, —$CONR_xR_y$ or —$COR_x$, wherein each of $(C_1-C_8)$alkyl, $(C_2-C_8)$alkenyl, $(C_2-C_8)$alkynyl, $(C_3-C_{10})$cycloalkyl, $(C_6-C_{14})$aryl, heterocyclyl, heteroaryl, $(C_1-C_8)$alkylaryl, $(C_1-C_8)$alkylheteroaryl and $(C_1-C_8)$alkylheterocyclyl is optionally substituted with one or more of $R^a$;

$R_2$ is —CN;

$R_3$ is hydrogen, —$COR_x$, —$S(=O)_mR_x$, —$CONR_xR_y$ or $(C_1-C_8)$alkyl, wherein $(C_1-C_8)$alkyl is optionally substituted with one or more groups selected from the group consisting of —CN, —$CONR_xR_y$, —$COR_x$, —$COOR_x$, —$NR_xR_y$ and —$S(=O)_mR_x$;

$R_4$, $R_5$ and $R_7$ are hydrogen;

$R_6$ is hydrogen, halogen, —$NR_xR_y$, —$NR_xCOR_y$, —$OR_x$, —$SR_x$ or $R_1$;

$R^a$ at each occurrence is independently selected from the group consisting of halogen, —CN, —$OR_x$, —$S(=O)_mR_x$, —$NR_xR_y$, —$NR_xCOR_y$, —$N(COR_y)_2$, —$NR_xCOOR_y$, —$NR_xSO_2R_y$, —$COOR_x$, —$(CH_2)_nNR_xCOOR_y$, -oxo-, —$NHCH_2O(CH_2)_2OR_x$, $(C_1-C_8)$alkyl, $(C_6-C_{14})$aryl, and heterocyclyl, wherein heterocyclyl is a monocyclic ring system containing 5 or 6 ring atoms of which one, two or three are heteroatoms selected from N, O and S wherein each of $(C_1-C_8)$alkyl $(C_6-C_{14})$aryl, and heterocyclyl, is optionally substituted with one or more of $R^b$;

wherein $R_x$ and $R_y$ at each occurrence are independently selected from the group consisting of hydrogen, $(C_1-C_8)$alkyl, $(C_6-C_{14})$aryl and $(C_1-C_8)$alkyl$(C_6-C_{14})$aryl, wherein each of $(C_1-C_8)$alkyl, $(C_6-C_{14})$aryl and $(C_1-C_8)$alkyl$(C_6-C_{14})$aryl are optionally substituted with $R^b$;

$R^b$ at each occurrence is independently selected from the group consisting of halogen, nitro, —CN, hydroxy, $(C_1-C_8)$alkoxy, —COOH, —$C(O)O(C_1-C_8)$alkyl, —$NH_2$ and $(C_1-C_8)$alkyl;

m is 0 or an integer from 1 to 2; and n is an integer from 1 to 2; or a pharmaceutically acceptable salt, a stereoisomer, a tautomer or N-oxide thereof.

2. The compound according to claim 1, wherein $R_1$ is $(C_1-C_8)$alkyl, $(C_2-C_8)$alkenyl, $(C_2-C_8)$alkynyl, $(C_3-C_{10})$cycloalkyl, $(C_6-C_{14})$aryl, heterocyclyl, heteroaryl, $(C_1-C_8)$alkyl$(C_6-C_{14})$aryl, $(C_1-C_8)$alkylheteroaryl, $(C_1-C_8)$alkylheterocyclyl, —$CONR_xR_y$ or —$COR_x$, wherein each of $(C_1-C_8)$alkyl, $(C_2-C_8)$alkenyl, $(C_2-C_8)$alkynyl, $(C_3-C_{10})$cycloalkyl, $(C_6-C_{14})$aryl, heterocyclyl, heteroaryl, $(C_1-C_8)$alkyl$(C_6-C_{14})$aryl, $(C_1-C_8)$alkylheteroaryl and $(C_1-C_8)$alkylheterocyclyl is optionally substituted with one or more of $R^a$;

$R_2$ is —CN;

$R_3$ is hydrogen or $(C_1-C_8)$alkyl, wherein $(C_1-C_8)$alkyl is optionally substituted with one or more groups selected from —CN or —$NR_xR_y$;

$R_4$, $R_5$ and $R_7$ are hydrogen;

$R_6$ is hydrogen, halogen, —$NR_xR_y$, —$NR_xCOR_y$, —$OR_x$—$SR_x$ or $R_1$;

$R^a$ at each occurrence is independently selected from the group consisting of halogen, —CN, —$OR_x$, —$S(=O)_m$ $R_x$, —$NR_xR_y$, —$NR_xCOR_y$, —$N(COR_y)_2$, —$NR_xCOOR_y$, —$NR_xSO_2R_y$, —$COOR_x$, —$(CH_2)_nNR_xCOOR_y$, -oxo-, —$NHCH_2O(CH_2)_2OR_x$, $(C_1-C_8)$alkyl, $(C_6-C_{14})$aryl, and heterocyclyl wherein each of $(C_1-C_8)$alkyl, $(C_6-C_{14})$aryl and heterocyclyl is optionally substituted with one or more of $R^b$;

wherein $R_x$ and $R_y$ at each occurrence are independently selected from the group consisting of hydrogen, $(C_1-C_8)$alkyl, $(C_6-C_{14})$aryl and $(C_1-C_8)$alkyl$(C_6-C_{14})$aryl, wherein each of $(C_1-C_8)$alkyl, $(C_6-C_{14})$aryl and $(C_1-C_8)$alkyl$(C_6-C_{14})$aryl is optionally substituted with $R^b$;

$R^b$ at each occurrence is independently selected from the group consisting of halogen, nitro, —CN, hydroxy, $(C_1-C_8)$alkoxy, —COOH, —$C(O)O$ $(C_1-C_8)$alkyl; —$NH_2$ and $(C_1-C_8)$alkyl;

m is 0 or an integer from 1 to 2; and n is an integer from 1 to 2; or a pharmaceutically acceptable salt, a stereoisomer, a tautomer or N-oxide thereof.

3. The compound according to claim 1, wherein $R_1$ is $(C_6-C_{14})$aryl, heterocyclyl, heteroaryl or $(C_1-C_8)$alkylheterocyclyl, wherein each of $(C_6-C_{14})$aryl, heterocyclyl, heteroaryl or $(C_1-C_8)$alkylheterocyclyl is optionally substituted with one or more of $R^a$;

$R_2$ is —CN;

$R_3$ is hydrogen or $(C_1-C_8)$alkyl, wherein $(C_1-C_8)$alkyl is optionally substituted with one or more groups selected from —CN or —$NR_xR_y$;

$R_4$, $R_5$ and $R_7$ are hydrogen;

$R_6$ is hydrogen, halogen, —$NR_xR_y$, —$NR_xCOR_y$, —$OR_x$, —$SR_X$ or $R_1$;

$R^a$ at each occurrence is independently selected from the group consisting of halogen, —CN, —$OR_x$, —$S(=O)_mR_x$, —$NR_xR_y$, —$NR_xCOR_y$, —$N(COR_y)_2$, —$NR_xCOOR_y$, —$NR_xSO_2R_y$, —CO-$OR_x$, —$(CH_2)_nNR_xCOOR_y$, -oxo-, —$NHCH_2O(CH_2)_2OR_x$, $(C_1-C_8)$alkyl, $(C_6-C_{14})$aryl, and heterocyclyl, wherein each of $(C_1-C_8)$alkyl, $(C_6-C_{14})$aryl and heterocyclyl is optionally substituted with one or more of $R_b$;

wherein $R_x$ and $R_y$ at each occurrence are independently selected from the group consisting of hydrogen, $(C_1-C_8)$alkyl, $(C_6-C_{14})$aryl and $(C_1-C_8)$alkyl$(C_6-C_{14})$aryl wherein each of $(C_1-C_8)$alkyl, $(C_6-C_{14})$aryl and $(C_1-C_8)$alkyl$(C_6-C_{14})$aryl is optionally substituted with $R^b$;

$R^b$ at each occurrence is independently selected from the group consisting of halogen, nitro, —CN, hydroxy, $(C_1-C_8)$alkoxy, —COOH, C(O)O—$(C_1-C_8)$alkyl, —$NH_2$ and $(C_1-C_8)$alkyl;

m is 0; and n is an integer from 1 to 2; or a pharmaceutically acceptable salt, a stereoisomer, a tautomer or N-oxide thereof.

4. The compound according to claim 1, wherein $R_1$ is $(C_6-C_{14})$aryl, heterocyclyl, heteroaryl or $(C_1-C_8)$alkylheterocyclyl, wherein each of $(C_6-C_{14})$aryl, heterocyclyl, heteroaryl and $(C_1-C_8)$alkylheterocyclyl is optionally substituted with one or more of $R^a$;

$R_2$ is —CN;

$R_3$ is hydrogen or $(C_1-C_8)$alkyl, wherein $(C_1-C_8)$alkyl is optionally substituted with one or more groups selected from —CN or —$NR_xR_y$;

$R_4$, $R_5$ and $R_7$ are hydrogen;

$R_6$ is $(C_6-C_{14})$aryl, heterocyclyl or heteroaryl, wherein each of $(C_6-C_{14})$aryl, heterocyclyl and heteroaryl is optionally substituted with one or more of $R^a$;

$R^a$ at each occurrence is independently selected from the group consisting of halogen, —CN, —$OR_x$, —$S(=O)_mR_x$, —$NR_xR_y$, —$NR_xCOR_y$, —$N(COR_y)_2$, —$NR_xCOOR_y$, —$NR_xSO_2R_y$, —$(CH_2)_nNR_xCOOR_y$, -oxo-, —$NHCH_2O(CH_2)_2OR_x$, $(C_1-C_8)$alkyl, $(C_6-C_{14})$aryl, and heterocyclyl wherein each of $(C_1-C_8)$alkyl, $(C_6-C_{14})$aryl, and heterocyclyl is optionally substituted with one or more of $R^b$;

wherein $R_x$ and $R_y$ at each occurrence are independently selected from the group consisting of hydrogen, $(C_1-C_8)$alkyl, $(C_6-C_{14})$aryl and $(C_1-C_8)$alkyl$(C_6-C_{14})$aryl, wherein each of $(C_1-C_8)$alkyl, $(C_6-C_{14})$aryl, and $(C_1-C_8)$alkyl$(C_6-C_{14})$aryl is optionally substituted with $R^b$;

$R^b$ at each occurrence is independently selected from the group consisting of halogen, nitro, —CN, hydroxy, $(C_1-C_8)$alkoxy, —COOH, —$C(O)O(C_1-C_8)$alkyl, —$NH_2$ and $(C_1-C_8)$alkyl;

m is 0; and n is an integer from 1 to 2; or a pharmaceutically acceptable salt, a stereoisomer, a tautomer or N-oxide thereof.

5. The compound according to claim 1, wherein $R_1$ is $(C_1-C_8)$alkylheterocyclyl, $(C_6-C_{14})$aryl or heteroaryl, wherein each of $(C_1-C_8)$alkylheterocyclyl, $(C_6-C_{14})$aryl and heteroaryl is optionally substituted with one or more of $R^a$, wherein $R^a$ at each occurrence is independently selected from the group consisting of halogen, —CN, —$OR_x$, —$S(=O)_mR_x$, —$NR_xR_y$, —$NR_xCOR_y$, —$NR_xSO_2R_y$, —$COOR_x$, $(C_1-C_8)$alkyl, $(C_6-C_{14})$ and heterocyclyl wherein each of $(C_1-C_8)$alkyl, $(C_6-C_{14})$aryl and heterocyclyl is optionally substituted with one or more of $R^b$;

wherein $R_x$ and $R_y$ at each occurrence are independently selected from the group consisting of hydrogen, $(C_1-C_8)$alkyl and $(C_6-C_{14})$aryl wherein each of $(C_1-C_8)$alkyl and $(C_6-C_{14})$aryl is optionally substituted with $R^b$;

$R^b$ at each occurrence is independently selected from the group consisting of halogen, nitro, —CN, hydroxy, $(C_1-C_8)$alkoxy, —COOH, —$C(O)O(C_1-C_8)$ alkyl, —$NH_2$ and $(C_1-C_8)$alkyl;

m is 0; and n is an integer from 1 to 2; or a pharmaceutically acceptable salt, a stereoisomer, a tautomer or N-oxide thereof.

6. The compound according to claim 5, wherein $R_1$ is phenyl, pyridyl, quinolinyl or 2-morpholinoethyl, wherein each of phenyl, pyridyl, quinolinyl and 2-morpholinoethyl is optionally substituted with one or more of $R^a$, wherein $R^a$ at each occurrence is independently selected from the group consisting of halogen, —CN, $OR_x$, —$S(=O)_mR_x$, —$NR_xR_y$, —$NR_xCOR_y$, —$NR_xSO_2R_y$, —$COOR_x$,$(C_1-C_8)$alkyl, $(C_6-C_{14})$ aryl and heterocyclyl wherein each of $(C_1-C_8)$alkyl, $(C_6-C_{14})$aryl and heterocyclyl is optionally substituted with one or more of $R^b$;

wherein $R_x$ and $R_y$ at each occurrence are independently selected from the group consisting of hydrogen, $(C_1-C_8)$ alkyl and $(C_6-C_{14})$aryl wherein each of $(C_1-C_8)$alkyl and $(C_6-C_{14})$aryl is optionally substituted with $R^b$;

$R^b$ at each occurrence is independently selected from the group consisting of halogen, nitro, —CN, hydroxy, $(C_1-C_8)$alkoxy, —COON, —$C(O)O(C_1-C_8)$alkyl, —$NH_2$ and $(C_1-C_8)$alkyl;

m is 0; and n is an integer from 1 to 2; or a pharmaceutically acceptable salt, a stereoisomer, a tautomer or N-oxide thereof.

7. The compound according to claim 6, wherein $R_1$ is phenyl, pyridyl, quinolinyl or 2-morpholinoethyl, wherein each of phenyl, pyridyl, quinolinyl and 2-morpholinoethyl is optionally substituted with one or more groups selected from the group consisting of halogen, —CN, —$OR_x$, $(C_6-C_{14})$aryl or $(C_1-C_8)$alkyl optionally substituted with —CN or halogen, wherein $R_x$ is $(C_1-C_8)$alkyl or $(C_1-C_8)$alkyl substituted with one or more halogens; or a pharmaceutically acceptable salt, a stereoisomer, a tautomer or N-oxide thereof.

8. The compound according to claim 1, wherein $R_3$ is $C_{1-6}$ alkyl optionally substituted with —CN, or a pharmaceutically acceptable salt, a stereoisomer, a tautomer or N-oxide thereof.

9. The compound according to claim 1, wherein $R_6$ is $(C_6-C_{14})$aryl, heterocyclyl or heteroaryl, wherein each of $(C_6-C_{14})$aryl, heterocyclyl and heteroaryl are optionally substituted with one or more of $R^a$, wherein $R^a$ at each occurrence is independently selected from the group consisting of halogen, —CN, —$OR_x$—$S(=O)_mR_x$, —$NR_xR_y$—$NR_xCOR_y$, —$N(COR_y)_2$, —$NR_xCOOR_y$, —$NR_x$, $SO_2R_y$, —CO-$OR_x$, —$(CH_2)_nNR_xCOOR_y$, -oxo-, —$NHCH_2O(CH_2)_2OR_x$, $(C_1-C_8)$alkyl, $(C_6-C_{14})$aryl, and heterocyclyl wherein each of $(C_1-C_8)$alkyl, $(C_6-C_{14})$aryl, and heterocyclyl is optionally substituted with one or more of $R^b$;

wherein $R_x$ and $R_y$ at each occurrence are independently selected from the group consisting of hydrogen, $(C_1-C_8)$ alkyl, $(C_6-C_{14})$aryl and $(C_1-C_8)$alkyl$(C_6-C_{14})$aryl wherein each of $(C_1-C_8)$alkyl, $(C_6-C_{14})$aryl, and $(C_1-C_8)$alkyl$(C_6-C_{14})$aryl is optionally substituted with $R^b$;

R$^b$ at each occurrence is independently selected from the group consisting of halogen, nitro, —CN, hydroxy, C$_1$-C$_8$ alkoxy, —COON, —C(O)O C$_1$-C$_8$ alkyl, —NH$_2$ and C$_1$-C$_8$ alkyl;
m is 0; and
n is an integer from 1 to 2; or
a pharmaceutically acceptable salt, a stereoisomer, a tautomer or N-oxide thereof.

10. The compound according to claim 9, wherein R$_6$ is phenyl, naphthyl, pyridyl, pyrimidinyl, quinolinyl, benzodioxolyl, pyrrolopyridyl, dihydropyridyl, tetrahydropyrimidyl, indolyl or indazolyl, wherein each of phenyl, naphthyl, pyridyl, pyrimidinyl, quinolinyl, benzodioxolyl, pyrrolopyridyl, dihydropyridyl, tetrahydropyrimidyl, indolyl and indazolyl are optionally substituted with one or more of R$^a$, wherein R$^a$ at each occurrence is independently selected from the group consisting of halogen, —CN, —OR$_x$, —S(=O)$_m$R$_x$, —NR$_x$R$_y$, —NR$_x$COR$_y$, —N(COR$_y$)$_2$, —NR$_x$COOR$_y$, —NR$_x$SO$_2$R$_y$, —COOR$_x$, (CH$_2$)$_n$NR$_x$COOR$_y$, -oxo-, —NHCH$_2$O(CH$_2$)$_2$OR$_x$, (C$_1$-C$_8$)alkyl, (C$_6$-C$_{14}$)aryl, and heterocyclyl wherein each of (C$_1$-C$_8$)alkyl, and heterocyclyl is optionally substituted with one or more of R$^b$;
wherein R$_x$ and R$_y$ at each occurrence are independently selected from the group consisting of hydrogen, (C$_1$-C$_8$) alkyl, (C$_6$-C$_{14}$)aryl, and (C$_1$-C$_8$)alkyl(C$_6$-C$_{14}$)aryl, wherein each of (C$_1$-C$_8$)alkyl, (C$_6$-C$_{14}$)aryl, and (C$_1$-C$_8$) alkyl(C$_6$-C$_{14}$)aryl is optionally substituted with R$^b$;
R$^b$ at each occurrence is independently selected from the group consisting of halogen, nitro, —CN, hydroxy, (C$_1$-C$_8$)alkoxy, —COON, —C(O)O C$_1$-C$_8$ alkyl, —NH$_2$ and (C$_1$-C$_8$)alkyl;
m is 0; and
n is an integer from 1 to 2; or
a pharmaceutically acceptable salt, a stereoisomer, a tautomer or N-oxide thereof.

11. The compound according to claim 10, wherein R$_6$ is phenyl, naphthyl, pyridyl, pyrimidinyl, quinolinyl, benzodioxolyl, pyrrolopyridyl, dihydropyridyl, tetrahydropyrimidyl, indolyl or indazolyl, wherein phenyl, naphthyl, pyridyl, pyrimidinyl, quinolinyl, benzodioxolyl, pyrrolopyridyl, dihydropyridyl, tetrahydropyrimidyl, indolyl and indazolyl are optionally substituted with one or more groups independently selected from the group consisting of —NR$_x$R$_y$, —NR$_x$COOR$_y$, —NR$_x$SO$_2$R$_y$, —NR$_x$COR$_y$, —COOR$_x$, (CH$_2$)$_n$NR$_x$COOR$_y$, =N(COR$_y$)$_2$, —NHCH$_2$O(CH$_2$)$_2$OR$_x$, -oxo-, —CN, —S(=O)$_m$R$_x$, halogen and (C$_1$-C$_8$)alkyl, wherein (C$_1$-C$_8$)alkyl is optionally substituted with halogen, or heterocyclyl, wherein the heterocyclyl is optionally substituted with —C(O)O—C$_1$-C$_8$ alkyl;
wherein R$_x$ and R$_y$ are independently selected from the group consisting of hydrogen, (C$_1$-C$_8$) alkyl, (C$_6$-C$_{14}$)aryl and alkyl (C$_6$-C$_{14}$)aryl, wherein m is 0 and n is 1; or a pharmaceutically acceptable salt, a stereoisomer, a tautomer or N-oxide thereof.

12. The compound according to claim 1, selected from:
N-(8-(6-amino-5-(trifluoromethyl)pyridin-3 -yl)-1 -(6-methoxypyridin-3-yl)-3-methyl- 1 H-imidazo[4,5-c]quinolin-2(3H)-ylidene)cyanamide,
N-(8-(6-(dimethylamino)pyridin-3 -yl)- 1 -(6-methoxypyridin-3 -yl)-3 -methyl-1 H-imidazo [4,5 -c]quinolin-2 (3H)-ylidene)cyanamide,
N-(1 -(6-methoxypyridin-3-yl)-3-methyl-8-(quinolin-3-yl)- 1 H-imidazo[4,5-c]quinolin-2(3H)-ylidene)cyanamide,
N-(8-(6-amino-5-(trifluoromethy)pyridin-3 -yl)-1 -(2-chloro-6-methoxypyridin-3 -yl)-3 -methyl-1 H-imidazo [4,5-c]quinolin-2(3H)-ylidene)cyanamide,
N-(8-(6-amino-5-(trifluoromethyl)pyridin-3-yl)- 1 -(6-(2-cyanopropan-2-yl)pyridin-3 -yl)-3 -methyl-1 H-imidazo [4,5 -c]quinolin-2(3 H)-ylidene)cyanamide,
N-(8-(6-amino-5-(trifluoromethyl)pyridin-3 -yl)-1 -(4-(2-cyanopropan-2-yl)phenyl)-3 -methyl-1 H-imidazo[4,5-c]quinolin-2(3H)-ylidene)cyanamide,
N-(1 -(4-(2-cyanopropan-2-yl)phenyl)-3 -methyl-8-(quinolin-3-yl)- 1 H-imidazo [4,5-c]quinolin-2(3 H)-ylidene)cyanamide,
N-(8-(6-amino-5-(trifluoromethyl)pyridin-3 -yl)-3-methyl- 1 -(2-morpholinoethyl)- 1 H-imidazo[4,5-c]quinolin-2(3H)-ylidene)cyanamide,
N-(8-(6-amino-5-(trifluoromethyl)pyridin-3 -yl)-1 -(6-methoxy-2-methylpyridin-3-yl)-3-methyl-1 H-imidazo [4,5-c]quinolin-2(3H)-ylidene)cyanamide,
N-(8-(6-amino-5-(trifluoromethyl)pyridin-3-yl)- 1 -(6-cyanopyridin-3-yl)-3 -methyl-1 H-imidazo[4,5-c]quinolin-2(3H)-ylidene)cyanamide,
N-(8-(6-amino-5-(trifluoromethyl)pyridin-3 -yl)-3-methyl- 1 -(quinolin-6-yl)- 1 H-imidazo [4,5-c]quinolin-2 (3H)-ylidene)cyanamide,
N-(1 -(4-(2-cyanopropan-2-yl)phenyl)-3 -methyl-8-(6-(methylamino)-5 -(trifluoromethyl)pyridin-3-yl)- 1 H-imidazo[4,5-c]quinolin-2(3H)-ylidene)cyanamide,
N-(8-(5-amino-6-methoxypyridin-3 -yl)-1 -(2,4-dimethoxyphenyl)-3-methyl- 1 H-imidazo [4,5-c] quinolin-2(3 H)-ylidene)cyanamide,
N-(1 -(6-methoxypyridin-3-yl)-3-methyl-8-(pyridin-4-yl)- 1 H-imidazo[4,5-c]quinolin-2(3H)-ylidene)cyanamide,
N-(8-(2-fluoro-5 -(trifluoromethyl)phenyl)- 1 -(6-methoxypyridin-3-yl)-3-methyl- 1 H-imidazo [4,5-c]quinolin-2(3 H)-ylidene)cyanamide,
N-(8-(3,5-difluorophenyl)- 1 -(6-methoxypyridin-3-yl)-3 -methyl-1 H-imidazo [4,5-c]quinolin-2(3 H)-ylidene) cyanamide,
N-(8-(Benzo[d] [1,3]dioxo1-5-yl)- 1 -(6-methoxypyridin-3-yl)-3-methyl- 1 H-imidazo [4,5-c]quinolin-2(3H)-ylidene)cyanamide,
N-(1 -(6-methoxypyridin-3-yl)-3 -methyl-8-(3,4,5-trimethoxyphenyl)- 1 H-imidazo [4,5-c]quinolin-2(3H)-ylidene)cyanamide,
N-(1 -(6-methoxypyridin-3 -yl)-3 -methyl-8-(naphthalen-2-yl) -1 H-imidazo [4,5-c]quinolin-2(3H)-ylidene)cyanamide,
N-(1 -(6-methoxypyridin-3-yl)-8-(2-methoxypyrimidin-5-yl)-3-methyl- 1 H-imidazo [4,5-c]quinolin-2(3 H)-ylidene)cyanamide,
N-(8-(2,4-dimethoxypyrimidin-5-yl)- 1 -(6-methoxypyridin-3 -yl)-3-methyl- 1 H-imidazo [4,5-c]quinolin-2 (3H)-ylidene)cyanamide,
N-(8-(2-fluoropyridin-3 -yl)- 1 -(6-methoxypyridin-3 -yl)-3-methyl- 1 H-imidazo[4,5-c]quinolin-2(3 H)-ylidene) cyanamide,
N-(8-(2,6-difluoropyridin-3-yl)- 1 -(6-methoxypyridin-3-yl)-3 -methyl-1 H-imidazo[4,5-c]quinolin-2(3 H)-ylidene)cyanamide,
N-(1 -(6-methoxypyridin-3-yl)-3 -methyl-8-phenyl- 1 H-imidazo [4,5-c]quinolin-2(3H)-ylidene)cyanamide,
N-(1 -(6-methoxypyridin-3-yl)-3-methyl-8-(5-(trifluoromethyl) pyridin -3-yl)-1 H-imidazo [4,5-c]quinolin-2(3 H)-ylidene)cyanamide,
N-(1 -(6-methoxypyridin-3 -yl)-3-methyl-8-(quinolin-7-yl)- 1 H-imidazo[4,5-c]quinolin-2(3H)-ylidene)cyanamide, N-(8-(2-isopropoxyphenyl)-1-(6-methoxypyridin-3-yl)-3-methyl-1H-imidazo[4,5-c]quinolin-2(3H)-ylidene)cyanamide, N-(8-(3-chlorophenyl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-m-tolyl-1H-imidazo[4,5-c]quinolin-2(3H)-ylidene)cyanamide, N-(8-(4-cyanophenyl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-(4-phenoxyphenyl)-1H-imidazo[4,5-c]quinolin-2(3H)-ylidene)cyanamide, N-(8-(2-chlorophenyl)-1-(6-methoxypyridin-3-yl)-3-methyl-1H-imidazo[4,5-c]quinolin-2(3H)-ylidene)cyanamide, N-(8-(3-methoxyphenyl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-o-tolyl-1H-imidazo[4,5-c]quinolin-2(3H)-ylidene)cyanamide, N-(8-(isoquinolin-4-yl)-1-(6-methoxypyridin-3-yl)-3-methyl-1H-imidazo[4,5-c]quinolin-2(3H)-ylidene)cyanamide, N-(8-(3,4-dimethoxyphenyl)-1-(6-methoxypyridin-3-yl)-3-methyl-1H-imidazo[4,5-c]quinolin-2(3H)-ylidene)cyanamide, N-(8-(4-(isopropylthio)phenyl)-1-(6-methoxypyridin-3-yl)-3-methyl-1H-imidazo[4,5-c]quinolin-2(3H)-ylidene)cyanamide, N-(8-(3-hydroxyphenyl)-1-(6-methoxypyridin-3-yl)-3-methyl-1H-imidazo[4,5-c]quinolin-2(3H)-ylidene)cyanamide, N-(8-(4-fluoropyridin-3-yl)-1-(6-methoxypyridin-3-yl)-3-methyl-1H-imidazo[4,5-c]quinolin-2(3H)-ylidene)cyanamide, N-(8-(3-fluorophenyl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-(3-(trifluoromethyl)phenyl)-1H-imidazo[4,5-c]quinolin-2(3H)-ylidene)cyanamide, N-(8-(2,6-dimethylphenyl)-1-(6-methoxypyridin-3-yl)-3-methyl-1H-imidazo[4,5-c]quinolin-2(3H)-ylidene)cyanamide, N-(1-(6-methoxypyridin-3-yl)-3-methyl-8-(4-(trifluoromethyl)phenyl)-1H-imidazo[4,5-c]quinolin-2(3H)-ylidene)cyanamide, N-(1-(6-methoxypyridin-3-yl)-3-methyl-8-p-tolyl-1H-imidazo[4,5-c]quinolin-2(3H)-ylidene)cyanamide, N-(1-(6-methoxypyridin-3-yl)-3-methyl-8-(2-methylpyridin-3-yl)-1H-imidazo[4,5-c]quinolin-2(3H)-ylidene)cyanamide, N-(8-(4-hydroxyphenyl)-1-(6-methoxypyridin-3-yl)-3-methyl-1H-imidazo[4,5-c]quinolin-2(3H)-ylidene)cyanamide, N-(8-(5-fluoro-2-methoxyphenyl)-1-(6-methoxypyridin-3-yl)-3-methyl-1H-imidazo[4,5-c]quinolin-2(3H)-ylidene)cyanamide, N-(1,8-bis(6-methoxypyridin-3-yl)-3-methyl-1H-imidazo[4,5-c]quinolin-2(3H)-ylidene)cyanamide, N-(8-(2-methoxyphenyl)-1-(6-methoxypyridin-3-yl)-3-methyl-1H-imidazo[4,5-c]quinolin-2(3H)-ylidene)cyanamide, N-(1-(6-(2-cyanopropan-2-yl)pyridin-3-yl)-8-(4-hydroxyphenyl)-3-methyl-1H-imidazo[4,5-c]quinolin-2(3H)-ylidene)cyanamide, N-(1-(6-(2-cyanopropan-2-yl)pyridin-3-yl)-8-(6-methoxypyridin-3-yl)-3-methyl-1H-imidazo[4,5-c]quinolin-2(3H)-ylidene)cyanamide, N-(1-(6-(2-cyanopropan-2-yl)pyridin-3-yl)-8-(5-fluoro-2-methoxyphenyl)-3-methyl-1H-imidazo[4,5-c]quinolin-2(3H)-ylidene)cyanamide, N-(1-(6-(2-cyanopropan-2-yl)pyridin-3-yl)-8-(2-methoxyphenyl)-3-methyl-1H-imidazo[4,5-c]quinolin-2(3H)-ylidene)cyanamide, N-(8-(benzo[d][1,3]dioxol-5-yl)-1-(6-(2-cyanopropan-2-yl)pyridin-3-yl)-3-methyl-1H-imidazo[4,5-c]quinolin-2(3H)-ylidene)cyanamide, N-(1-(6-(2-cyanopropan-2-yl)pyridin-3-yl)-8-(2,4-dimethoxypyrimidin-5-yl)-3-methyl-1H-imidazo[4,5-c]quinolin-2(3H)-ylidene)cyanamide, N-(1-(6-(2-cyanopropan-2-yl)pyridin-3-yl)-3-methyl-8-(quinolin-6-yl)-1H-imidazo[4,5-c]quinolin-2(3H)-ylidene)cyanamide, N-(1-(6-(2-cyanopropan-2-yl)pyridin-3-yl)-3-methyl-8-(3,4,5-trimethoxyphenyl)-1H-imidazo[4,5-c]quinolin-2(3H)-ylidene)cyanamide, N-(8-(benzo[d][1,3]dioxol-5-yl)-1-(6-methoxy-2-methylpyridin-3-yl)-3-methyl-1H-imidazo[4,5-c]quinolin-2(3H)-ylidene)cyanamide, N-(1-(6-methoxy-2-methylpyridin-3-yl)-3-methyl-8-(3-trimethoxyphenyl)-1H-imidazo[4,5-c]quinolin-2(3H)-ylidene)cyanamide, N-(1-(6-(2-cyanopropan-2-yl)pyridin-3-yl)-3-methyl-8-(1H-pyrrolo[2,3-b]pyridin-5-yl)-1H-imidazo[4,5-c]quinolin-2(3H)-ylidene)cyanamide, N-(8-(6-aminopyridin-3-yl)-1-(6-(2-cyanopropan-2-yl)pyridin-3-yl)-3-methyl-1H-imidazo[4,5-c]quinolin-2(3H)-ylidene)cyanamide, N-(1-(6-(2-cyanopropan-2-yl)pyridin-3-yl)-3-methyl-8-(naphthalen-2-yl)-1H-imidazo[4,5-c]quinolin-2(3H)-ylidene)cyanamide, N-(1-(6-(2-cyanopropan-2-yl)pyridin-3-yl)-8-(3,5-difluorophenyl)-3-methyl-1H-imidazo[4,5-c]quinolin-2(3H)-ylidene)cyanamide, N-(1-(6-(2-cyanopropan-2-yl)pyridin-3-yl)-3-methyl-8-(2-fluoropyridin-3-yl)-1H-imidazo[4,5-c]quinolin-2(3H)-ylidene)cyanamide, N-(1-(6-(2-cyanopropan-2-yl)pyridin-3-yl)-8-(2-isopropoxyphenyl)-3-methyl-1H-imidazo[4,5-c]quinolin-2(3H)-ylidene)cyanamide, N-(1-(6-(2-cyanopropan-2-yl)pyridin-3-yl)-8-(3,4-dimethoxyphenyl)-3-methyl-1H-imidazo[4,5-c]quinolin-2(3H)-ylidene)cyanamide, N-(1-(6-(2-cyanopropan-2-yl)pyridin-3-yl)-3-methyl-8-p-tolyl-1H-imidazo[4,5-c]quinolin-2(3H)-ylidene)cyanamide, N-(1-(6-(2-cyanopropan-2-yl)pyridin-3-yl)-3-methyl-8-(4-(trifluoromethyl)phenyl)-1H-imidazo[4,5-c]quinolin-2(3H)-ylidene)cyanamide, N-(1-(6-(2-cyanopropan-2-yl)pyridin-3-yl)-3-methyl-8-(3-(trifluoromethyl)phenyl)-1H-imidazo[4,5-c]quinolin-2(3H)-ylidene)cyanamide, N-(1-(6-(2-cyanopropan-2-yl)pyridin-3-yl)-3-methyl-8-(5-(trifluoromethyl)pyridin-3-yl)-1H-imidazo[4,5-c]quinolin-2(3H)-ylidene)cyanamide, tert-butyl (5-(2-(cyanoimino)-1-(6-(2-cyanopropan-2-yl)pyridin-3-yl)-3-methyl-2,3-dihydro-1H-imidazo[4,5-c]quinolin-8-yl)pyridin-3-yl)methylcarbamate, tert-butyl 4-(5-(2-(cyanoimino)-1-(6-(2-cyanopropan-2-yl)pyridin-3-yl)-3-methyl-2,3-dihydro-1H-imidazo[4,5-c]quinolin-8-yl)pyridin-2-yl)piperazine-1-carboxylate, N-(1-(6-(2-cyanopropan-2-yl)pyridin-3-yl)-8-(1H-indol-5-yl)-3-methyl-1H-imidazo[4,5-c]quinolin-2(3H)-ylidene)cyanamide, N-(8-(5-chloro-6-methoxypyridin-3-yl)-1-(6-(2-cyanopropan-2-yl)pyridin-3-yl)-3-methyl-1H-imidazo[4,5-c]quinolin-2(3H)-ylidene)cyanamide, N-(8-(2-aminopyrimidin-5-yl)-1-(6-(2-cyanopropan-2-yl)pyridin-3-yl)-3-methyl-1H-imidazo[4,5-c]quinolin-2(3H)-ylidene)cyanamide, N-(1-(6-(2-cyanopropan-2-yl)pyridin-3-yl)-3-methyl-8-(6-(piperidin-1-yl)pyridin-3-yl)-1H-imidazo[4,5-c]quinolin-2(3H)-ylidene)cyanamide, N-(1-(6-(2-cyanopropan-2-yppyridin-3-yl)-8-(1H-indazol-6-yl)-3-methyl-1H-imidazo[4,5-c]quinolin-2(3H)-ylidene)cyanamide, N-(1-(6-(2-cyanopropan-2-yl)pyridin-3-yl)-8-(6-fluoro-5-methylpyridin-3-yl)-3-methyl-1H-imidazo[4,5-c]quinolin-2(3H)-ylidene)cyanamide, N-(1-(6-(2-cyanopropan-2-yl)pyridin-3-yl)-8-(1H-indol-6-yl)-3-methyl-1H-imidazo[4,5-c]quinolin-2(3H)-ylidene)cyanamide, N-(1-(6-(2-cyanopropan-2-yl)pyridin-3-yl)-8-(4-fluorophenyl)-3-methyl-1H-imidazo[4,5-c]quinolin-2(3H)-ylidene)cyanamide, N-(1-(6-(2-cyanopropan-2-yl)pyridin-3-yl)-3-methyl-8-(pyridin-4-yl)-1H-imidazo[4,5-c]quinolin-2(3H)-ylidene)cyanamide, N-(1-(6-(2-cyanopropan-2-yl)pyridin-3-yl)-3-methyl-8-(naphthalen-1-yl)-1H-imidazo[4,5-c]quinolin-2(3H)-ylidene)cyanamide, N-(8-(6-amino-5-(trifluoromethyl)pyridin-3-yl)-1-(4-(2-cyanopropan-2-yl)phenyl)-1H-imidazo[4,5-c]quinolin-2(3H)-ylidene)cyanamide, N-(8-(5-amino-6-methoxypyridin-3-yl)-1-(4-(2-cyanopropan-2-yl)phenyl)-3-methyl-1H-imidazo[4,5-c]quinolin-2(3H)-ylidene)cyanamide, N-(1-(4-(2-cyanopropan-2-yl)phenyl)-8-(pyridin-3-yl)-1H-imidazo[4,5-c]quinolin-2(3H)-ylidene)cyanamide, N-(1-(4-(2-cyanopropan-2-yl)phenyl)-3-ethyl-8-(pyridin-3-yl)-1H-imidazo[4,5-c]quinolin-2(3H)-ylidene)cyanamide, N-(1-(4-(2-cyanopropan-2-yephenyl)-8-(2-fluoro-5-(trifluoromethyl)phenyl)-3-methyl-1H-imidazo[4,5-c]quinolin-2(3H)-ylidene)cyanamide, N-(1-(4-(2-cyanopropan-2-yl)phenyl)-3-methyl-8-(3,4,5-trimethoxyphenyl)-1H-imidazo[4,5-c]quinolin-2(3H)-ylidene)cyanamide, tert-butyl 4-(2-(cyanoimino)-1-(4-(2-cyanopropan-2-yl)phenyl)-3-methyl-2,3-dihydro-1H-imidazo[4,5-c]quinolin-8-yl)-5,6-dihydropyridine-1(2H)-carboxylate, N-(1-(4-(2-cyanopropan-2-yl)phenyl)-3-methyl-8-(6-morpholinopyridin-3-yl)-1H-imidazo[4,5-c]quinolin-2(3H)-ylidene)cyanamide, N-(1-(4-(2-cyanopropan-2-yl)phenyl)-8-(6-methoxypyridin-3-yl)-3-methyl-1H-imidazo[4,5-c]quinolin-2(3H)-ylidene)cyanamide, N-(8-(6-amino-5-(trifluoromethyl)pyridin-3-yl)-3-methyl-1-(5-phenylpyridin-3-yl)-1H-imidazo[4,5-c]quinolin-2(3H)-ylidene)cyanamide, N-(8-(5-amino-6-methoxypyridin-3-yl)-3-methyl-1-(5-phenylpyridin-3-yl)-1H-imidazo[4,5-c]quinolin-2(3H)-ylidene)cyanamide, N-(1-(4-(2-cyanopropan-2-yl)phenyl)-8-(1H-indol-6-yl)-3-methyl-1H-imidazo[4,5-c]quinolin-2(3H)-ylidene)cyanamide, N-(8-(5-amino-6-methoxypyridin-3-yl)-1-(6-(2-cyanopropan-2-yl)pyridin-3-yl)-3-methyl-1H-imidazo[4,5-c]quinolin-2(3H)-ylidene)cyanamide, N-(8-(6-amino-5-(trifluoromethyl)pyridin-3-yl)-1-(6-(2-cyanopropan-2-yl)pyridin-3-yl)-1H-imidazo[4,5-c]quinolin-2(3H)-ylidene)cyanamide, N-(8-(6-amino-5-(trifluoromethyl)pyridin-3-yl)-1-(3,5-dimethoxyphenyl)-3-methyl-1H-imidazo[4,5-c]quinolin-2(3H)-ylidene)cyanamide, N-(8-(6-amino-5-(trifluoromethyl)pyridin-3-yl)-1-(2,6-dimethoxypyridin-3-yl)-3-methyl-1H-imidazo[4,5-c]quinolin-2(3H)-ylidene)cyanamide, N-(8-(5-amino-6-methoxypyridin-3-yl)-1-(3,5-dimethoxyphenyl)-3-methyl-1H-imidazo[4,5-c]quinolin-2(3H)-ylidene)cyanamide, N-(1-(2,4-dimethoxyphenyl)-3-methyl-8-(quinolin-3-yl)-1H-imidazo[4,5-c]quinolin-2(3H)-ylidene)cyanamide, N-(1-(2,4-dimethoxyphenyl)-3-methyl-8-(pyridin-3-yl)-1H-imidazo[4,5-c]quinolin-2(3H)-ylidene)cyanamide, N-(1-(3,5-dimethoxyphenyl)-3-methyl-8-(pyridin-3-yl)-1H-imidazo[4,5-c]quinolin-2(3H)-ylidene)cyanamide, N-(1-(2,4-dimethoxyphenyl)-3-methyl-8-(quinolin-6-yl)-1H-imidazo[4,5-c]quinolin-2(3H)-ylidene)cyanamide, N-(1-(2,4-dimethoxyphenyl)-3-methyl-8-(4-(trifluoromethyl)phenyl)-1H-imidazo[4,5-c]quinolin-2(3H)-ylidene)cyanamide, N-(8-(6-amino-5-(trifluoromethyl)pyridin-3-yl)-3-methyl-1-(4-(trifluoromethoxy)phenyl)-1H-imidazo[4,5-c]quinolin-2(3H)-ylidene)cyanamide, N-(8-(5-amino-6-methoxypyridin-3-yl)-3-methyl-1-(4-(trifluoromethoxy)phenyl)-1H-imidazo[4,5-c]quinolin-2(3H)-ylidene)cyanamide, N-(3-methyl-8-(quinolin-3-yl)-1-(4-(trifluoromethoxy)phenyl)-1H-imidazo[4,5-c]quinolin-2(3H)-ylidene)cyanamide, N-(3-methyl-8-(pyridin-3-yl)-1-(4-(trifluoromethoxy)phenyl)-1H-imidazo[4,5-c]quinolin-2(3H)-ylidene)cyanamide, N-(3-methyl-8-(pyridin-4-yl)-1-(4-(trifluoromethoxy)phenyl)-1H-imidazo[4,5-c]quinolin-2(3H)-ylidene)cyanamide, N-(8-(6-amino-5-(trifluoromethyl)pyridin-3-yl)-3-(cyanomethyl)-1-(6-(2-cyanopropan-2-yl)pyridin-3-yl)-1H-imidazo[4,5-c]quinolin-2(3H)-ylidene)cyanamide, N-(8-(6-amino-5-(trifluoromethyl)pyridin-3-yl)-3-methyl-1-(6-(trifluoromethyl)pyridin-3-yl)-1H-imidazo[4,5-c]quinolin-2(3H)-ylidene)cyanamide, N-(3-methyl-8-(6-morpholinopyridin-3-yl)-1-(6-(trifluoromethyl)pyridin-3-yl)-1H-imidazo[4,5-c]quinolin-2(3H)-ylidene)cyanamide, N-(8-(6-methoxypyridin-3-yl)-3-methyl-1-(6-(trifluoromethyl)pyridin-3-yl)-1H-imidazo[4,5-c]quinolin-2(3H)-ylidene)cyanamide, N-(8-(1H-indol-5-yl)-3-methyl-1-(6-(trifluoromethyl)pyridin-3-yl)-1H-imidazo[4,5-c]quinolin-2(3H)-ylidene)cyanamide, N-(1-(6-(2-cyanopropan-2-yepyridin-3-yl)-8-(4-(isopropylthio)phenyl)-3-methyl-1H-imidazo[4,5-c]quinolin-2(3H)-ylidene)cyanamide, N-(8-(4-(butylthio)phenyl)-1-(6-(2-cyanopropan-2-yl)pyridin-3-yl)-3-methyl-1H-imidazo[4,5-c]quinolin-2(3H)-ylidene)cyanamide, tert-butyl 4-(2-(cyanoimino)-1-(6-(2-cyanopropan-2-yl)pyridin-3-yl)-3-methyl-2,3-dihydro-1H-imidazo[4,5-c]quinolin-8-yl)-5,6-dihydropyridine-1(2H)-carboxylate, tert-butyl 4-(2-(cyanoimino)-3-methyl-1-(6-(trifluoromethyl)pyridin-3-yl)-2,3-dihydro-1H-imidazo[4,5-c]quinolin-8-yl)-5,6-dihydropyridine-1(2H)-carboxylate, tert-butyl 4-(5-(2-(cyanoimino)-1-(6-(2-cyanopropan-2-yl)pyridin-3-yl)-3-methyl-2,3-dihydro-1H-imidazo[4,5-c]quinolin-8-yl)-3-methylpyridin-2-yl)piperazine-1-carboxylate, N-(1-(6-(2-cyanopropan-2-yl)pyridin-3-yl)-8-(2,4-dioxo-1,2,3,4-tetrahydropyrimidin-5-yl)-3-methyl-1H-imidazo[4,5-c]quinolin-2(3H)-ylidene)cyanamide, N-(8-(3-chloro-2-morpholinopyridin-4-yl)-1-(6-(2-cyanopropan-2-yl)pyridin-3-yl)-3-methyl-1H-imidazo[4,5-c]quinolin-2(3H)-ylidene)cyanamide, tert-butyl 5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl)pyridin-2-ylcarbamate, tert-butyl 5-(2-(cyanoimino)-1-(6-methoxypyridin-3-yl)-3-methyl-2,3-dihydro-1H-imidazo[4,5-c]quinolin-8-yl)-3-(trifluoromethyl)pyridin-2-ylcarbamate, N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl) benzenesulfonamide, N-(5-(2-(cyanoimino)-1-(6-(2-cyanopropan-2-yl)pyridin-3-yl)-3-methyl-2,3-dihydro-1H-imidazo[4,5-c]quinolin-8-yl)-2-methoxypyridin-3-yl) benzenesulfonamide, N-(5-(2-(cyanoimino)-1-(6-(2-cyanopropan-2-yl) pyridin-3-yl)-3-methyl-2,3-dihydro-1H-imidazo[4,5-c]quinolin-8-yl)-2-methoxypyridin-3-yl) methane sulfonamide, N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)methanesulfonamide, N-(5-(2-(cyanoimino)-1-(6-(2-cyanopropan-2-yl)pyridin-3-yl)-3-methyl-2,3-dihydro-1H-imidazo[4,5-c]quinolin-8-yl)-4-methylpyridin-2-yl)acetamide, N-(1-(4-(2-cyanopropan-2-yl) phenyl)-8-(6-(dimethylamino)-5-(trifluoromethyl) pyridin-3-yl)-3-methyl-1H-imidazo[4,5-c]quinolin-2(3H)-ylidene)cyanamide, N-(1-(6-(2-cyanopropan-2-yOpyridin-3-yl)-8-(6-((2-methoxyethoxy) methylamino)-5-(trifluoromethyppyridin-3-yl)-3-methyl-1H-imidazo[4,5-c]quinolin-2(3H)-ylidene)cyanamide, N-acetyl-N-(5-(2-(cyanoimino)-1-(4-(2-cyanopropan-2-yl) phenyl)-3-methyl-2,3-dihydro-1H-imidazo[4,5-c]quinolin-8-yl)-3-(trifluoromethyl)pyridin-2-yl)acetamide, N-acetyl-N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl) pyridin-2-yl)acetamide, 2-(cyanoimino)-1-(4-(2-cyanopropan-2-yl)phenyl)-3-methyl-2,3-dihydro-1H-imidazo[4,5-c]quinolin-8-yl)-3-(trifluoromethyl)pyridin-2-ypacetamide, N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl) pyridin-2-yl)acetamide, N-(5-(2-(cyanoimino)-1-(4-(2-cyanopropan-2-yl)phenyl)-3-methyl-2,3-dihydro-1H-imidazo[4,5-c]quinolin-8-yl)-2-methoxypyridin-3-yl)-2,4-difluorobenzenesulfonamide, N-(5-(2-(cyanoimino)-1-(6-(2-cyanopropan-2-yl)pyridin-3-yl)-3-methyl-2,3-dihydro-1H-imidazo[4,5-c]quinolin-8-yl)-3-(trifluoromethyl) pyridin-2-yl)-2-propyl-pentanamide, Methyl 2-amino-5-(2-(cyanoimino)-1-(6-(2-cyanopropan-2-yl)pyridin-3-yl)-3-methyl-2,3-dihydro-1H-imidazo[4,5-c]quinolin-8-yl)nicotinate, N-(8-(6-(benzylamino)-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide;

or a pharmaceutically acceptable salt, a stereoisomer, a tautomer or N-oxide thereof.

13. A pharmaceutical composition, comprising a therapeutically effective amount of a compound of formula (I) as defined in claim 1 or a pharmaceutically acceptable salt, or a stereoisomer, or a tautomer or N-oxide thereof and a pharmaceutically acceptable excipient or carrier.

14. A process for the preparation of a compound of formula (I),

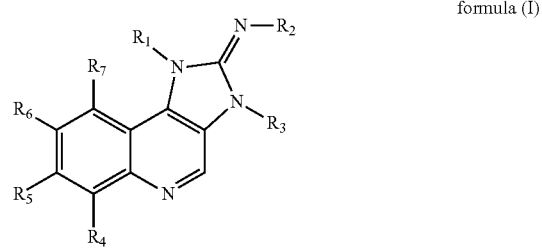

formula (I)

wherein, $R_2$ is —CN; $R_3$ is methyl or —CH$_2$CN; $R_4$, $R_5$ and $R_7$ are hydrogen; $R_1$ and $R_6$ are as defined for formula (I), in claim 1, comprising:

a) reacting a compound of formula (6);

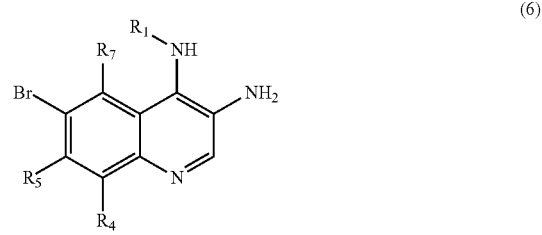

(6)

wherein, $R_4$, $R_5$ and $R_7$ are hydrogen and $R_1$ is as defined for formula (I) in claim 1, with a reagent selected from diphenylcyanocarbonoimidate or dimethyl cyanocarbonimidodithioate in the presence of a base selected from diisopropylethylamine or cesium carbonate, to obtain a compound of formula (7)

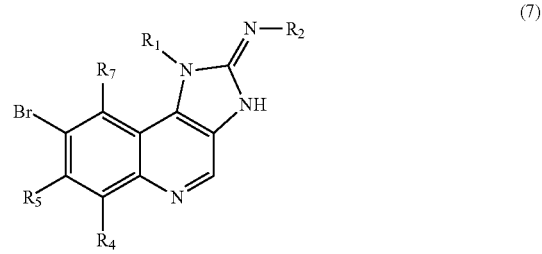

(7)

b) reacting the compound of formula (7), wherein $R_2$ is —CN; $R_4$, $R_5$ and $R_7$ are hydrogen and $R_1$ is as defined for formula (I) in claim 1, with a methylating agent selected from methyliodide or bromoacetonitrile in the presence of a base, sodium hydride to obtain a compound of formula (8)

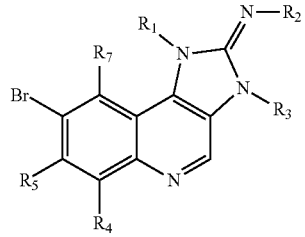

(8)

wherein $R_2$ is —CN; $R_3$ is methyl or —$CH_2CN$; $R_4$, $R_5$ and $R_7$ are hydrogen; $R_1$ is as defined for formula (I) in claim 1;

c) reacting the compound of formula (8) with a compound of formula $R_6$—$BOH_3$ in the presence of, palladium dichlorobis triphenylphosphine as a coupling agent and sodium carbonate as a base to obtain a compound of formula (I), wherein $R_2$ is —CN; $R_3$ is methyl or —$CH_2CN$; $R_4$, $R_5$ and $R_7$ are hydrogen; $R_1$ and $R_6$ are as defined for formula (I) in claim 1;

d) optionally converting the resulting compound into a pharmaceutically acceptable salt.

* * * * *

UNITED STATES PATENT AND TRADEMARK OFFICE
CERTIFICATE OF CORRECTION

PATENT NO. : 9,062,046 B2  
APPLICATION NO. : 13/810431  
DATED : June 23, 2015  
INVENTOR(S) : Sanjay Kumar et al.

Page 1 of 1

It is certified that error appears in the above-identified patent and that said Letters Patent is hereby corrected as shown below:

Title page, insert item --60 Related U.S. Application Data: Provisional Application No. 61/364,927, filed on July 16, 2010--.

Signed and Sealed this  
Fifth Day of January, 2016

Michelle K. Lee  
*Director of the United States Patent and Trademark Office*